Figure 1:
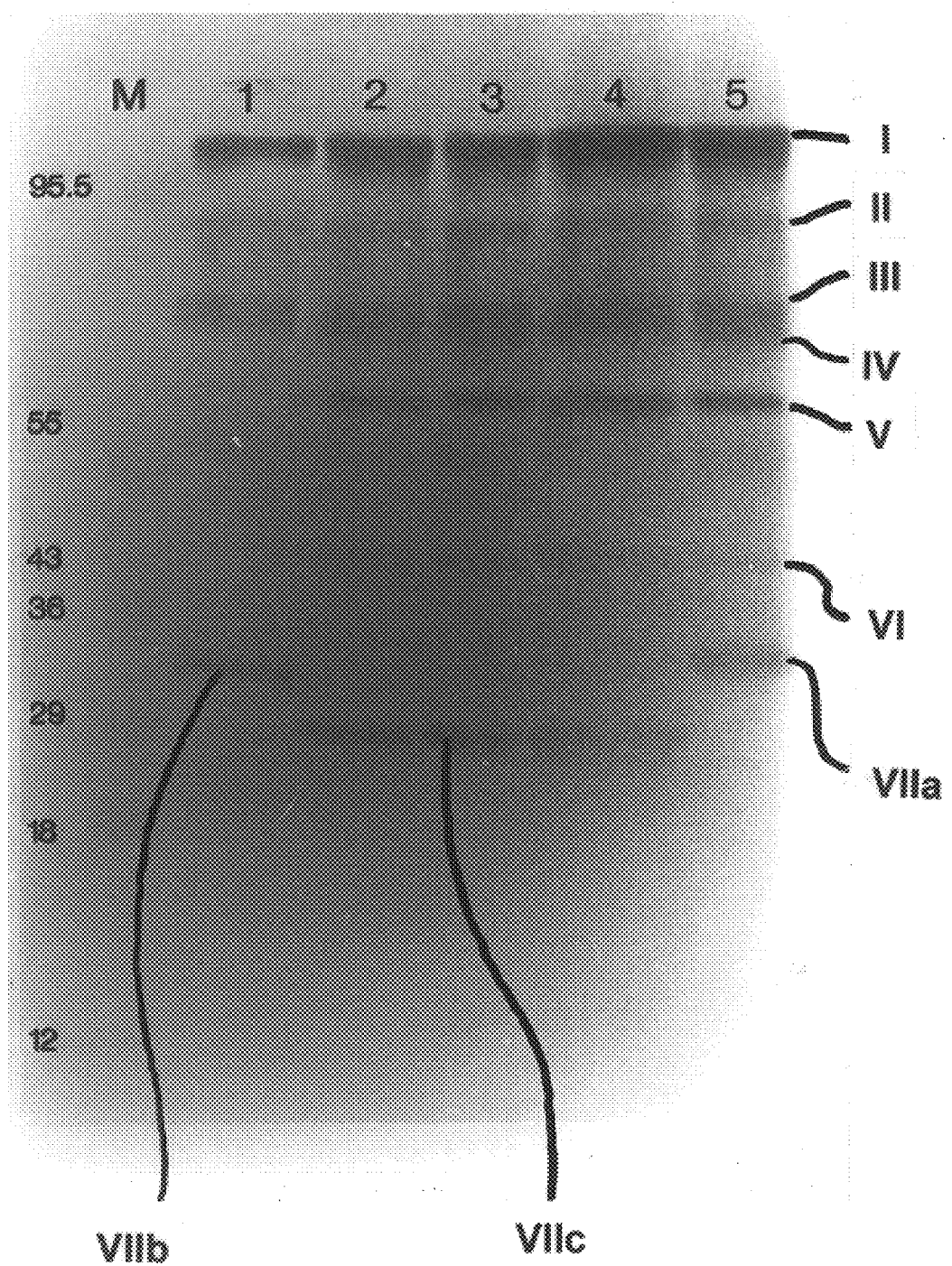

US005932705A

United States Patent [19]
Berget et al.

[11] Patent Number: 5,932,705
[45] Date of Patent: Aug. 3, 1999

[54] METHODS AND COMPOSITIONS FOR THE TREATMENT AND DIAGNOSIS OF SHIPPING FEVER

[75] Inventors: Peter Berget, Pittsburgh, Pa.; Michael Engler, Houston, Tex.; Sarah Highlander, Houston, Tex.; George Weinstock, Houston, Tex.

[73] Assignee: Board of Regents, University of Texas Systrem

[21] Appl. No.: 08/286,690

[22] Filed: Aug. 5, 1994

Related U.S. Application Data

[62] Division of application No. 07/899,100, Jun. 15, 1992, Pat. No. 5,336,491, which is a continuation of application No. 07/540,261, Jun. 18, 1990, abandoned, which is a division of application No. 07/085,430, Aug. 13, 1987, Pat. No. 4,957,739, which is a continuation of application No. 06/935,806, Nov. 28, 1986, abandoned.

[51] Int. Cl.$^6$ .............................. A23J 1/00; A61K 39/00; A61K 39/102
[52] U.S. Cl. .................. 530/413; 424/190.1; 424/255.1; 435/69.1; 435/69.3; 435/71.1; 435/71.2; 530/344; 530/350; 530/387.9; 530/388.4; 530/389.5
[58] Field of Search .............................. 424/255.1, 190.1; 530/350, 344, 387.9, 388.4, 389.5, 413; 435/69.1, 69.3, 71.1, 71.2

[56] References Cited

U.S. PATENT DOCUMENTS

| 4,328,210 | 5/1982 | Kucera | 424/92 |
|---|---|---|---|
| 4,335,106 | 6/1982 | Kucera | 424/92 |
| 4,388,299 | 6/1983 | Kucera | 424/92 |
| 4,506,017 | 3/1985 | Kucera | 424/93 |
| 4,559,306 | 12/1985 | Kucera | 424/92 |
| 4,626,430 | 12/1986 | Kucera | 424/92 |
| 5,055,400 | 10/1991 | Lo et al. | 435/69.1 |
| 5,165,924 | 11/1992 | Shewen et al. | 424/88 |

FOREIGN PATENT DOCUMENTS

| 2023420 | 1/1980 | United Kingdom | 424/92 |

OTHER PUBLICATIONS

Biberstein, "HPA in Veterinary Medicine," pp. 62–66, date of publication unsure.
Frank, "Respiratory Disease in Cattle," from Proceedings of the 83rd Annual Meeting USAHA, 1979.
Markham et al. (1980), Am. J. Vet. Res., 41:18–22.
Karn et al. (1980), Proc. Natl. Acad. Sci., U.S.A., 77:5512.
Kaehler et al. (1980), Infect. Immun., 30:615.
Wilkie, "Pasteurella Immunization—Helpful or Harmful?," Notes from presentation at AABP Conference, 1980.
Himmel et al. (1982), Am. J. Vet. Res., 43:764–767.
Baluyut et al. (1981), Am. J. Vet. Res., 42:1920–1926.
Mtulla and Thomson (1981), Can. Vet. J., 22:1.
Shewen et al. (1982), Infect. Immun., 35:91.
Markham et al. (1982), Am. J. Vet. Res., 43:285.
Yates et al. (1983), Can. J. Comp. Med., 47:250.
Frischauf et al. (1983), J. Mol. Biol., 170:827.
Otulakowski et al. (1983), Infect. Immun., 42:64.
Shewen et al. (1983), Am. J. Vet. Res., 44:715.
Shewen et al. (1983), Can. J. Comp. Med., 47:497.
Kucera et al. (1983), Am. J. Vet. Res., 44:1848.
Cho et al. (1984), Can J. Comp. Med., 48:151.
Filion et al. (1984), Can J. Comp. Med., 48:268.
Confer et al. (1985), Vet. Immunol. Immunopath., 10:265.
Lessley et al. (1985), Vet. Immunol. Immunopath., 10:279.
Frank, "Bacteria as Etiologic Agents in Bovine Respiratory Disease," pp. 348–362.
Lo et al. (1985), Infect. Immun., 50:667–671.
Gonzalez–Rayos et al. (1986), Infect. Immun., 53:505.
Lo et al. (1986), Biochem. Cell. Biol., 64:73.
Promega Biotec. Spec. Sheets.
Chang et al. (1986), Am. J. Vet. Res., 47:47:716.
Dialog Search Report.
Squire et al. (1984), Infect. Immun., 45(3):667–673.
McKinney et al. (1985), Vet. Microbiology, 10:465 (Abstract only).
Donachie et al. (1983), Vet. Microbiology, 8:199 (Abstract only).
Wilkie et al. (1980), Am. J. Vet. Res., 41:1773–1778.
Gentry et al. (1982), Am. J. Vet. Res., 43:2070–2073.
Gilmour et al. (1982), Vet. Record, 110:450.
Gentry et al. (1985), Vet. Immunol. Immunopath., 9:239–250.
Shewen et al. (1985), Am. J. Vet. Res., 46:1212–1214.
Durham et al. (1986), Am. J. Vet. Res., 47:1946–1951.
Mosier et al. (1986), Am. J. et. Res., 47:2233–2241.
Confer et al. (1988), JAVMA, 193:1308–1316.
Highlander et al. (1989), DNA, 8:15–28.
Mosier et al. (1989), Infect. Immun., 57:711–716.
Donachie et al. (1984), "Comparison of Cell Surface Antigen Extracts From Two Serotypes of Pasteurella haemolytica," J. Gen. Microbiology, 130:1209–1216.
Shewen and Wilkie (1983), "Immunity to Pasteurella haemolytica Serotype 1," Abstract for N. American Symposium on Bovine Respiratory Disease, Amarillo, Texas, pp. 480–481.

Primary Examiner—James C. Housel
Assistant Examiner—Jennifer Shaver
Attorney, Agent, or Firm—Arnold, White and Durkee

[57] ABSTRACT

Novel compositions are disclosed for use in the treatment or diagnosis of bovine pasteurellosis, commonly referred to as Shipping Fever. Cell-free Pasteurella haemolytica supernatants are employed to provide individual antigen compositions, identified through reaction with sera from naturally-infected or convalescent cattle. In particular, at least seven individual P. haemolytica antigen groups were recognized in cell-free culture supernatants. Purified P. haemolytica supernatant, formulated in a suitable pharmaceutical vaccine composition is shown to elicit a specific immune response, in both cows and rabbits, directed against the individual immunoreactive P. haemolytica polypeptides identified. Also disclosed are novel recombinant cells, plasmids and bacteriophage which include transcriptionally active P. haemolytica antigen genes. Recombinant clones are similarly selected to be reactive with naturally-infected antisera. Examples, and further disclosure, are also provided which demonstrate the utility of a presently disclosed antibody and antigen compositions in immuno-detection of both antigens and antibodies in various biological samples.

13 Claims, 21 Drawing Sheets

```
                                                    Nucleotide #
BglII                            *                            *
GATCTATACGCTTTTATCCAAAGCAGAAAG AATTAGGCAAAATTGCCTACTTTAAAGGAG 90                            *
GTAAATTAGATAAAAAAACAGCAAAAAAAC GTTTTGATACATATCAAGAAGAGCTGGCAA

*                          180
CACGACTTAAAAATGAATTTAATTTTATTA AAAAATAGAAGGAGACATCCCTTATGGGAA
                                          PtxA protein:   M  G

*                            *
CTAGACTTACAACCCTATCAAATGGGCTAA AAAACACTTTAACGGCAACCAAAAGTGGCT
T  R  L  T  T  L  S  N  G  L   K  N  T  L  T  A  T  K  S  G

270                            *
TACATAAAGCCGGTCAATCATTAACCCAAG CCGGCAGTTCTTTAAAAACTGGGGCAAAAA
L  H  K  A  G  Q  S  L  T  Q   A  G  S  S  L  K  T  G  A  K
                       30

*                          360
AAATTATCCTCTATATTCCCCAAAATTACC AATATGATACTGAACAAGGTAATGGTTTAC
K  I  I  L  Y  I  P  Q  N  Y   Q  Y  D  T  E  Q  G  N  G  L
                                                    60

*                            *
AGGATTTAGTCAAAGCGGCCGAAGAGTTGG GGATTGAGGTACAAAGAGAAGAACGCAATA
Q  D  L  V  K  A  A  E  E  L   G  I  E  V  Q  R  E  E  R  N

450                            *
ATATTGCAACAGCTCAAACCAGTTTAGGCA CGATTCAAACCGCTATTGGCTTAACTGAGC
N  I  A  T  A  Q  T  S  L  G   T  I  Q  T  A  I  G  L  T  E
                       90

*                          540
GTGGCATTGTGTTATCCGCTCCACAAATTG ATAAATTGCTACAGAAAACTAAAGCAGGCC
R  G  I  V  L  S  A  P  Q  I   D  K  L  L  Q  K  T  K  A  G
                                                  120
```

FIG. 9A

```
            *                              *
AAGCATTAGGTTCTGCCGAAAGCATTGTAC  AAAATGCAAATAAAGCCAAAACTGTATTAT
 Q  A  L  G  S  A  E  S  I  V    Q  N  A  N  K  A  K  T  V  L

630                                *
CTGGCATTCAATCTATTTTAGGCTCAGTAT  TGGCTGGAATGGATTTAGATGAGGCCTTAC
 S  G  I  Q  S  I  L  G  S  V    L  A  G  M  D  L  D  E  A  L
              150

*                             720
AGAATAACAGCAACCAACATGCTCTTGCTA  AAGCTGGCTTGGAGCTAACAAATTCATTAA
 Q  N  N  S  N  Q  H  A  L  A    K  A  G  L  E  L  T  N  S  L
                                                       180

*                             *
TTGAAAATATTGCTAATTCAGTAAAAACAC  TTGACGAATTTGGTGAGCAAATTAGTCAAT
 I  E  N  I  A  N  S  V  K  T    L  D  E  F  G  E  Q  I  S  Q

810                                       *
TTGGTTCAAAACTACAAAATATCAAAGGCT  TAGGGACTTTAGGAGACAAACTCAAAAATA
 F  G  S  K  L  Q  N  I  K  G    L  G  T  L  G  D  K  L  K  N
              210

*                             900
TCGGTGGACTTGATAAAGCTGGCCTTGGTT  TAGATGTTATCTCAGGGCTATTATCGGGCG
 I  G  G  L  D  K  A  G  L  G    L  D  V  I  S  G  L  L  S  G
                                                       240

*                                       *
CAACAGCTGCACTTGTACTTGCAGATAAAA  ATGCTTCAACAGCTAAAAAAGTGGGTGCGG
 A  T  A  A  L  V  L  A  D  K    N  A  S  T  A  K  K  V  G  A

990                                       *
GTTTTGAATTGGCAAACCAAGTTGTTGGTA  ATATTACCAAAGCCGTTTCTTCTTACATTT
 G  F  E  L  A  N  Q  V  V  G    N  I  T  K  A  V  S  S  Y  I
              270
```

FIG. 9B

```
                                    *                                        1080
TAGCCCAACGTGTTGCAGCAGGTTTATCTT  CAACTGGGCCTGTGGCTGCTTTAATTGCTT
 L  A  Q  R  V  A  A  G  L  S    S  T  G  P  V  A  A  L  I  A
                                                       300

*                                          *
CTACTGTTTCTCTTGCGATTAGCCCATTAG  CATTTGCCGGTATTGCCGATAAATTTAATC
 S  T  V  S  L  A  I  S  P  L    A  F  A  G  I  A  D  K  F  N

1170                                                 *
ATGCAAAAAGTTTAGAGAGTTATGCCGAAC  GCTTTAAAAAATTAGGCTATGACGGAGATA
 H  A  K  S  L  E  S  Y  A  E    R  F  K  K  L  G  Y  D  G  D
                   330

*                                        1260
ATTTATTAGCAGAATATCAGCGGGGAACAG  GGACTATTGATGCATCGGTTACTGCAATTA
 N  L  L  A  E  Y  Q  R  G  T    G  T  I  D  A  S  V  T  A  I
                                                       360

*                                          *
ATACCGCATTGGCCGCTATTGCTGGTGGTG  TGTCTGCTGCTGCAGCCGGCTCGGTTATTG
 N  T  A  L  A  A  I  A  G  G    V  S  A  A  A  A  G  S  V  I

1350                                                 *
CTTCACCGATTGCCTTATTAGTATCTGGGA  TTACCGGTGTAATTTCTACGATTCTGCAAT
 A  S  P  I  A  L  L  V  S  G    I  T  G  V  I  S  T  I  L  Q
                   390

*                                        1440
ATTCTAAACAAGCAATGTTTGAGCACGTTG  CAAATAAAATTCATAACAAAATTGTAGAAT
 Y  S  K  Q  A  M  F  E  H  V    A  N  K  I  H  N  K  I  V  E
                                                       420

*                                          *
GGGAAAAAAATAATCACGGTAAGAACTACT  TTGAAAATGGTTACGATGCCCGTTATCTTG
 W  E  K  N  N  H  G  K  N  Y    F  E  N  G  Y  D  A  R  Y  L
```

FIG. 9C

```
                          1530
CGAATTTACAAGATAATATGAAATTCTTAC TGAACTTAAACAAAGAGTTACAGGCAGAAC
 A  N  L  Q  D  N  M  K  F  L    L  N  L  N  K  E  L  Q  A  E
                 450

*                           1620
GTGTCATCGCTATTACTCAGCAGCAATGGG ATAACAACATTGGTGATTTAGCTGGTATTA
 R  V  I  A  I  T  Q  Q  Q  W    D  N  N  I  G  D  L  A  G  I
                                                      480

*                              *
GCCGTTTAGGTGAAAAAGTCCTTAGTGGTA AAGCCTATGTGGATGCGTTTGAAGAAGGCA
 S  R  L  G  E  K  V  L  S  G    K  A  Y  V  D  A  F  E  E  G

1710                                        *
AACACATTAAAGCCGATAAATTAGTACAGT TGGATTCGGCAAACGGTATTATTGATGTGA
 K  H  I  K  A  D  K  L  V  Q    L  D  S  A  N  G  I  I  D  V
                    510

*                           1800
GTAATTCGGGTAAAGCGAAAACTCAGCATA TCTTATTCAGAACGCCATTATTGACGCCGG
 S  N  S  G  K  A  K  T  Q  H    I  L  F  R  T  P  L  L  T  P
                                                      540

*                             *
GAACAGAGCATCGTGAACGCGTACAAACAG GTAAATATGAATATATTACCAAGCTCAATA
 G  T  E  H  R  E  R  V  Q  T    G  K  Y  E  Y  I  T  K  L  N

1890                                        *
TTAACCGTGTAGATAGCTGGAAAATTACAG ATGGTGCAGCAAGTTCTACCTTTGATTTAA
 I  N  R  V  D  S  W  K  I  T    D  G  A  A  S  S  T  F  D  L
                    570
```

FIG. 9D

```
                                        *                                    1980
CTAACGTTGTTCAGCGTATTGGTATTGAAT  TAGACAATGCTGGAAATGTAACTAAAACCA
 T  N  V  V  Q  R  I  G  I  E    L  D  N  A  G  N  V  T  K  T
                                                              600

*                                         *
AAGAAACAAAAATTGCCCGGAAACTTGGTG  AAGGTGATGACAACGTATTTGTTGGTTCTG
 K  E  T  K  I  I  A  K  L  G    E  G  D  D  N  V  F  V  G  S

2070                                 *
GTACGACGGAAATTGATGGCGGTGAAGGTT  ACGACCGAGTTCACTATAGCCGTGGAAACT
 G  T  T  E  I  D  G  G  E  G    Y  D  R  V  H  Y  S  R  G  N
                     630

*                         2160
ATGGTGCTTTAACTATTGATGCAACCAAAG  AGACCGAGCAAGGTAGTTATACCGTAAATC
 Y  G  A  L  T  I  D  A  T  K    E  T  E  Q  G  S  Y  T  V  N
                                                              660

*                            *
GTTTCGTAGAAACCGGTAAAGCACTACACG  AAGTGACTTCAACCCATACCGCATTAGTGG
 R  F  V  E  T  G  K  A  L  H    E  V  T  S  T  H  T  A  L  V

2250                                   *
GCAACCGTGAAGAAAAAATAGAATATCGTC  ATAGCAATAACCAGCACCATGCCGGTTATT
 G  N  R  E  E  K  I  E  Y  R    H  S  N  N  Q  H  H  A  G  Y
                     690

*                         2340
ACACCAAAGATACCTTGAAAGCTGTTGAAG  AAATTATCGGTACATCACATAACGATATCT
 Y  T  K  D  T  L  K  A  V  E    E  I  I  G  T  S  H  N  D  I
                                                              720

*                              *
TTAAAGGTAGTAAGTTCAATGATGCCTTTA  ACGGTGGTGATGGTGTCGATACTATTTACG
 F  K  G  S  K  F  N  D  A  F    N  G  G  D  G  V  D  T  I  Y
```

FIG. 9E

```
                        2430                                          *
GTAACGACGGCAATGACCGCTTATTTGGTG  GTAAAGGCGATGATATTCTCGATGGTGGAA
 G  N  D  G  N  D  R  L  F  G   G  K  G  D  D  I  L  D  G  G
                   750

*                              2520
ATGGTGATGATTTTATCGATGGCGGTAAAG  GCAACGACCTATTACACGGTGGCAAGGGCG
 N  G  D  D  F  I  D  G  G  K   G  N  D  L  L  H  G  G  K  G
                                                    780

*                                 *
ATGATATTTTCGTTCACCGTAAAGGCGATG  GTAATGATATTATTACCGATTCTGACGGCA
 D  D  I  F  V  H  R  K  G  D   G  N  D  I  I  T  D  S  D  G

2610                                           *
ATGATAAATTATCATTCTCTGATTCGAACT  TAAAAGATTTAACATTTGAAAAAGTTAAAC
 N  D  K  L  S  F  S  D  S  N   L  K  D  L  T  F  E  K  V  K
                    810

*                              2700
ATAATCTTGTCATCACGAATAGCAAAAAAG  AGAAAGTGACCATTCAAAACTGGTTCCGAG
 H  N  L  V  I  T  N  S  K  K   E  K  V  T  I  Q  N  W  F  R
                                                    840

*                                 *
AGGCTGATTTTGCTAAAGAAGTGCCTAATT  ATAAAGCAACTAAAGATGAGAAAATCGAAG
 E  A  D  F  A  K  E  V  P  N   Y  K  A  T  K  D  E  K  I  E

2790
AAATCATCGGTCAAAATGGCGAGCGGATCA  CCTCAAAGCAAGTTGATGATCTTATCGCAA
 E  I  I  G  Q  N  G  E  R  I   T  S  K  Q  V  D  D  L  I  A
                    870

*                              2880
AAGGTAACGGCAAAATTACCCAAGATGAGC  TATCAAAAGTTGTTGATAACTATGAATTGC
 K  G  N  G  K  I  T  Q  D  E   L  S  K  V  V  D  N  Y  E  L
                                                    900
```

FIG. 9F

```
                         *                                              *
TCAAACATAGCAAAAATGTGACAAACAGCT  TAGATAAGTTAATCTCATCTGTAAGTGCAT
 L  K  H  S  K  N  V  T  N  S   L  D  K  L  I  S  S  V  S  A

2970                                           *
TTACCTCGTCTAATGATTCGAGAAATGTAT  TAGTGGCTCCAACTTCAATGTTGGATCAAA
 F  T  S  S  N  D  S  R  N  V   L  V  A  P  T  S  M  L  D  Q
                930

*                                 3060
GTTTATCTTCTCTTCAATTTGCTAGAGCAG  CTTAATTTTAATTGATTGGCAACTCTATAT
 S  L  S  S  L  Q  F  A  R  A   A  *
                               953

*                                              *
TGTTTCACACATTATAGAGTTGCCGTTTTA  TTTTATAAAAGGAGACAATATGGAAGCTAA

3150
CCATCAAAGGAATGATCTTGGTTTAGTTGC  CCTCACTATGTTGGCACAATACCATAATAT

*                                 3240
TTCGCTTAATCCGGAAGAAATAAAACATAA  ATTTGATCTTGACGGAAAAGGGCTTTCTTT

*                                        *
AACTGCTTGGCTTTTAGCTGCAAAATCGTT  AGCGTTGAAAGCGAAACACATTAAAAAAGA

3330                                              *
GATTTCCCGCTTACACTTGGTGAATTTACC  GGCATTAGTTTGGCAAGATAACGGTAAACA

*                                 3420
TTTTTTATTGGTAAAAGTGGATACCGATAA  TAACCGCTATTTAACTTACAATTTGGAACA

*                                        *
AGATGCTCCACAAATTCTGTCAACAGACGA  ATTTGAAGCCTGCTATCAAGGGCAGTTAAT

3510                                              *
TTTGGTCACGTCCAGAGCTTCCGTAGTAGG  TCAATTAGCAAAGTTCGATTTCACCTGGTT
```

FIG. 9G

```
                              3600
TATTCCGGCGGTGATCAAATACCGAAAAAT CTTTCTAGAAACCTTGATTGTTTCGATCTT

*                              *
TTTGCAAATTTTTGCCCTAATTACACCGCT ATTCTTCCAAGTTGTTATGGATAAAGTACT

3690                           *
GGTGCATCGAGGTTTTTCAACCTTGAATAT CATTACGGTTGCCTTAGCTATTGTGATCAT

*                              3780
CTTTGAAATTGTACTAAGTGGTTTGAGAAC CTATGTTTTTCTCATAGCACTAGCCGTAT

*                              *
TGATGTTGAATTAGGCGCTAAATTATTTCG ACATTTATTATCACTACCCATTTCTTATTT

3870                           *
TGAAAACAGACGAGTTGGAGATACAGTCGC TAGGGTTAGAGAATTAGATCAAATTCGTAA

*                              3960
TTTCCTTACCGGACAAGCATTAACCTCGGT GTTAGATCTCTTATTCTCTTTTATCTTTTT

*                              *
TGCCGTAATGTGGTATTACAGCCCAAAATT AACCTTGGTAATTCTTGGTTCATTGCCCTG

4050                           *
CTATATTTTATGGTCAATTTTTATTAGTCC GATTTTAAGACGGCGTTTAGATGAGAAATT

*                              4140
TGCCCGAAGTGCTGATAACCAAGCATTCTT AGTTGAGTCGGTAACAGCCATCAATATGAT

*                              *
TAAAGCGATGGCGGTTGCTCCACAAATGAC GGATACATGGGATAAACAGCTGGCAAGCTA

4230                           *
TGTTTCATCAAGTTTCCGTGTCACCGTATT AGCAACCATTGGGCAACAAGGTGTACAACT

*                              4320
TATTCAAAAAACCGTTATGGTGATTAACCT TTGGTTAGGGGCACACTTAGTTATTTCAGG
```

FIG. 9H

```
                              *                                    *
CGATCTGAGTATTGGGCAATTAATTGCCTT TAATATGCTATCAGGGCAAGTGATTGCACC

4410                                    *
GGTGATTCGGCTGGCTCAGCTCTGGCAAGA TTTCCAACAAGTTGGGATTTCCGTCACTCG

*                                 4500
CTTAGGTGATGTTTTAAACTCTCCAACCGA ACAATATCAAGGCAAATTATCACTACCAGA

*                                    *
AATAAAAGGCGATATCTCATTTAAAAATAT CCGCTTTAGATATAAACCAGATGCACCAAC

4590                                    *
TATTTTAAATAATGTGAATTTAGAAATTAG GCAAGGAGAAGTGATTGGGATTGTTGGACG

*                                 4680
TTCCGGTTCAGGCAAAAGTACTCTGACTAA ATTACTGCAACGTTTTTATATTCCTGAAAA

*                                    *
TGGGCAGGTTTTGATTGATGGACATGATCT AGCCTTAGCTGATCCAAACTGGCTACGCCG

4770                                    *
TCAAATAGGTGTAGTGCTGCAAGATAATGT GTTATTAAACCGCAGTATCCGAGAAAATAT

*                                 4860
TGCGCTATCAGATCCAGGAATGCCAATGGA GCGAGTAATTTATGCAGCAAAATTAGCAGG

*                                    *
GGCTCACGATTTTATTTCAGAATTGCGTGA AGGTTATAACACCATTGTGGGTGAACAAGG

4950                                    *
AGCGGGGCTTTCAGGCGGGCAACGCCAACG GATTGCGATTGCTCGAGCTTTGGTAAACAA

*                                 5040
CCCGAAAATCCTGATTTTTGATGAGGCAAC CAGTGCCCTCGATTACGAATCTGAGCATAT

*                                    *
TATTATGCAAAATATGCAAAAAATATGCCA AGGCAGAACCGTGATTTTGATTGCACATCG
```

FIG. 9I

```
                      5130                                    *
TTTATCGACCGTCAAAAATGCGGATCGAAT  TATTGTGATGGAAAAGGGGGAAATTGTTGA

*                                  5220
GCAAGGCAAGCACCACGAATTACTGCAAAA  CAGTAACGGACTTTATTCCTACTTACACCA

*                                     *
ATTACAACTTAATTAAGAAGGAAAACAATG  AAAATATGGCTTAGTGGTATTTATGAATTT

5310                                    *
TTCCTACGCTATAAAAACATTTGGGCAGAA  GTATGGAAAATTCGTAAAGAATTAGACCAC

*                                  5400
CCAAACAGAAAAAAAGACGAAAGTGAATTT  TTACCGGCACATTTAGAACTGATTGAAACC

*                                     *
CCGGTTTCTAAAAAACCACGTCTAATTGCT  TATTTGATTATGCTATTTTTAGTTGTGGCA

5490                                    *
ATTGTGCTTGCCAGTGTAAGCAAAGTTGAA  ATTGTGGCGACTGCTCCCGGTAAATTAACT

*                                  5580
TTTAGTGGCAGAAGTAAAGAAATTAAACCG  ATTGAAAACGCCATTGTACAAGAAATTTTC

*                                     *
GTTAAAGATGGGCAGTTTGTGGAAAAAGGG  CAATTATTAGTCAGCTTAACTGCATTGGGT

5670                                    *
TCTGATGCAGATATCAAAAAGACCATGGCT  TCACTTTCTTTAGCTAAACTGGAGAACTAT

*                                  5760
CGCTACCAAACTTTGCTTACTGCCATTGAA  AAAGAGTCCTTGCCGGTGATTGATTTATCT

*                                     *
AGAACCGAATTTAAAGATTCATCGGAAGAA  GATCGACTACGTATTAAACACTTAATTGAG

5850                                    *
GAGCAATACACCACTTGGCAAAAACAAAAA  ACACAGAAAACTTTAGCGTATAAGCGTAAA
```

FIG. 9J

```
                                    *                                         5940
GAGGCTGAAAAACAAACAATATTTGCCTAT      GTCCGTAAATATGAAGGTGCAACACGTATT

*                                         *
GAACAAGAAAAATTAAAAGACTTTAAGGCA      CTTTATAAACAGAAGTCTTTATCTAAGCAC

6030                                         *
GAACTTCTTGCGCAAGAAAATAAATTAATT      GAGGCTCAGAATGCAGTAGCTGTTTATCGC

*                                         6120
TCAAAATTAAATGAATTAGAAAATGATCTA      CTCAATGTAAAAGAAGAACTTGAATTGATC

*                                         *
ACGCAATTCTTTAAAAGCGATGTGTTGGAA      AAATTAAAGCAACATATTGAAAATGAACGC

6210                                         *
CAACTTCGGCTCGAGTTAGAAAAAAATAAT      CAACGCAGACAGGCCTCGATGATCAGAGCA

*                                         6300
CCGGTTTCCGGTACGGTTCAGCAACTGAAA      ATTCACACTATAGGTGGTGTTGTTACGACT

*                                         *
GCTGAAACCTTGATGATCATTGTGCCGGAA      GACGATGTGTTAGAGGCCACCGCTCTGGTT

6390                                         *
CCAAACAAAGATATCGGCTTTGTTGCAGCA      GGGCAGGAGGTGATTATTAAAGTGGAAACT

*                                         6480
TTCCCTTATACACGCTATGGTTATCTAACT      GGTCGAATTAAACATATTAGCCCGGATGCG

*                                         *
ATTGAACAACCTAATGTAGGCTTAGTTTTT      AATGCAACTATAGCTATAGATAGGAAGAAT

6570                                         *
CTAACATCGCCTGATGGGCGAAAAATTGAT      TTGAGTTCAGGTATGACAATAACTGCTGAA

*                                         6660
ATCAAAACCGGTGAACGGAGTGTAATGAGT      TATTTACTCAGCCCATTAGAAGAATCTGTC
```

FIG. 9K

```
                    SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
          (A) LENGTH: 10 amino acids
          (B) TYPE: amino acid
          (C) STRANDEDNESS:
          (D) TOPOLOGY: linear (xi) SEQUENCE DESCRIPTION: SEQ ID NO:1:

Met Gly Thr Arg Leu Thr Thr Leu Ser Asn
1               5                   10

(2) INFORMATION FOR SEQ ID NO:2:

(i) SEQUENCE CHARACTERISTICS:
          (A) LENGTH: 10 amino acids
          (B) TYPE: amino acid
          (C) STRANDEDNESS:
          (D) TOPOLOGY: linear (xi) SEQUENCE DESCRIPTION: SEQ ID NO:2:

Leu Ser Ser Leu Gln Phe Ala Arg Ala Ala
1               5                   10
```

METHODS AND COMPOSITIONS FOR THE TREATMENT AND DIAGNOSIS OF SHIPPING FEVER

The present application is a divisional of U.S. Ser. No. 07/899,100 filed Jun. 15, 1992 (now U.S. Pat. No. 5,336,491), which was a continuation of U.S. Ser. No. 07/540,261 filed Jun. 18, 1990 (now abandoned), which was a divisional of U.S. Ser. No. 07/085,430 filed Aug. 13, 1987 (now U.S. Pat. No. 4,957,739), which was a continuation of U.S. Ser. No. 06/935,806 filed Nov. 28, 1986 (now abandoned).

BACKGROUND OF THE INVENTION

1. Field of the Invention

The present invention is directed to methods and compositions for prophylaxis, treatment and diagnosis of pneumonic pasteurellosis in cattle. More particularly, the present invention relates to the identification and isolation of *Pasterurella haemolytica* antigens, using both recombinant DNA and non-recombinant technology, and the use of such antigens in the formulation of antigen and antibody-containing compositions for the treatment and diagnosis of pasteurellosis.

2. Description of the Related Art

Pneumonic pasteurellosis, commonly referred to as Shipping Fever, is a major cause of economic loss in feedlot cattle. While there is evidence to suggest that several etiologic agents, for example, combinations of stress, respiratory viruses, and various bacteria may participate in this disease, *Pasterurella haemolytica*, serotype A1, appears to be the major cause of the severe fibrinous pneumonia which can be seen.

The pathogenesis of the disease is poorly understood. Overgrowth of the lung with *P. haemolytica* with resultant bronchial pneumonia is thought to be at least partly caused by a preceding viral infection. Studies have suggested that parainfluenza-3 virus can impair pulmonary clearance of *P. haemolytica*. Moreover, infectious bovine rhinotracheitis virus has been shown to predispose pulmonary infection with *P. haemolytica*. In experimental bacterial infections in mice which have been pre-infected with virus, it has been shown that protection can be afforded by prior inoculation with either the viral or bacterial agent.

However, attempts to protect cattle by immunization with respiratory viral vaccines and Pasteurella bacterins have generally proved unsuccessful. It has been proposed that antigenic challenge with dead bacteria, as is the case with bacterin immunization, is insufficient due to the nature of the *P. haemolytica* infection—live *P. haemolytica* apparently produce a cytotoxin having specificity for ruminant leukocytes. Thus, it is posited that following infection with *P. haemolytica*, the infected cow's immune system is suppressed to the extent that effective immunosurveillance is compromised and the infective organism can not effectively be challenged. The failure of Pasteurella bacterins to provide an effective immunization has been partly ascribed to the absence of sufficiently antigenic amounts of this leukotoxin in the bacterin preparation. The cytotoxin is thus believed to contribute to the pathogenesis of pneumonic pasteurellosis by impairing primary lung defense and subsequent immune response, or by induction of inflammation as a consequence of leukocyte lysis.

The physicochemical nature of the leukotoxin is only poorly understood. As noted, this toxin exerts no toxic effects on non-ruminant leukocytes. However, the toxic effects of the toxin on ruminant leukocytes is dose dependant—at lower doses, generally only subtle alterations in various metabolic processes are noted, whereas higher concentrations can result in loss of membrane integrity and cell death. Apparent species specificity of the leukotoxic effects of living *P. haemolytica*, and cell-free *P. haemolytica* supernatants, supports the hypothesis that the leukotoxin itself is involved in determining the species specificity of the Pasteurella-induced pneumonia. Moreover, experimental evidence from studies of the interactions of *P. haemolytica* and its culture supernatant with ruminant alveolar macrophages, peripheral blood monocytes, neutrophils, and lymphocytes suggests that *P. haemolytica* leukotoxin is important for successful colonization and growth of *P. haemolytica* in pulmonary tissues. Thus, cytotoxic effects of the leukotoxin for leukocytes in pulmonary tissues probably contribute to the pathogenesis of the disease.

In contrast with bacterin immunization, immunization protocols employing live *P. haemolytica*, and various protein extracts of *P. haemolytica*, have been shown to protect cattle against experimental challenge exposure to the bacterium. However, most of these studies involved experimental challenge exposure to live *P. haemolytica* organisms, in either mice, where the organism induces a septicemia rather than a respiratory syndrome, or cattle, where the organism is aritifically introduced into the cattle's lungs. As such, neither of these test systems represent a natural disease state, and are thus not believed to entirely correspond to natural pasteurellosis.

In 1985, Confer and Lessley investigated a series of saline protein capsular extracts of *P. haemolytica* and identified a number of antigen groups through immuno-reaction with immune sera obtained from cows which had been immunized with live *P. haemolytica* organisms (Vet. Immunol. and Immunopath., vol. 10, pp. 265 and 279). Antibody response to immunization with various of these capsular extracts was found to correlate with resistance to an experimental challenge of *P. haemolytica* organisms. However, as noted, these studies involved the use of capsular (i.e.—cell membrane) proteins which were then immunoidentified using experimentally induced antisera rather than antisera from pasteurellosis-infected cattle. Moreover, it is believed that the use of capsular proteins, rather than secreted proteins, and the use of experimentally induced antisera, rather than antisera from diseased cattle, represent inherent drawbacks to such an approach to the identification of antigens useful in the treatment of the disease.

Thus, attempts to develop a pasteurellosis vaccine to date have centered on identifying the leukotoxin, or identifying antigens from protein extraction of the *P. haemolytica* cell itself, rather than identifying antigenic elements present in cell-free supernatants. However, the present invention, rather than focusing primarily on the leukotoxin, embodies the realization that cell-free supernatants contain numerous antigens—antigens which are necessarily absent or only minimally represented in *P. haemolytica* bacterins—which should serve to induce a more effective immunization, or serve to complement, and thereby improve, bacteria preparations. Moreover, the present invention embodies the further realization that effective *P. haemolytica* antigens should be identified using antisera obtained from naturally-infected, active or convalescent, cattle. The ultimate goal, therefore, is to achieve an antigenic composition which comprises a mixture or admixture of individual, relatively purified, *P. haemolytica* antigens which correspond, at least in terms of antigenic determinants, to antigens identified by antibodies present in naturally-infected antisera.

The present invention is thus directed in general to improved methods for identifying useful *P. haemolytica* antigens, one of which utilizes antisera from naturally-infected cattle to select antigens from cell-free *P. haemolytica* culture supernatants, and the other employing recombinant DNA technology to provide novel recombinant cells which are selected based on their ability to produce individual *P. haemolytica* antigens as identified by the antisera.

SUMMARY OF THE INVENTION

Accordingly, the present invention in its most general scope is directed to the identification and isolation of antigenic *P. haemolytica* polypeptides which may be employed, alone or in combination with each other, in the formulation of compositions for the treatment and/or prevention of pasteurellosis. The identification and isolation of antigenic polypeptides is achieved in two distinct fashions—by isolation of antisera-reactive antigenic proteins from cell-free *P. haemolytica* supernatants or through the use of recombinant DNA technology to construct recombinant cells which express individual *P. haemolytica* antigens. However, both approaches are related in that both employ antisera, from active or convalescent pasteurellosis-infected cattle to identify antigens for immunogen formulation.

The first approach involves the identification of antigenic *P. haemolytica* polypeptides present in a cell-free *P. haemolytica* culture supernatant. The use of such culture supernatants in the identification of the antigens is believed to be particularly important to the successful practice of the present invention in that culture supernatants are enriched in those proteins which are released by the organism ("extracellular" proteins) as opposed to those proteins which are retained within the organism, or expressed only on its surface ("intracellular" proteins). Thus, culture supernatant proteins are believed by the present inventors to correspond to those proteins which are released from the bacteria during active *P. haemolytica* infections and are more likely to include, for example, leukotoxin components thought to be involved in the breakdown of immunosurveillance in infected cattle, or other components not present in bacterins.

The supernatant approach to antigen isolation involves first culturing *P. haemolytica* bacteria to produce a culture supernatant which includes individual *P. haemolytica* polypeptides. After removing the *P. haemolytica* cells from the culture supernatant, the resultant cell-free supernatant is either employed directly or subjected to one of various molecular weight fractionation techniques known in the art, to fractionate the released *P. haemolytica* polypeptides according to their molecular weight. In one embodiment, SDS polyacrylamide gel electrophoresis is employed to separate supernatant proteins according to their molecular weights for further identification, characterization and purification.

For preparative separations, preparative gel electrophoresis is recommended in that it has been determined that gel electrophoresis provides the best separating capability for separating the antigens identified in accordance with the present invention. However, other separating techniques may be employed, for example, gel exclusion chromatography, density gradient centrifugation, ion-exchange resins or high pressure liquid chromatography. Under specified gel exclusion chromatography of supernatant proteins reveals a highly immunoreactive protein complex in the exclusion volume. While this complex may be employed directly in the formation of compositions, it may be also employed as an initial step in the further purification supernatant antigens.

The next step includes identifying antigenic polypeptides by ascertaining which of the extracellular (i.e.—supernatant) peptides are recognized by antisera obtained from cattle which have manifested discrete symptoms of the disease (e.g.—sniffling and wheezing, respiration distress, cough, fever, nasal discharge). Polypeptides which are shown to react with sera from infected cattle have been found not to react with "non-responder" control sera (i.e.—sera from non-infected cattle). This finding ensures that such peptides are, in fact, Pasteurella antigens which are being specifically recognized by pasteurellosis-induced antibodies.

The specific technique employed by the present inventors to identify the *P. haemolytica* antigens is immunoblotting. Immunoblotting is a technique which involves protein molecular weight fractionation, typically by polyacrylamide gel electrophoresis, transferring the fractionated proteins onto a nitrocellulose sheet, or other suitable adsorption matrix, and subjecting the sheet to a solution which includes the antisera under conditions which will allow for the formation of specific imunocomplexes between the Pasteurella-directed immunoglobulins present in the antisera and antigens which have been adsorbed onto the sheet. The immunoreactive polypeptides may then be visualized through the use of a label, for example, in the form of a radioactive or enzymatic label which has been attached to immunoglobulin molecules present in the sera, or to second antibody molecules which are specific for the sera. By comparing the gel migration distance of reactive peptides versus known standards, the molecular weight of the reactive peptides is ascertained.

Although the present invention is disclosed in terms of the immunoblot technique, it will be recognized by those of skill in the art that numerous other techniques for identifying Pasteurella antigens may be successfully employed. Culture supernatant proteins may be fractionated according to their molecular weight by any suitable technique. For example, column fractionation or density gradient centrifugation, as noted above, may be employed wherein antigen identification is achieved by reacting column or gradient fractions with the immune sera, for example, through use of ELISA or radioimmunoassay techniques.

After identification of the antigenic peptides, these peptides are then selected for isolation where desired.

Isolation from polyacrylamide gels is achieved by excising the gel regions identified as containing the appropriate proteins, and eluting the proteins from the gel, preferably by electroelution. Alternatively, where column or gradient fractionation is employed, the protein fractions which exhibit the immunoreactivity are selected and individually pooled.

Although preferred, there is no general requirement that the antigens be provided in their most purified, gel-isolated, state. The antigens may be provided either directly in the form of a purified culture supernatant (i.e.—purified to remove small molecular weight and dialyzable contaminants, salts, etc.), or through further supernatant purification schemes directed at partial purification by removing non-antigenic proteins, while substantially retaining the antigens. Gel exclusion chromatography is one such technique which provides a relatively purified antigenic compositions, found to include most if not all of the dominant antigenic supernatant species.

An alternative approach which may be employed in the identification and isolation of supernatant antigens involves preparing an immunoaffinity chromatography substrate using immune sera from pasteurellosis-infected cattle, and using the antibody-substrate to selectively purify the antigenic peptides. More particularly, immune sera from Pasteurella-infected cows is first attached to a substrate such as CNBr-Sepharose. The antisera-bound Sepharose is then poured into a column and washed with a suitable wash buffer. An aqueous mixture which includes the supernatant antigens is then passed over the column under conditions which allow for immunocomplex formation between the antigens in the mixture and the Sepharose-bound antibodies. After the column is washed extensively to remove non-specifically bound material, the specifically-bound antigens are then eluted from the column. This Pasteurella-specific antigen mixture may then be employed directly or size fractionated to further purify the individual antigens which may be identified in accordance with the present disclosure.

By practicing one of the. foregoing cell-free supernatant-directed methods, one may obtain a composition which includes one or more substantially purified *P. haemolytica* antigens which are secreted by the *P. haemolytica* cell, isolatable from a cell-free *P. haemolytica* culture supernatant and have binding affinity for immune sera obtained from a pasteurellosis infected cow. Such compositions may be identified as including antigens which are characterized according to apparent molecular weight ranges which they exhibit upon SDS polyacrylamide gel electrophoresis and immunoblot analysis.

Molecular weight assignments are approximated by correlating the SDS gel migration of antigens to the migration of proteins of known molecular weights. Thus, differences in techniques for measuring migration distances will result in differences in apparent molecular weights. These differences are naturally accentuated by the fact that SDS polyacrylamide gel electrophoresis is an inherently less accurate means of determining the molecular weight of larger proteins. Moreover, some antigens have been found to exhibit broader banding patterns upon SDS gel electrophoresis, perhaps due to varying degrees of protein modifications, for example, glycosylation.

In particular, compositions are characterized as including at least one of seven antigen groups, referred to as supernatant antigens I–VI, wherein the antigens exhibit molecular weight ranges as follows:

| Antigen Group | Apparent Molecular Weight Range | Reference Weight |
|---|---|---|
| I | 98–140K | 105K |
| II | 86–110K | 90K |
| III | 76–85K | 76K |
| IV | 73–82K | 73K |
| V | 63–71K | 65K |
| VI | 42.5–45K | 43K |
| VIIa | | 35K |
| b | 29–35K | 32K |
| c | | 29K |

The "reference weight" above refers to the weight which represents the inventors best estimate of a specific molecular weight. As such, the particular antigen groups may at times be referred to, for convenience, in terms of either the reference weight or the antigen group designation. Such references should not be interpreted to limit the scope of the present invention to any such specific reference molecular weight and is meant to include the range as a whole.

It will also be appreciated that antigen group VII includes antigens of three separate molecular weight ranges. It has been found that all infective *P. haemolytica* strains studied to date exhibit at least one, but generally not more than one, of these group VII antigens. Thus, it is hypothesized that these antigens are related, perhaps differing in terms of glycosylation, amino acid sequence or other modifications. Hence, based on this hypothesis, these antigens have been grouped together as a single antigen group VII.

The individual reactive antigen groups, in the form of proteins, protein fractions or mixtures, may thus be used to provide a composition which is suitable for use as either a vaccine, or as an inoculum to generate antisera for use in, for example, providing passive immunity to high-risk cattle. Moreover, antibody compositions, derived from such antisera or generated through hybridoma technology, may be used to diagnose pasteurellosis by using them to detect Pasteurella antigens in biological fluids in the cow being tested.

As referred to above, a second general overall approach employed by the present inventors to identify *P. haemolytica* antigens involves the use of recombinant DNA technology. In this embodiment, recombinant cells are provided which have been genetically engineered to individually express individual *P. haemolytica* antigens. Typically, such recombinant cells include *E. coli* cells which have been transformed with an appropriate recombinant cloning vector. The individual *P. haemolytica* antigens are thus coded for by *P. haemolytica* DNA fragments which have been ligated to the cloning vector. The recombinant cell thereby expresses the antigen by expressing the protein coding sequences contained within the vector-ligated DNA fragments.

In particular, recombinant cells made in accordance with the present invention have been genetically engineered by a process which includes the steps of fragmenting *P. haemolytica* DNA; ligating the fragmented DNA to a cloning vehicle, suitable for transforming a selected cell type, to produce a recombined cloning vehicle; transforming the cell type with the recombined cloning vehicle to produce transformed recombinant cells; selecting a clonal colony of the transformed recombinant cells which produces an individual *P. haemolytica* antigen; and culturing the selected clonal colony to provide the recombinant cell.

Fragmentation of the *P. haemolytica* DNA is employed in order to provide DNA fragments of a site range compatible with the particular cloning vector employed. For example, for most plasmids which are currently used in the art, a size range of 1–15 kilobases is preferred. With fragment sizes greater than 15 kilobases, recombinant plasmids are apparently destabilized. Bacteriophage vectors may accommodate much larger fragment sizes, up to somewhat greater then 20 kilobase insertions, but generally require a lower size limit of at least about 5 kilobases. The size range limitations for phage is generally dictated by their ability to be successfully "packaged" by phage coat proteins. Cosmids, a third general type of vector which may be employed, are composed of both phage and plasmid genetic elements and will generally accept size ranges of from 5 to about 40 kilobases.

In one embodiment, the *P. haemolytica* DNA is randomly fragmented through the use of partial restriction enzyme digestions. In that such digestions are "partial", relatively large DNA fragments may be obtained which contain full complements of genes. DNA fragments so-produced are "random" in that under "partial" restriction digestion conditions, not every enzyme recognition site is recognized and cleaved. The fact that a selected restriction enzyme recognition site may be present within, for example, a particular desired coding sequence does not limit the usefulness of "partial" enzyme digestion as a method for fragmenting the DNA because at least a proportion of the population of the DNA fragments will provide a full, uncleaved sequence of the particular gene. Thus, virtually any restriction enzyme may be employed for the generation of *P. haemolytica* DNA fragments in accordance with the present invention.

However, it will be appreciated that there is no general requirement that fragments be generated which contain entire coding sequences of a particular *P. haemolytica* antigen gene. All that is required is to obtain fragments which are sufficiently long to code for polypeptide sequences which are recognized by pasteurellosis-derived antisera. In that they are "recognized" by the immune sera, such polypeptides will at least contain the antigenic determinants ("epitopes") necessary to render such fragments antigenic and hence, such protein fragments may be successfully employed in vaccines or inoculums. For the purposes of the present invention, polypeptides which are derivations of full protein sequences, but which polypeptides nevertheless include antigenic determinants and are therefore functional in providing an immune response, are considered to be antigenic functional equivalents of the full protein sequences and are thus within the scope of the present invention.

Thus, the only limitation generally on the particular restriction enzyme employed for DNA fragmentation is that such enzyme should preferably be compatible with cloning sites present in the particular cloning vehicle employed.

In the present disclosure, the inventors have utilized two different types of cloning vehicles—an *E. coli* plasmid, pUC7, and a bacteriophage, EMBL4—both of which are capable of introducing a recombinant fragment into an *E. coli* cell in a manner wherein the introduced fragment can be transcribed by the transformed or transfected (as is the case with phage introduction) *E. coli* cell.

In both cases, the present inventors have chosen to utilize a Bam HI cloning site present in both the plasmid and bacteriophage DNA sequence. The recognition site for Bam HI, a six-base pair recognition enzyme, is compatible with the DNA ends generated by enzyme Sau 3A, a four-base pair recognition enzyme. Since Sau 3A has a four-base specificity, there will necessarily be more recognition sites for Sau 3A in any given DNA segment. Therefore, the use of Sau 3A, or other four-base pair specific enzymes, to generate "partially" restricted DNA will provide a greater randomization of DNA fragments. Thus, the use of four-base pair specific enzymes are preferred, and in particular, where a Bam HI cloning site is utilized, the use of Sau 3A is preferred due to the compatibility of Sau 3A-generated fragments with Bam HI sites.

In one embodiment, the present inventors have employed total Bam HI digestions of *P. haemolytica* DNA for cloning into the Bam HI site of EMBL4. The successful generation of recombinant cells which express individual *P. haemolytica* antigens demonstrates that total restriction digestions may also be employed where desired, at least where the enzyme employed has a 6-base pair specificity which can thus generate fragments which are sufficiently long to code for antigenic protein sequences. However, partial Sau 3A-restricted DNA has also been successfully employed in the context of EMBL4 to generate *P. haemolytica* clone banks.

Therefore, the present invention demonstrates the successful development of *P. haemolytica* DNA clone "banks" constructed in *E. coli*, using either a recombined *E. coli*-specific bacteriophage or plasmid. As referred to herein, a *P. haemolytica* clone "bank" is defined as a composition comprising a population or plurality of individually transformed (or transfected or infected as the case may be) recombinant cells, wherein the transformed or transfected population has been transformed or transfected with a recombinant vector which has individual *P. haemolytica* DNA fragments ligated thereto. As referred to herein, the term "transforming" shall be used to include other types of DNA introductions into cells and is meant to include, for example, transfection and infection.

As will be understood by those of skill in the art, such clone banks serve many useful purposes, for example, as a starting population for the selection of individual clones therefrom which clones provide individual *P. haemolytica* antigens and other proteins.

Selection of transformed *E. coli* cells from clone banks, which cells produce a selected *P. haemolytica* pasteurellosis-associated antigen, is achieved most preferably by, first, culturing cells from the unfractionated clone bank population on a solid support medium, for example, on agar-containing plates, in a manner to provide for the growth of separated, individual clonal colonies on the surface of the medium. One then typically fashions an imprint of the clonal colonies onto a suitable membrane support, for example, a nitrocellulose membrane, which membrane is then subjected to suitable immunoreaction with sera from a pasteurellosis-infected cow. Thus, clones which are positive for the production of Pasteurella antigens are selected by means of a label attached either to the reactive sera or to a second antibody which is specific for bovine sera.

Through practice of the foregoing recombinant techniques, the present inventors have identified two *P. haemolytica* antigens in addition to those antigens identified by supernatant fractionation. These cloned antigens have been identified as having molecular weights of approximately 66K and 53K Daltons, as ascertained by polyacrylamide gel electrophoresis and immunoblot analysis. It will be appreciated that the sizes of *P. haemolytica* proteins which are produced by recombinant *E. coli* may be different than corresponding proteins naturally produced by *P. haemolytica* itself. This may be due to differences in post-translational protein modification by the respective cells or, alternatively, may be the result of the cloning of a partial coding sequence which is an antigenic functional equivalent of the entire protein.

Therefore, the present invention is directed to compositions which include at least one of the eleven *P. haemolytica* antigens (i.e.—one of the seven supernatant protein groups I–VII or one of the two recombinant proteins), or antigenically functional equivalents thereof identified by the foregoing procedures, and further to pharmaceutical compositions which include a pharmaceutically acceptable excipient or adjuvant. Suitable pharmaceutical carriers include inert solid diluents or fillers, a sterile aqueous solution, various organic solvents, emulsifying or suspending agents, or aqueous diluents such as water, ethanol, propylene glycol, glycerin, or combinations thereof.

For parenteral administration, the antigens may be formulated in sesame or peanut oil, aqueous propylene glycol, or in sterile aqueous solutions. Such solutions are typically suitably buffered if necessary and the liquid diluent first rendered isotonic with sufficient saline or glucose. Additionally, stabilizers in the form of, for example, sorbitol or stabilized gelatin may be included. These particular aqueous solutions are particularly well suited for intramuscular and subcutaneous injection, as is generally preferred for vaccination using antigenic preparations.

However, to increase the potential antigenicity, and thereby improve the performance of antigen-containing pharmaceutical preparations, one may additionally desire to include various immunoadjuvants, such as the water-in-oil emulsion developed by Freund. The basic ingredients of light mineral oil (Bayol) and emulsifying agents mixtures such as Arlacel (A or C) are available commercially. The antigens are emulsified in either solutions or suspensions of the immunogen (incomplete Freund's adjuvant). Moreover, the addition of mycobacterium (*M. Butyricum, M. tuberculosis*) in small amounts to the suspension (complete Freund's adjuvant) leads to a further enhancement of the immunogenicity of the pharmaceutical vaccines made in accordance with the present invention.

In still further embodiments, the present invention is directed to antibody compositions, both polyclonal and monoclonal, having specificity for one or more of the eleven antigens identified by the practice of the present invention. In general terms, polyclonal antibodies having affinity for one of the selected *P. haemolytica* antigens are obtained by first immunizing an immunocompetent Mammal with the selected antigen to obtain an immune response by the mammal, obtaining immune serum from the immunized mammal, and fractionating the serum to provide the antibody. Alternatively, the mammal may be immunized with a less purified *P. haemolytica* protein preparation, for example, Pasteurella supernatants, and the desired specific antibody isolated from the resultant antibody mixture by, for example, adsorption to antigen-Sepharose columns by techniques known in the art.

Monoclonal antibodies to Pasteurella antigens may be obtained by the well-known technique of hybridoma development as detailed, for example, in U.S. Pat. No. 4,196,265, incorporated herein by reference. In general, the technique involves fusing spleen cells of a rodent with myeloma cells from the same rodent species, wherein the rodent providing the spleen cells has been immunized with the selected Pasteurella antigen; culturing the fused cells in a selective medium; testing for the presence of antibodies which are capable of immunocomplexing with the selected antigen; culturing cells producing antibodies which are capable of reacting with the selected antigen; and obtaining antibodies from the culture supernatant of the cells.

Accordingly, a method is additionally provided whereby passive immunity to *P. haemolytica* infection is conveyed to a cow by administering to the cow a composition which includes a therapeutically effective amount of antibodies having specificity for one or more of the Pasteurella antigens identified by the present invention. Thus, high-risk cattle, for example, cattle being shipped, may be administered *P. haemolytica*-specific antibody compositions in the form of immune globulins as a temporary prophylaxis to pasteurellosis, or as a treatment during early stages of the disease.

In further embodiments employing Pasteurella-directed antibody or antigen compositions, methods are provided for detecting the presence of such antigens or antibodies, as the case may be, in the serum of suspected infected cattle as a means of diagnosing the disease. In the case of antibody detection, the method includes obtaining a biologic sample suspected of containing antibodies, such as serum, blood, pleural fluid, or tissue samples, from the cow; contacting antibodies from the biologic sample with a selected antigen under conditions which will allow for the formation of specific antigen-antibody immunocomplexes; and detecting the formation of an antibody-antigen immune complex between the antibody and antigen, the formation of such a complex being indicative of the presence of the selected antibody in the sample. Preferably, the immunocomplex formation is detected by means of a label as is known in the art. For antigen detection, the general methodology is the same except that the biologic sample is contacted with an antibody-containing preparation.

Diagnostic kits for diagnosing Pasteurellosis in a cow are also provided wherein such kits include one or ore of the *P. haemolytica* antigens, or antibodies having pecificity therefor, together with a suitable immunoetection reagent, for example, a radioactive or enzymatic ligand attached to the antigen or antibody or to a second antibody having specificity for the first.

BRIEF DESCRIPTION OF THE DRAWINGS

FIG. 1. Immunogenic Pasteurella Supernatant Proteins. Immunoblot of fresh *P. haemolytica* cell-free supernatants separated on 7.5% SDS-polyacrylamide gel, electroblotted to nitrocellulose and probed with a 1/1000 dilution of convalescent bovine serum. Lanes: M, prestained molecular weight markers with sizes given in kilodaltons; 1, PHL101; 2, ATCC14003; 3, 194; 4, 195; 5, 199.

FIG. 2. Production of Supernatant-Specific Antibodies in a Steer Immunized with *P. haemolytica* Supernatant Proteins. Nitrocellulose strips carrying separated *P. haemolytica* supernatant proteins were probed with 1/1000 dilutions of bovine serum from the following sources: C, convalescent animal; FCS, fetal calf serum,: P1 and P2, preimmune test animal before immunization; 1 through 8, test animal one through eight weeks following immunization with samples being drawn weekly.

FIG. 3. Partial Separation of Supernatant Protein Antigens by Electroelution. *P. haemolytica* supernatant proteins were separated on a 7.5% SDS-polyacrylamide slab gel. The gel was cut into horizontal slices and proteins electroeluted from these slices as described. Eluted proteins were analyzed by SDS-PAGE and immunoblotting. Lanes: M, kilodaltons; S. *P. haemolytica* supernatant; 1, 80–100 kD slice; 2, 60–80 kD slice; 3, 40–60 kD slice. The immunoblot was probed with a 1/1000 dilution of convalescent bovine serum.

FIGS. 4A and 4B. Plasmid Clone pSH200 Encodes a 66 Kilodalton Pasteurella Antigen in *E. coli*. Immunoblots of *E. coli* and *P. haemolytica* whole cell lysates and a *P. haemolytica* supernatant preparation were probed with: (FIG. 4A) 1/1000 dilution of convalescent bovine serum, or (FIG. 4B) antigen eluted from *E. coli* cells carrying pSH200. Lanes: a, KK2186 (pUC7); b, KK2186 (pSH200); c, PHL101 whole cell lysate; d, PHL101 cell free supernatant; M. molecular weight markers with sizes shown in kilodaltons.

FIG. 5. Recombinant Bacteriophage Lambda SH-20 Encodes a 55 Kilodalton Antigen Recognized by Convalescent Bovine Serum. Immunoblot of phage lysates grown on *E. coli* NM538: V, vector EMBL4; 20, recombinant 20. Lane M contains prestained molecular weight markers with sizes shown in kilodaltons. The blot was probed with a 1/1000 dilution of convalescent bovine serum.

FIG. 6. Western blot analysis of antigens produced by recombinant lambda phages in *E. coli*. M, prestained protein molecular weight markers with sizes given in kilodaltons; 1, EMBL4; 2, lambda sh20; 3, lambda sh132; 4, lambda sh127; 5, *P. haemolytica* supernatant. Phage lysates containing $10^7$–$10^{10}$ pfu/ml were electrophoresed on SDS-polyacrylamide gels, the gels electroblotted to nitrocellulose and the blots probed with immune bovine serum. Lambda sh20, lambda sh127, and lambda sh132 are exemplary of the three types of recombinant phages that were detected by immunoscreening. Lambda sh127 is a member from the Bgl II library that produces the same 66 KD antigen as pSH200. Lambda SH20 (Bam HI library) encodes a 55 KD antigen, while the 105 kD antigen of lambda sh132 (Bgl II library) corresponds to supernatant antigen I.

Figure 7A:
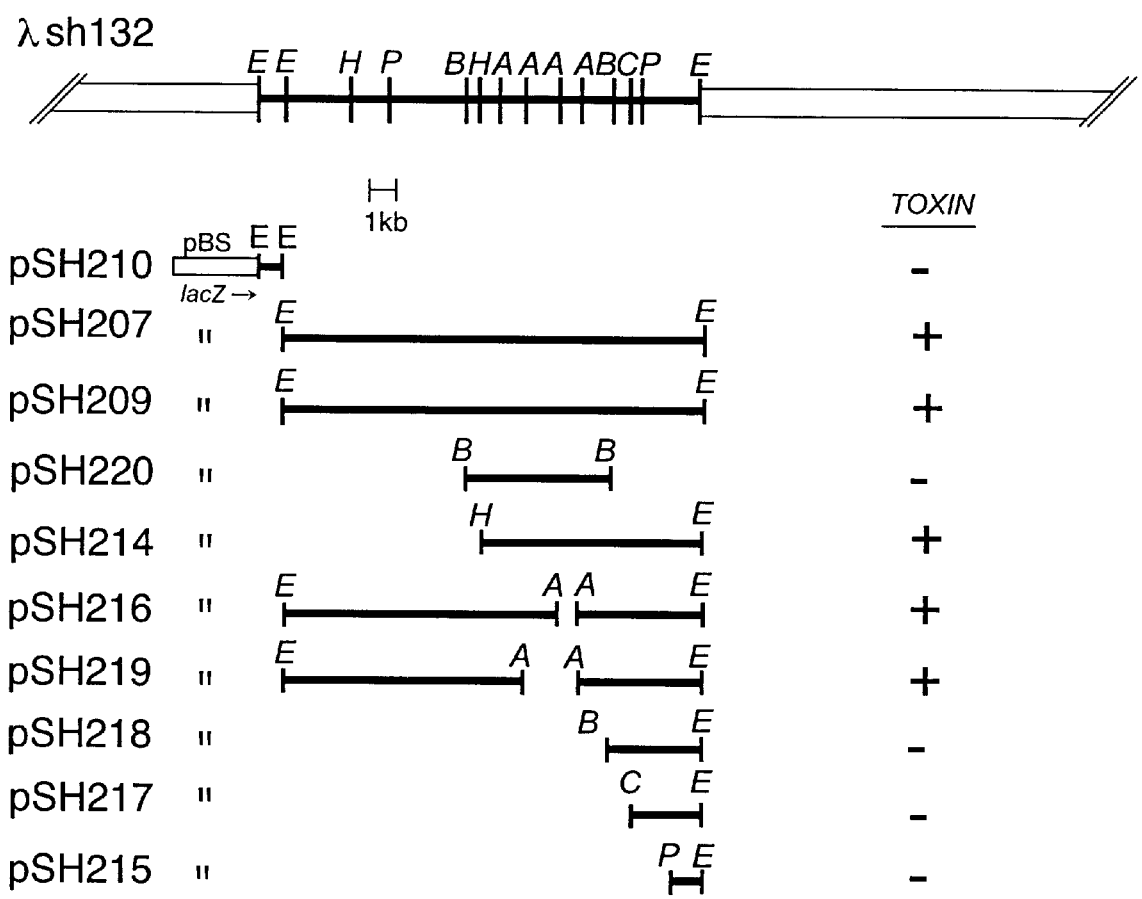
Figure 7B:
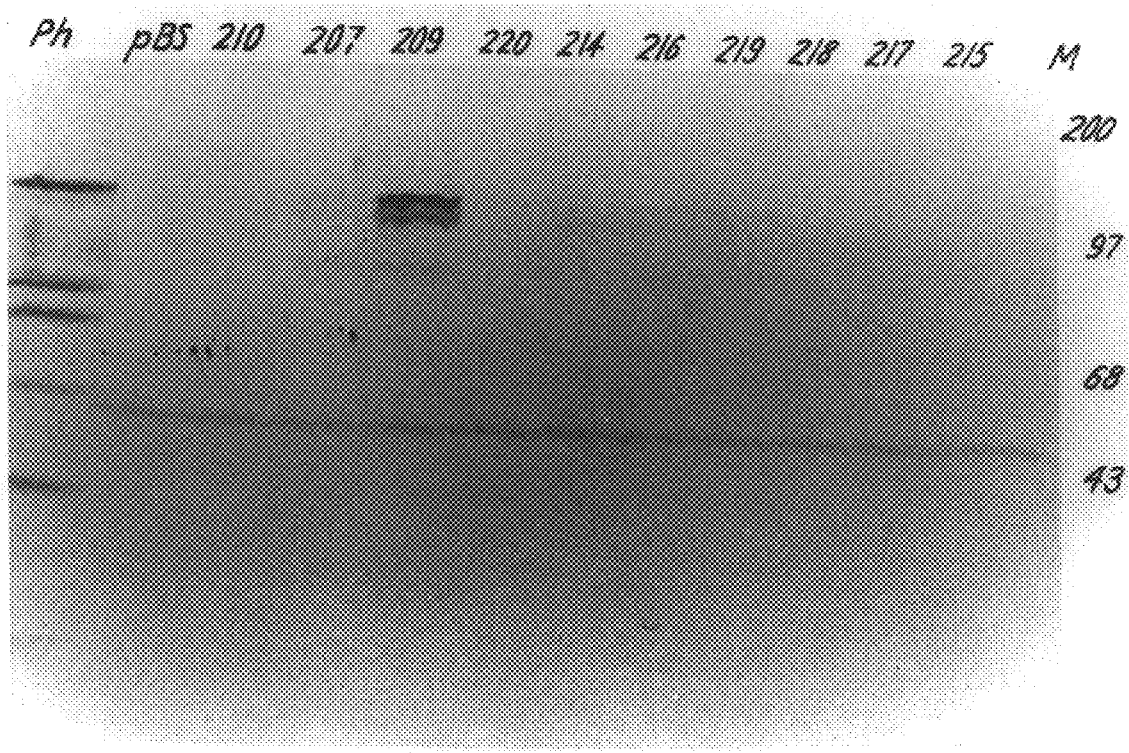

FIGS. 7A and 7B. Genetic and physical map of recombinant phase and plasmids containing the ptx gene. E, Eco RI; H, Hinc II; P. Pst I; B, Bgl II; A, Ava I; C, Cla I. Restriction enzyme mapping of lambda sh 132 indicated that the recombinant phage contained two BglII sites and suggested that the insert was derived from three chromosomal Bgl II fragments. The insert also contained a single Eco RI site. The two constituent Eco RI fragments (17.6 and 1.2 kb) were subcloned into the Eco RI site of the lacZ filamid, pBS, and the resulting plasmids, pSH207, pSH209 and pSH210, were tested for their ability to produce the 105 kD antigen. Strains carrying these and other deletant plasmids (FIG. 7A) were screened by Western blot analysis of whole cell E. coli lysates (FIG. 7B). Plasmids pSH207 and pSH209 produced the antigen but pSH210 did not. To further delimit the ptx gene, simple deletants and subclones were constructed from pSH207 and then tested for antigen production. These mapping experiments identified the 5.2 kb Ava I-Eco RI fragment as containing the ptx gene and also showed that the 3.9 and 6.4 kb Bgl II fragments of the phage insert were contiguous within the P. haemolytica chromosome.

Figure 8:
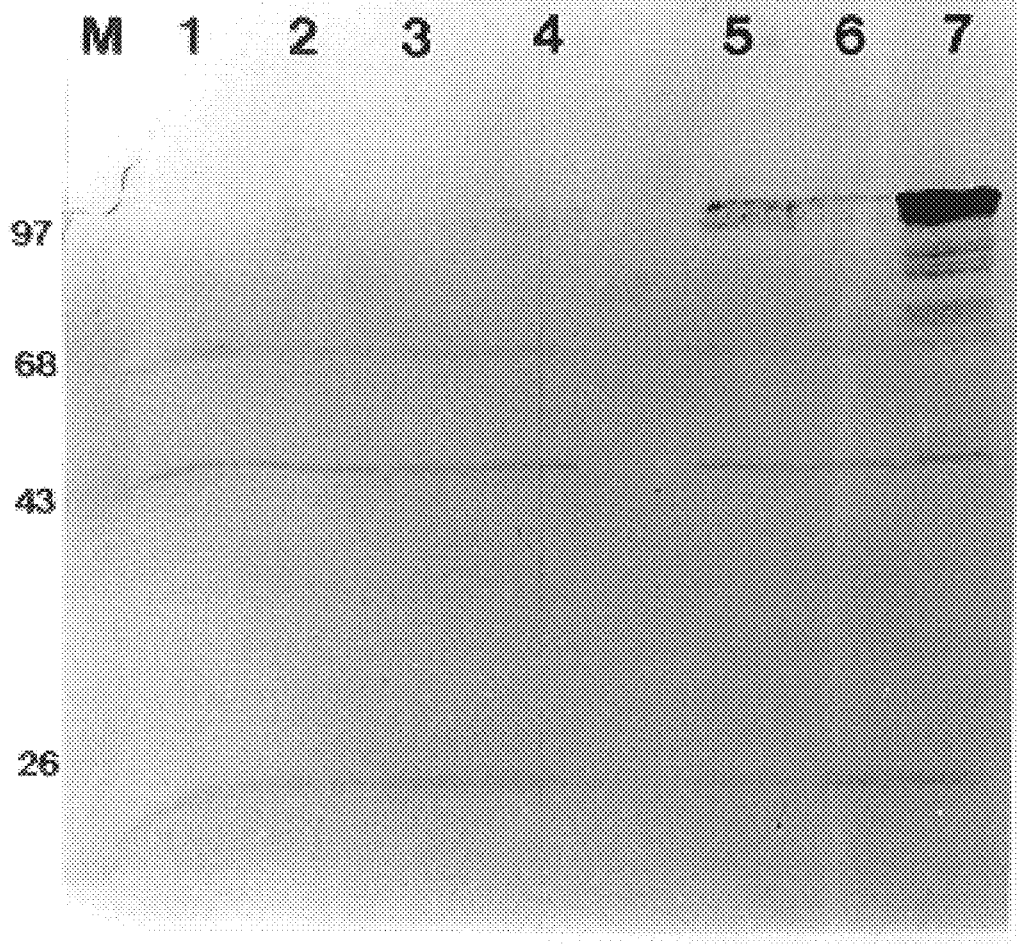
Figure 1:
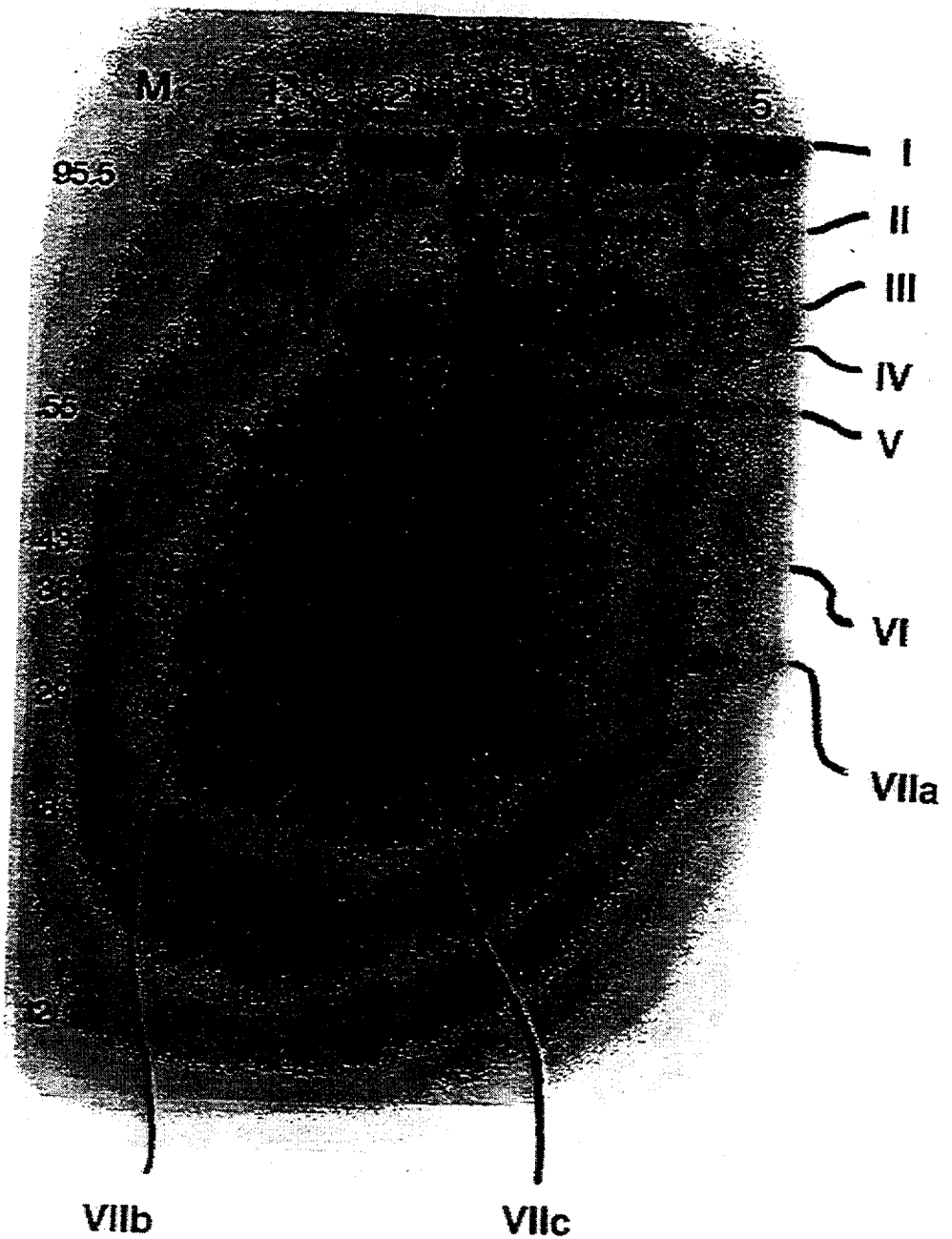
Figure 2:
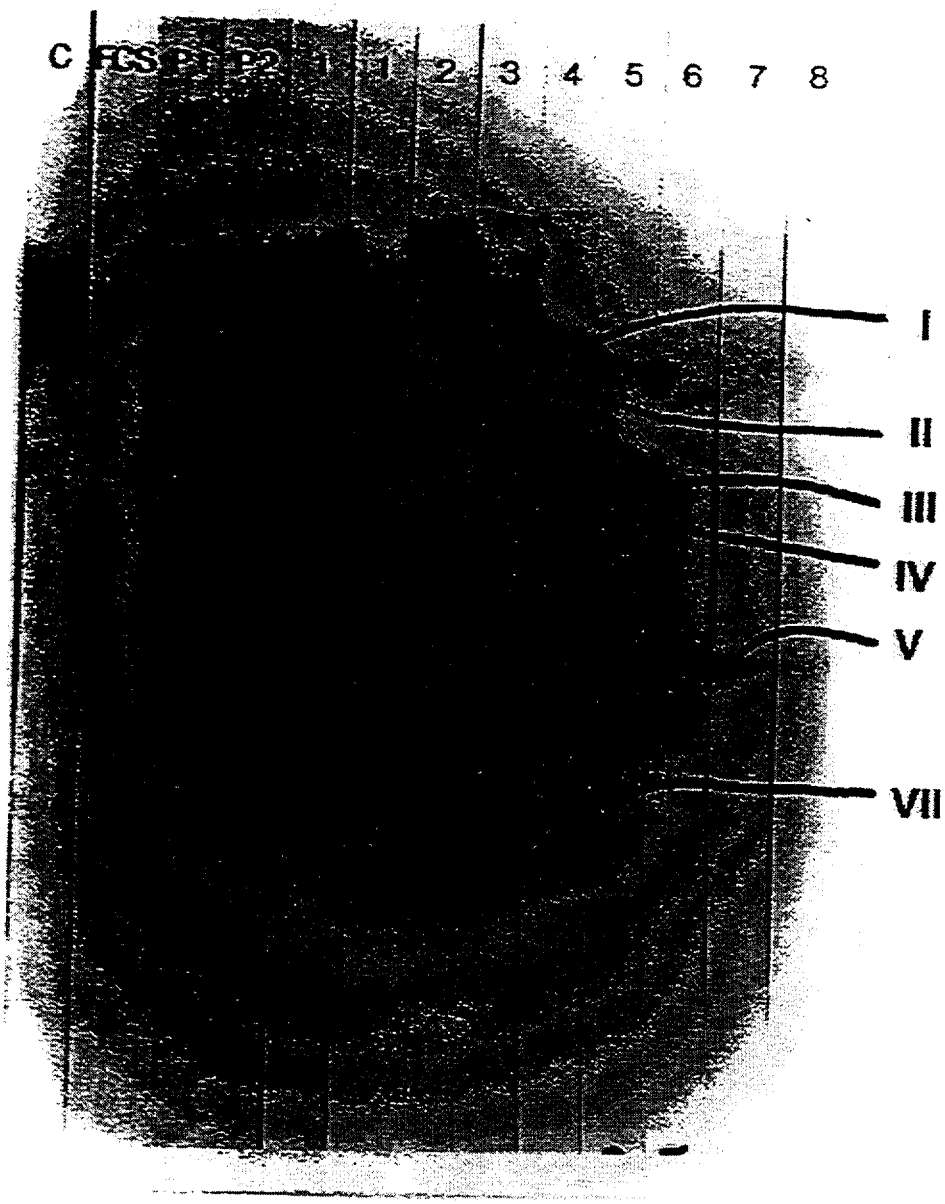
Figure 3:
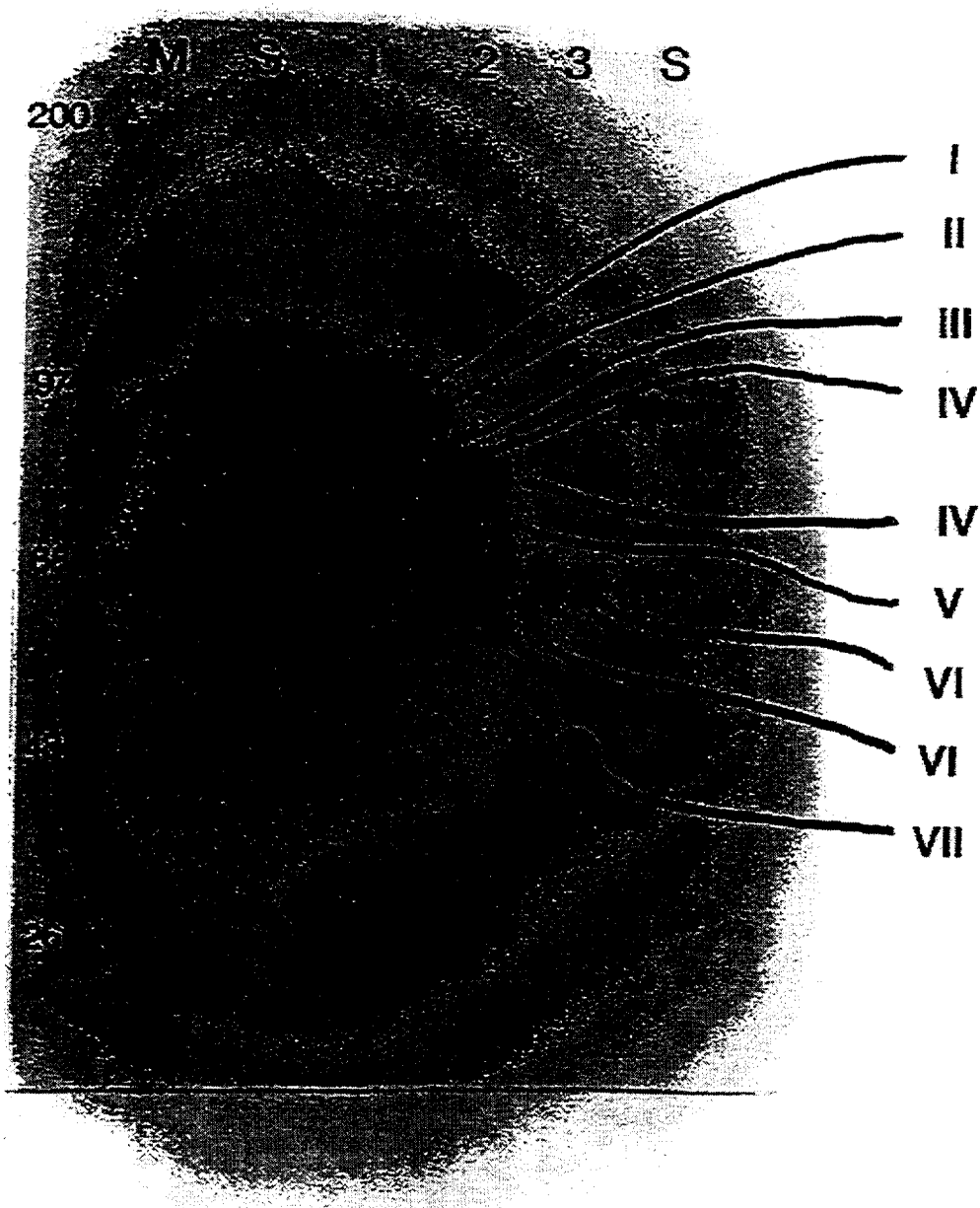
Figure 4A:
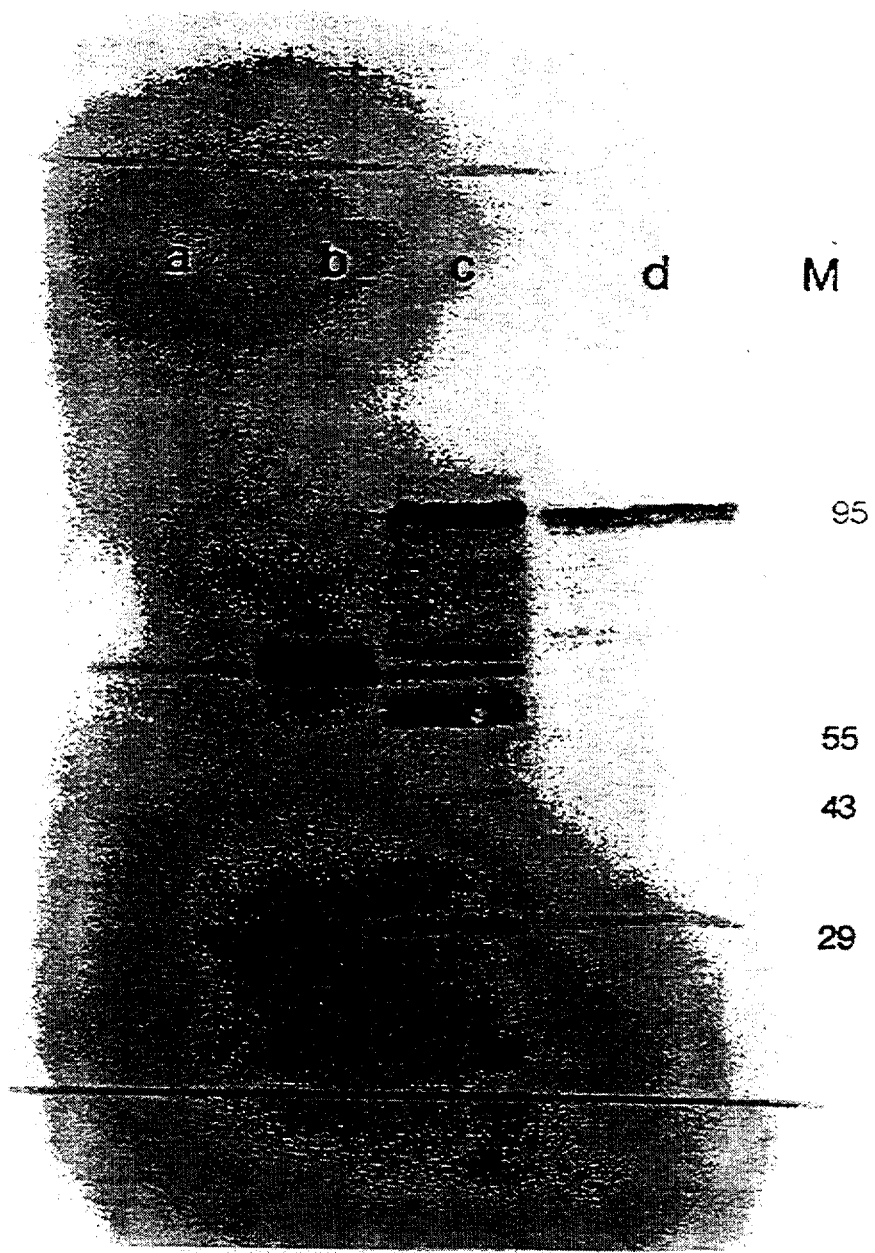
Figure 4B:
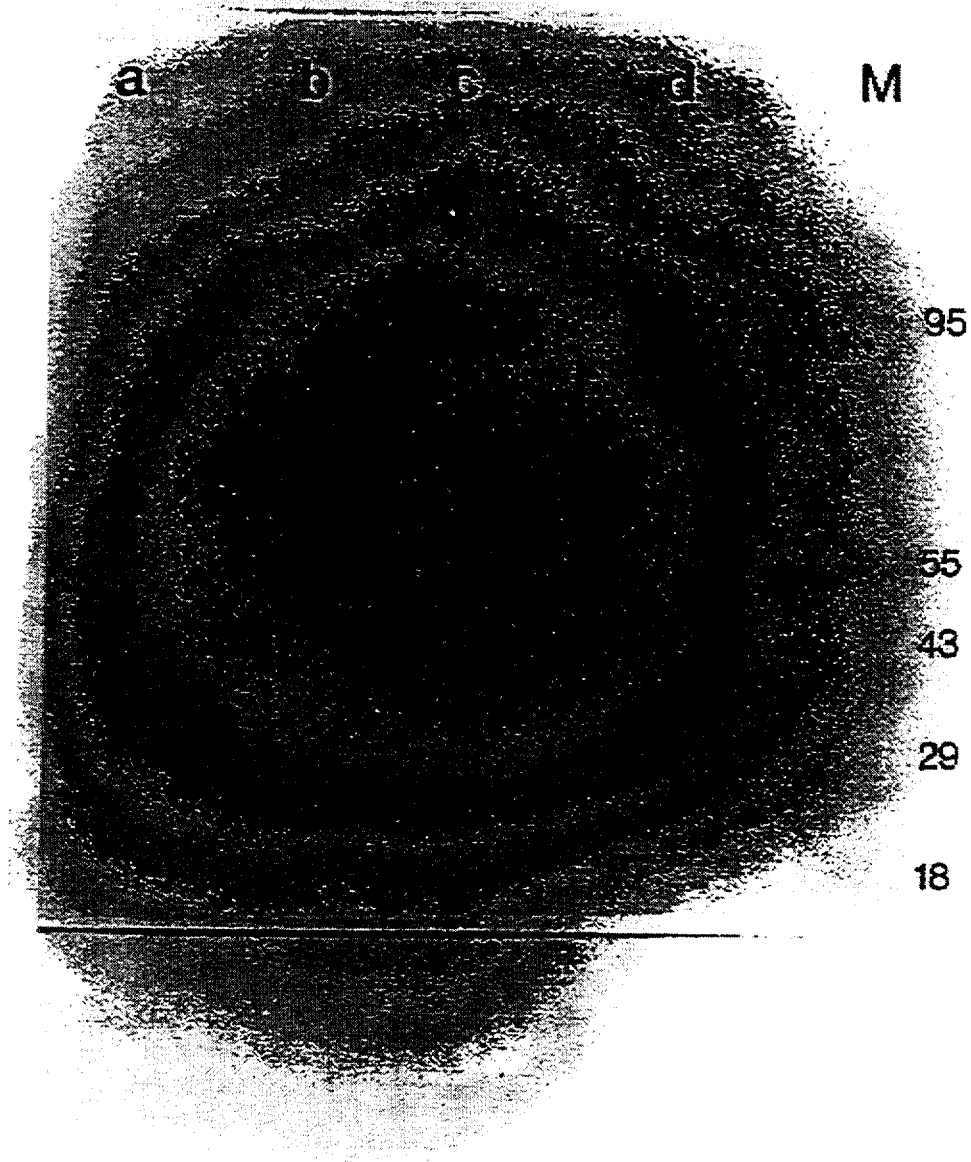
Figure 5:
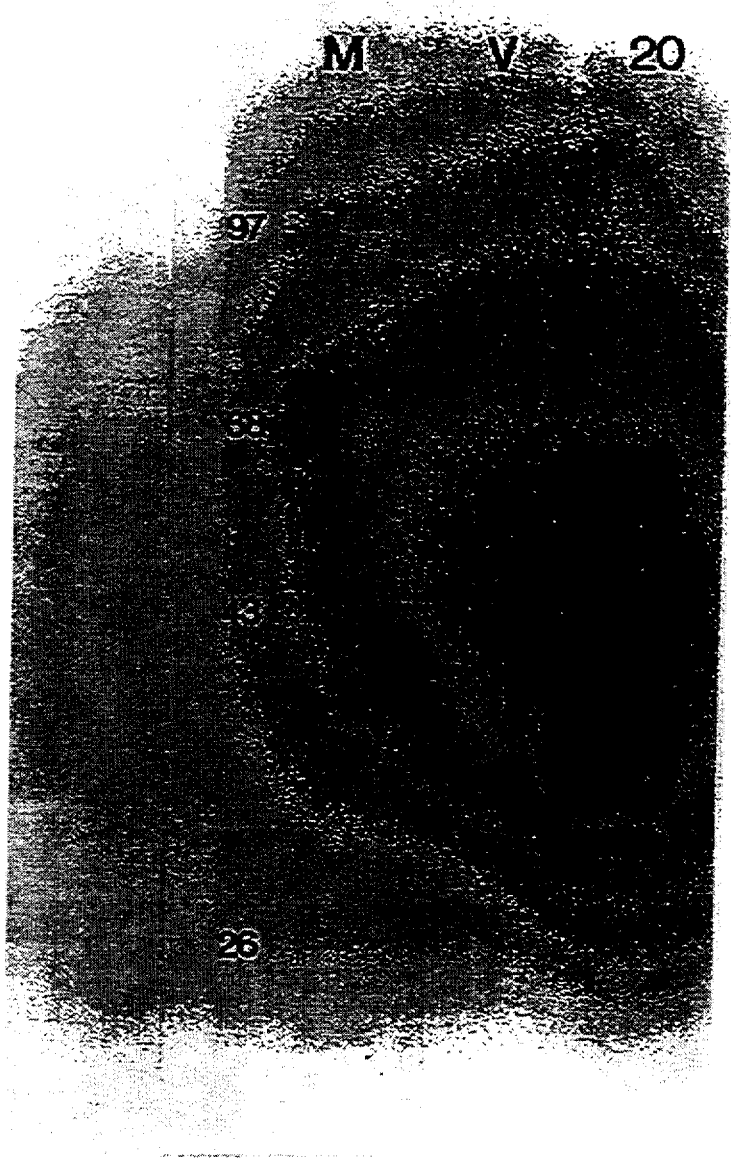
Figure 6:
Figure 7A:
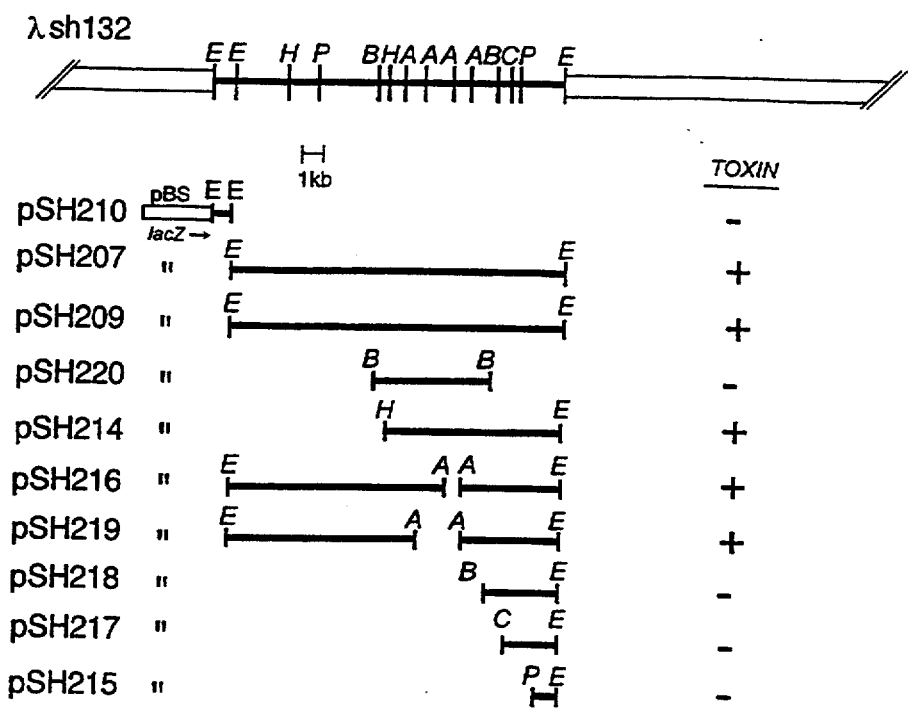
Figure 7B:
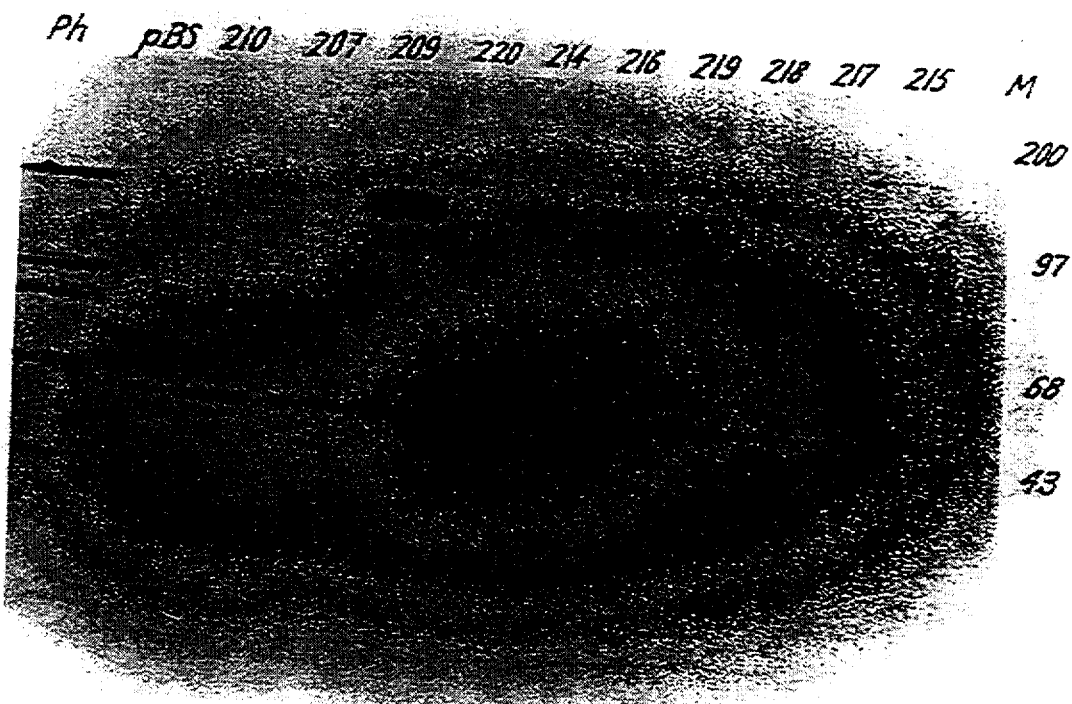
Figure 8:
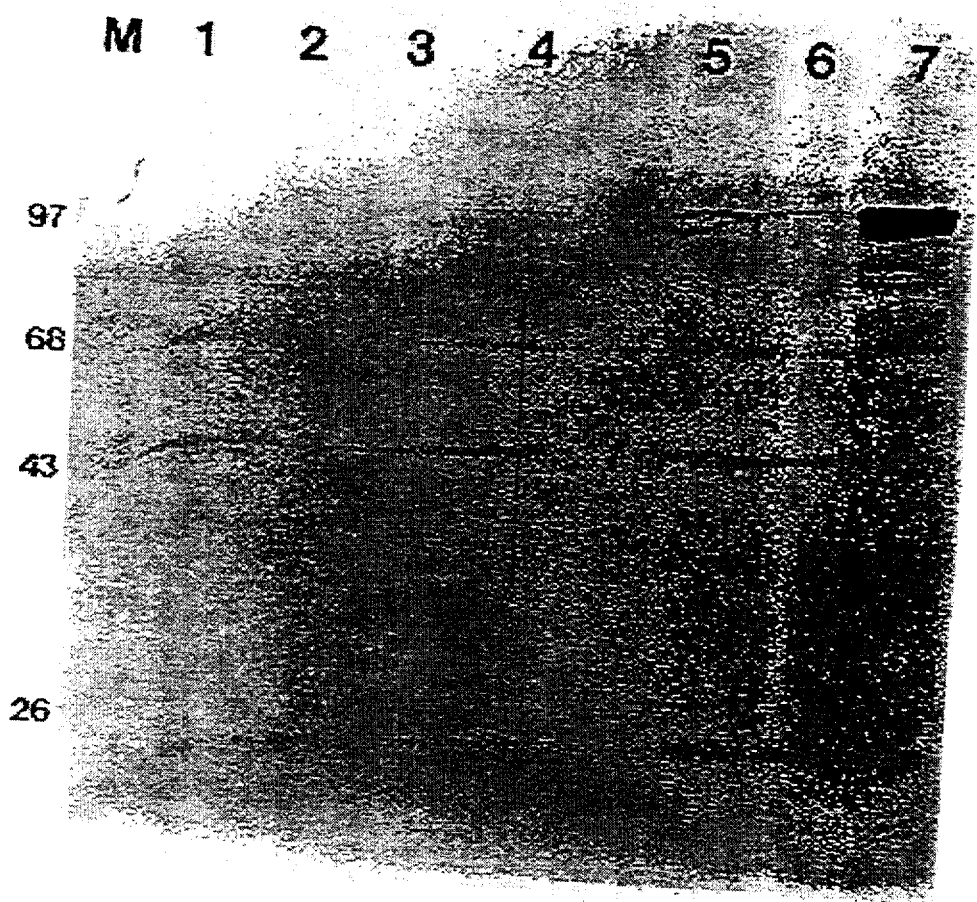

FIG. 8. Transcriptional frame of the ptx gene and overexpression of the PTX protein under lac transcriptional control. Comparison of the amount of 105 kD antigen produced by pSH207 and pSH209 (FIG. 7A and 7B) suggested that ptx expression was influenced by vector sequences, particularly by transcription from the lac promoter on pBS. This was verified by comparing the amount of antigen produced by each plasmid in the presence and absence of IPTG. Whole cell lysates were prepared and analyzed by Western blotting for pBS (lane 1), pSH207 (lanes 2, 3 and 4) and pSH209 (lanes 5, 6 and 7) from: 1, 2 and 5, overnight culture; 3 and 6, log-phase culture, uninduced; 4 and 7, log-phase culture, 3 hr. induction with 0.5 mM IPTG. M, prestained protein molecular weight markers with sizes shown in kilodaltons. The immunoblot illustrates that ptx expression from pSH209 is increased at least 10-fold in the presence of IPTG, while pSH207 expression is not affected by induction of the lac promoter. The production of antigen by pSH207 does, however, indicate that the Pasteurella ptx promoter is transcribed in *E. coli*, albeit at a comparatively low level.

FIGS. 9A–9L. The Nucleotide Sequence and Corresponding Amino Acids Sequence of the ptx Gene and the PTX Protein. Shown is the nucleotide sequence of the ptx gene and its encoded product, the 105K Dalton antigen or PTX protein. The nucleotide sequence was determined using single stranded templates from subclones in M13 and pBS vectors, and the T7 DNA polymerase, Sequenase kit of United States Biochemicals (Cleveland, Ohio). The sequence was then analyzed by subjecting it to the Pustell DNA Sequence Analysis Program of International Biotechnologies, Inc. (New Haven, Conn.).

DETAILED DESCRIPTION OF THE INVENTION

The present invention is disclosed in terms of the two general approaches employed by the inventors to identify and isolate *P. haemolytica* antigens which are recognized by immune sera from pasteurellosis-infected cattle. The first approach involves the isolation of antigens identified in *P. haemolytica* cell-free supernatants, which the second approach utilizes recombinant DNA technology to provide cells which produce individual *P. haemolytica* antigens.

The supernatant approach is based on the premise that *P. haemolytica* bacterins inoculation fails to provide an effective immunization against pasteurellosis because such bacterins do not contain all of the antigenic elements necessary to provoke an appropriate immune response. It is believed that antigenic elements present in cell-free supernatants can serve to supply those elements which are missing from bacterin preparations. The fact that there are proteins present in the supernatant which are recognized by pasteurellosis-derived antisera demonstrates that the supernatant proteins identified by the present inventors are in fact present during active infections and are immunogenic. Moreover, it is known that cell-free supernatants contain the leukotoxin activity. Therefore, a key feature of the present invention is the use of *P. haemolytica* cell-free supernatants as a source of antigens which may be employed alone, or together with *P. haemolytica* bacterins, to immunize cattle.

A. Identification of *P. haemolytica* Supernatant Antigens

As noted above, the supernatant approach involves the identification of antigenic *P. haemolytica* polypeptides present in a cell-free *P. haemolytica* culture supernatant. In general, this approach involves, first, culturing *P. haemolytica* bacteria to produce a culture supernatant which includes individual *P. haemolytica* polypeptides. After removing the cells from the culture supernatant, for example, by centrifuging out the cells and pouring off the supernatant, the resultant cell-free supernatant is subjected to polyacrylamide gel electrophoresis to fractionate the proteins according to their molecular weights.

Next, the antigens of the present invention are identified by their ability to be recognized by antisera from pasteurellosis-infected cattle. Typically, and most conveniently, such identification is accomplished by immunoblotting which involves transferring gel-fractionated polypeptides onto a nitrocellulose sheet, and subjecting the protein-imprinted sheet to immuno-reaction with Pasteurella-induced antisera. The antigens of the present invention may then be identified by means of a label associated with antibody molecules of the antisera or with a second antibody, which label serves to identify the gel migration distance, and hence, the molecular weight, of the antigens. The following example, Example I, demonstrates the foregoing general embodiment in more specific terms as practiced by the inventors.

EXAMPLE I

Isolation of *P. haemolytica* Supernatant Antigens

1. Bacterial Strains, Media, and Bovine Sera. *Pasterurella haemolytica* strain PHL101 was obtained from Dr. G. H. Frank (USDA, Ames, Iowa). Strain ATCC 14003 was obtained from the American Type Culture Collection (Rockville, Md.). Other *P. haemolytica* strains were isolated from the lungs of cattle exhibiting symptoms of pasteurellosis.

Pasteurella strains were routinely cultivated on Blood Agar Base containing 5% sheep blood (Scott Laboratories, Fiskeville, R.I.) and were grown in Brain Heart Infusion (BHI) broth (Difco Laboratories, Detroit, Mich.) or RPMI 1640 medium (Sigma, St. Louis, Mo.) at 37° C.

Bovine sera used for immunodetection were isolated from whole blood samples drawn from adult animals and calves.

Only cattle which exhibited discrete symptoms, such as sniffling, wheezing, respiratory distress, cough, fever and nasal drainage, were selected as antisera donors. Also, it was found that cattle convalescing from the disease served as good sources for Pasteurella-reactive antisera.

2. Preparation of Whole Cell Lysates and Cell-Free Supernatants for Protein Analysis.

Cells were grown to a density of about $10^8$ to $10^9$ cells/ml in BHI and then harvested by centrifugation 10 minutes at 12,000×g. For whole cell lysates, the cell pellet was resuspended in a 1/14th volume of 2× SDS gel loading buffer (125 mM Tris, pH 6.8, 20% glycerol, 10% B-mercaptoethanol, 4.5% SDS, 0.005% bromophenol blue) and boiled 5 minutes before use (see, e.g., Silhavy, et al., *Experiments with Gene Fusions*, Cold Spring Harbor, 1984). Cell-free supernatants were prepared from the BHI supernatant or from a similar supernatant derived from cells that had been diluted 1/10 in RPMI 1640 and then grown to $10^9$ cells/ml. In either case, the supernatant was passed through a sterile 0.22 um filter and the filtrate used or stored frozen for further analysis.

Frequently, culture supernatants were concentrated with polyethylene glycol 6000 (PEG), as follows. The filtered supernatant was enclosed in dialysis tubing (exclusion limit 15,000 daltons), then was completely covered with PEG, and allowed to stand overnight at 4° C. The concentrated supernatant was removed from the dialysis tubing, transferred to clean tubing and then dialyzed 16 to 24 hours, at 4° C., versus 100 volumes 10 mM Tris, pH 7.5. Following dialysis, the concentrate was lyophilized and the protein resuspended in 10 mM Tris at 0.01× the starting volume.

3. Immunodetection of Proteins.

Whole cell lysates and cell-free supernatants were electrophoresed on 7.5% running, 3% stacking sodium dodecyl sulfate (SDS)/polyacrylamide gels as described by Laemmli (1970), *Nature*, 227:680. Supernatant samples were mixed with a 1/3 volume of 3× SDS gel loading buffer (2× described previously), and all samples were boiled five minutes before being loaded onto a gel. For direct visualization of proteins, gels were stained either with Coumassie brilliant blue (Laemmli, supra.) or with silver stain reagents (Merril, et al. (1981), *Science*, 211:1437) as directed by the supplier (BioRad, Richmond, Calif.).

Protein antigens recognized by immune bovine serum were detected in SDS/polyacrylamide gels using the western blotting technique of Towbin, et al. (1979), *Proc. Natl. Acad. Sci., U.S.A.*, 76:4350, and as follows. After electrophoresis, a 7.5% SDS/polyacrylamide gel was soaked for 60 minutes at room temperature in 200 ml 1× Electroblot Buffer (25 mM Tris, pH 8.3, 192 mM glycine) containing 4M urea, 2 mM Na$_2$EDTA, and 0.1 mM dithiothreitol (DTT). The gel was rinsed twice with fresh Electroblot Buffer, placed onto a sheet of 0.45 um nitrocellulose (Schleicher and Schuell, Keene, N.H.), and then sandwiched between several sheet of Whatman 3 MM filter paper. The entire assembly was placed between blotting electrodes, with the nitrocellulose sheet facing the anode, and lowered into a chamber containing precooled 1× Electroblot Buffer. A current of 0.02 amperes was applied for 16 to 20 hours at 4° C., causing the proteins to be transferred from the gel onto the nitrocellulose sheet.

The nitrocellulose sheet, or blot, was preincubated for 60 minutes at 37° C. in 100 ml 1× TBS (10 mM Tris, pH 7.6, 0.9% NaCl) containing 2% w/v nonfat dry milk to reduce non-specific binding of antibodies to the sheet.

Bovine serum was then added (usually to yield a 0.002 to 0.001 dilution) and the incubation was continued for 2 hours at 37° C. The blot was then washed five times in 100 ml 1× TBS for a total of 30 minutes to remove any unbound antibody.

Immune complexes were detected using biotin conjugated goat anti-bovine IgG and horseradish peroxidase (HRP) conjugated steptavidin (Kirkegaard and Perry Laboratories, Inc., Gaithersburg, Md.), (Guesdon, et al., (1979), *J. Histochem. Cytochem.*, 27:1131): the blot was incubated for 2 hours in 100 ml 1× TBS, 2% milk containing 0.1 mg biotin-anti-bovine IgG at 37° C., washed five times in 100 ml 1× TBS for thirty minutes, then incubated 60 minutes at 37° with 100 ml 1× TBS, 2% milk containing 0.05 mg HRP-streptavidin, and washed again five times. Bound HRP was detected by incubating the nitrocellulose blot with 100 ml 50 mM Tris, pH 7.5, 0.2M NaCl containing 60 ul hydrogen peroxide (30% solution) and 0.5 mg of the chromogenic substrate, 4-chloro-1-napthol (Hawkes, et al., 1982). Color development was complete within thirty minutes at room temperature.

FIG. 1 is illustrative of a typical immunoblot of various *P. haemolytica* strains. Demonstrated in the figure are various *P. haemolytica* supernatants which have been first subjected to SDS-polyacrylamide gel fractionation on a 7.5% gel. After electrophoresis and electroblotting as described above, the resultant blot was probed with a 1/1000 dilution of convalescent bovine serum. Prestained molecular weight markers were run in lane M, from which the molecular weights, in kilodaltons, were assigned and placed along the left-hand side of the figure. Cell-free supernatant proteins from various *P. haemolytica* strains were run on the gel as follows: lane 1, PHL101; lane 2, ATCC 14003; lanes 3–5, various other strains also isolated from naturally-infected cattle (strains 194, 195, and 199, respectively).

A semi-logarithmic plot of standard marker migration versus their known molecular weights was constructed. By comparing the migration of the various antigens to the molecular weight plot in this and numerous similarly performed experiments, molecular weight ranges have been assigned to the individual antigens, or antigen groups. The following table, Table I, is a compilation of those findings:

TABLE I

Molecular Weights of *P. haemolytica* Antigens

| Antigen Group | Apparent Molecular Weight Range | Reference Weight |
|---|---|---|
| I | 98–140K | 105K |
| II | 86–110K | 90K |
| III | 76–85K | 76K |
| IV | 73–82K | 73K |
| V | 63–71K | 65K |
| VI | 42.5–45K | 43K |
| VIIa | | 35K |
| b | 29–35K | 32K |
| c | | 29K |

Thus, referring to FIG. 1 in particular, there can be seen a series of *P. haemolytica* antigens, or antigen groups, which have migrated to a position which corresponds generally to their approximate molecular weights. Antigen I was found to exhibit an apparent molecular weight range of between 98 and 140 kilodaltons, with a reference weight of about 105 kilodaltons. The "bowing-out" labeling and intensity of the protein banding configuration of Antigen I suggested that it is present in relatively higher concentrations in the Pasteurella supernatants, and that the protein(s) is particularly antigenic.

A second antigen, Antigen II, migrated to a position corresponding to about 86–110 kilodaltons, with a reference weight of about 90 kilodaltons.

A third antigen, Antigen III, migrated to a position corresponding to about 76 to 85 kilodaltons, with a reference weight of approximately 76 kilodaltons.

A fourth antigen, Antigen IV, migrated to a position corresponding to about 73 to 82 kilodaltons, with a reference weight of about 73 kilodaltons. Thus, Antigens III and IV appear generally as a distinctive doublet, with Antigen III running slightly behind Antigen IV.

A fifth antigen, Antigen V, migrated to a position corresponding to about 63 to 71 kilodaltons, with a reference molecular weight of about 65 kilodaltons.

A sixth antigen migrated to a position correspond to about 42.5 to 45 kilodaltons, with a reference molecular weight of about 43 kilodaltons.

Three additional antigens were found to migrate to positions corresponding to about 35, 32 and 29 kilodaltons. These antigens were assigned the designations Antigen's VIIa-c, respectively, in that, as can be seen, only one member of the group has been seen in any one *P. haemolytica* strain. Thus, it is believed that the three antigenic species represent proteins which are modified, e.g., glycosylated, to differing degrees, or differ in terms of amino acid sequence.

4. Immunization of Calves and Rabbits with *P. haemolytica* Supernatant Proteins.

Both calves and rabbits were injected with *P. haemolytica* proteins to demonstrate that the proteins were immunogenic. Rabbit care, inoculation and serum isolation was performed by Bethyl Laboratories, Montgomery, Tex. Rabbits were injected, subcutaneously with 900 ug concentrated supernatant proteins combined with 500 ul Freund's incomplete adjuvant. Animals were boosted on day 21 with 900 ug of supernatant protein in incomplete Freund's adjuvant. Rabbits were bled weekly, beginning three weeks after the booster injection, and serum prepared: these sera were tested for their ability to recognize *P. haemolytica* supernatant and whole cell lysate proteins by western blotting of lysates and supernatants, as previously described.

Bovine experiments were performed using a twelve month old, 990 kg., Black Angus steer, pastured in New Summersville, Tex. The animal was inoculated subcutaneously with 200 ug *P. haemolytica* concentrated supernatant linked to one ml alum adjuvant on day one and then similarly boosted with the same mixture on day 21. Blood samples were collected in seven day intervals for eight weeks and serum was prepared. Sera were tested for the presence of, and found to contain, antibodies specific to *P. haemolytica* supernatant and whole cell lysate proteins by western blotting, performed as before.

Figure 2:
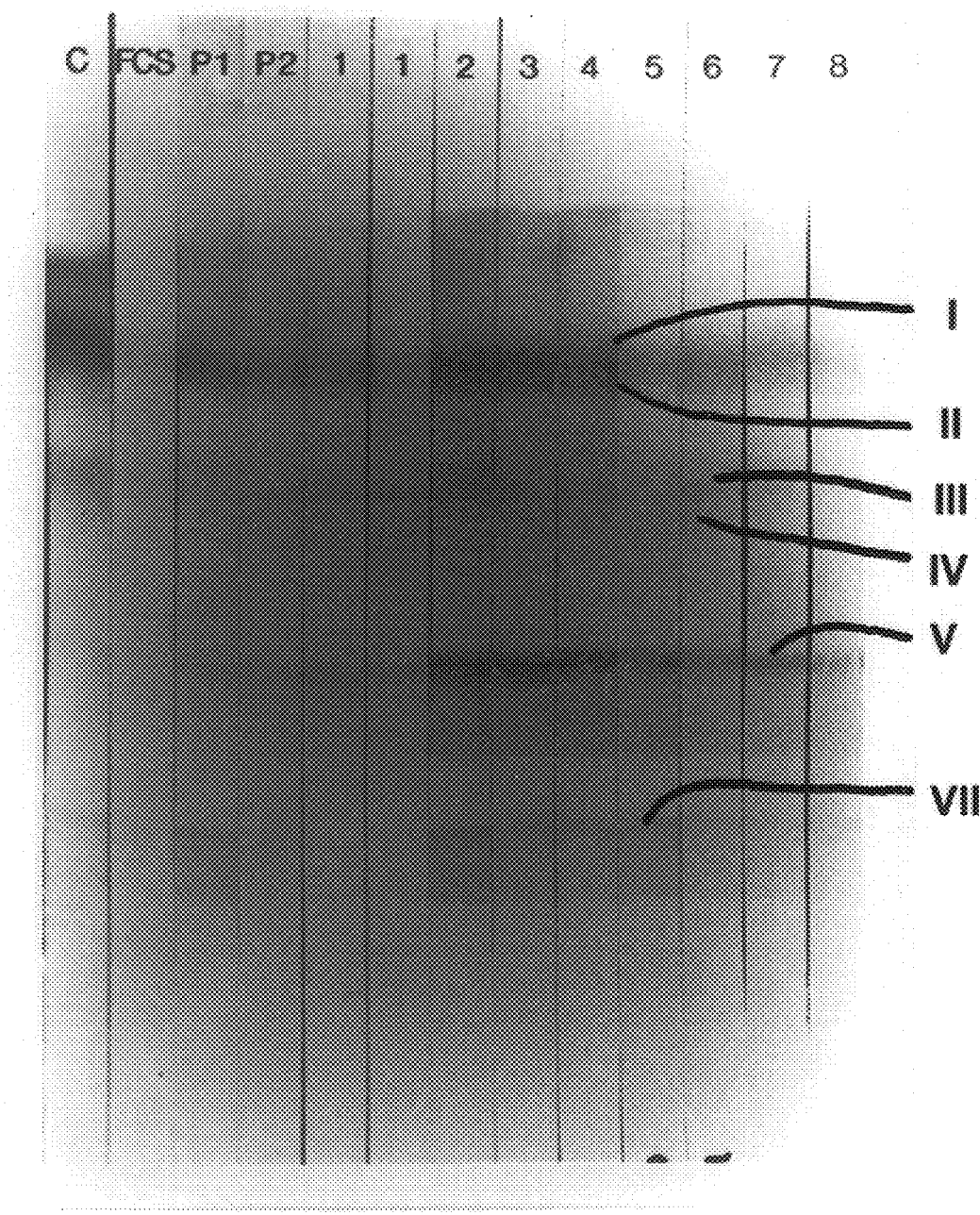

FIG. 2 is an immunoblot of *P. haemolytica* supernatant proteins which was cut into individual vertical strips. These individual strips were then incubated with 1/1000 dilutions of bovine serum from the following sources: lane C, convalescent serum (i.e.-serum from a naturally-infected, convalescent animal); lane FSC, fetal calf serum; lanes P1 and P2, preimmune test animal before immunization; lanes 1 through 8, serum from test animal, collected weekly, one through eight weeks following immunization with the antigenic composition including concentrated, dialyzed *P. haemolytica* supernatant proteins.

As can be seen from FIG. 2, the antigens recognized by the convalescent serum (lane c) were found to correspond generally to the antigens recognized by the test animal's sera. In particular, it was noted that the antibody titer for these particular antigens (Antigens I-VII) increased during the inoculation period, with antibodies to Antigens I, III, IV, V and VII increasing most dramatically. Thus, FIG. 2 demonstrates the antigenicity of the *P. haemolytica* supernatant, and of the individual antigens I–VII, and further, the ability of the supernatant to induce a response which is similar to, and augmented above, that seen in a convalescent animal.

As noted in the summary, the "reference weight" above refers to the weight which represents the inventors best estimate of a specific molecular weight. As such, the particular antigen groups may at times be referred to, for convenience, in terms of either the reference weight or the antigen group designation. Such references should not be interpreted to limit the scope of the present invention to any such specific reference molecular weight and is meant to include the range as a whole.

5. Elution of Antigen-Specific Antibodies from Nitrocellulose Blots.

To examine the antigenic relationship of one protein species to another, antibodies were eluted from a nitrocellulose blot and used to probe a second blot. Proteins separated on SDS/polyacrylamide gels were transferred to nitrocellulose, as described above. The blot was then incubated 10 minutes in a 0.2% solution of Ponceau S (Sigma Diagnostics, St. Louis, Mo.) to temporarily visualize the transferred proteins. Horizontal or vertical strips were cut from the nitrocellulose and these strips were treated with 1× TBS, 2% milk followed by primary antibody incubation, as described above. The strips were washed three times, at room temperature, in 100 ml 1× TBS 1% milk, for twenty minutes each and then rinsed briefly in 100 ml 1× TBS. The bound antibodies were removed by vortexing a crumpled nitrocellulose strip in 2 ml glycine-Hcl, pH 2.5 for two minutes. One ml of 0.5M $K_2HPO_4$, pH 9.0 was added immediately and the strip was vortexed again. The eluate was aspirated from the tube and then dialyzed for 16 hours at 4° C. versus 1× TBS. The dialysate was centrifuged 5 minutes at 8000×g, 4° C. to pellet the milk protein, and the clear supernatant, containing the eluted antibodies, was reserved. This solution was made 2% (w/v) in nonfat dry milk and then was used as primary antibody to probe other protein blots, as described in the previous section.

6. Electroelution of Pasteurella Supernatant Proteins from Acrylamide Gels.

Concentrated culture supernatants from *P. haemolytica* were electrophoresed on 7.5% SDS-polyacrylamide gels in one wide, 16 cm, well. Using prestained molecular weight markers as a guide, gel slices, containing specific protein bands, were cut from the gel. Each gel slice was immersed in SDS Gel Electrode Buffer (0.25M Tris, pH 8.3, 0.192M glycine, 1% SDS) and the protein was eluted from the acrylamide at a power of one watt for three hours, then 3 watts for an additional hour. The apparatus was maintained at 4° C. using a circulating ice-water bath and 1 ml samples of eluted protein solution were removed at 60 minute intervals. Aliquots of the eluted proteins were reelectrophoresed on an SDS-polyacrylamide gel to monitor recovery and purity.

Figure 3:
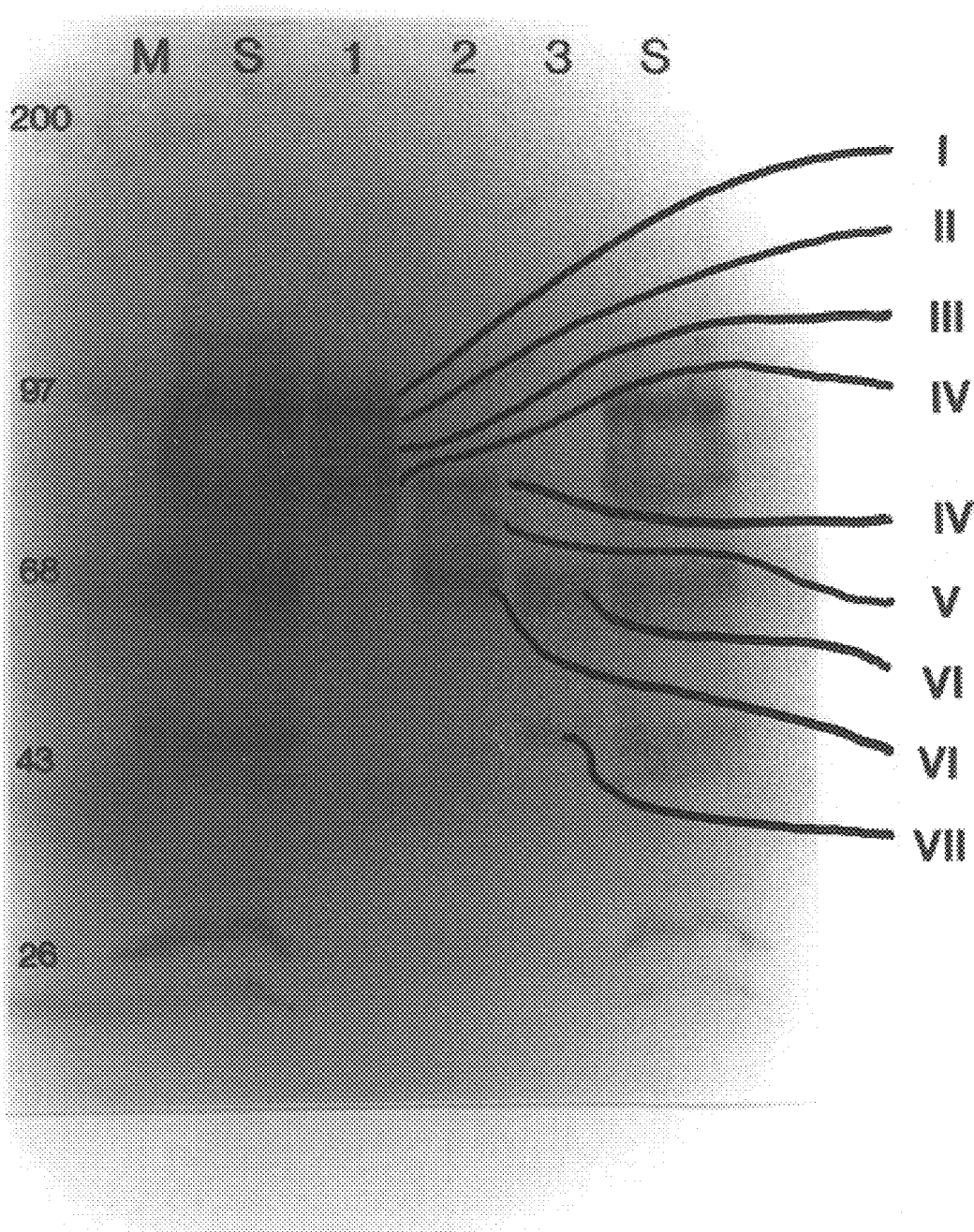

FIG. 3 illustrates a typical immunoblot of proteins fractionated by gel electrophoresis, isolated by gel electroelution, and rerun on a 7.5% SDS-polyacrylamide slab gel as follows: lane m, prestained molecular weight markers with sizes given in kilodaltons; lane a, *P. haemolytica* supernatant; lane 1, 80–100 kilodalton slice; lane 2, 60–80 kilodalton slice; lane 3, 40–60 kilodalton slice. The immunoblot was probed with a 1/1000 dilution of convalescent bovine serum.

As can be seen from FIG. 3, the 80 to 100 kilodalton slice included primarily Antigens I–IV, the 60 to 80 kilodalton slice included primarily Antigens IV–VI, and the 40 to 60 kilodalton fraction was found to include primarily Antigens VI and VII.

7. DEAE Sephadex Column Chromatography

Concentrated P. haemolytica supernatants were chromatographed over 15 cm by 150 cm² DEAE-Sephadex A25–120 columns which had been equilibrated with 10 mM Tris, pH 7.5. A single protein species was eluted with a 0.5 ml NaCl wash and collection of 20 ml fractions. This protein was subjected to immunoblot analysis and found to include primarily Antigens I and II.

8. Gel Filtration Column Chromatography

An ammonium sulfate precipitate of P. haemolytica supernatant was chromatographed on a 125 cm by 1.75 cm² Pharmacia Sephacryl 400 superfine column equilibrated with 10 mM potassium phosphate buffer, pH 7.6, 0.8% NaCl, 0.05% $NaN_3$. Sample volumes from 2.5 to 10 ml were applied and chromatographed in the equilibration buffer, and 1.5 ml fractions were collected. Typically, the bulk of the antigenic material was found to exclude from the column, suggestive of a high molecular weight antigen complex. This complex included Antigens I–VII, in a relatively purified form relative to unfractionated supernatant.

9. Antibody-Sepharose Chromatography

An alternate, or additional approach to the purification of antigens is through the use of antibody-Sepharose chromatography. In general, the approach requires the attachment of pasteurellosis-derived antisera to a suitable solid support, for example, Sepharose, and contacting the antibody-bound support with the cell-free supernatant so as to obtain binding of specific antigens to the antibodies. Methods for binding antibodies to affinity matrixes are well known in the art as, for example, detailed in *Methods in Enzymology*, Vol. 34B. After the immuno-complexed support is washed thoroughly to remove non-specifically bound proteins, the specifically-bound antigens are eluted to provide a substantially purified antigen mixture. One method which may be employed for conjugation to Sepharose is as follows:

The gel is first washed with distilled water. A ratio of approximately 1 g of protein to 30 g of dry gel (dry weight equals approximately volume of wet packed gel divided by 1.6) is utilized. To one volume of wet gel add a volume of 2M $Na_2CO_3$, and stir slowly and chill at 5° C. Then add 2 g of cyanogen bromide per 30 g dried gel (CNBr; dissolved in $CH_3CN$ at 2 g/ml) to the chilled mixture and stir vigorously for 1–2 minutes. The mixture is then poured into a cooled sintered glass funnel and washed rapidly with 10–20 volumes of cold 0.1M $NaHCO_3$. One volume of 0.2M $NAHCO_3$ containing the dissolved protein is added and the mixture, stirred gently for 20 hours at 4° C. Then it is washed on a sintered glass funnel with 10–20 volumes of 0.1M acetic acid with 0.5M NaCl, then with 0.1M $NAHCO_3$ (pH above 8.0). Then, an equal volume of ethanolamine (1M in 0.2M $NaHCO_3$) is added and the mixture is stirred for about 4 hours. The mixture is then washed on a sintered glass funnel with 3M KCl in 0.1M sodium phosphate buffer, pH 7.0, and then with starting column buffer.

Next, the supernatant is dissolved in, or dialyzed into, a buffer in which it is stable with an appropriate ionic strength to allow for the formation of an antigen-antibody complex (e.g.—0.02M phosphate buffer, 0.25M NaCl, pH 7.6). It is then passed over the matrix-bound antibody using the same buffer. After washing the column to remove unbound material, the specifically bound antigens are eluted with one of several solutions, for example, 0.1M acetic acid (for a low affinity antigen followed by 0.5M acetic acid (to elute high affinity antigens); 0.05M acid, pH 2.5 0.05M glycine-HCl buffer, pH 2.5; or 0.1M acetic acid followed by 6M urea. Where 6M urea is utilized, one will need to dialyze out the urea in a step wise fashion, for example, by reducing the urea concentration in the dialysate in molar increments.

B. PRODUCTION OF RECOMBINANT CELLS EXPRESSING P. HAEMOLYTICA ANTIGENS

The second general overall approach employed to identify P. haemolytica antigens involves the use of recombinant DNA technology. In particular, cells have been genetically engineered to express individual P. haemolytica antigens by transforming E. coli cells with randomized P. haemolytica DNA fragments to produce P. haemolytica clone banks through the use of two different types of E. coli cloning vectors—plasmid pUC7 and bacteriophage EMBL4. These vectors were chosen for convenience in that they are readily available and have been found by the present inventors to provide suitable clone banks for practicing the invention.

Although the foregoing cloning systems have been employed by the present inventors by way of illustration and convenience, it will be recognized that virtually any cloning system may be employed. For example, in that the cloning processes involve the cloning of bacterial sequences, it will be appreciated that there is no general requirement that an expression vector be employed to obtain expression of the cloned sequences, in the form of individual P. haemolytica antigen production. Due to the relative lack of complexity of bacterial gene control sequences, at least a sufficient proportion of randomized P. haemolytica DNA fragments will contain sequences sufficient to control the expression of the DNA when introduced into E. coli, regardless of the cloning vector employed. However, the use of a so-called "expression" vector (i.e.—a vector having built-in gene expression capability) may be employed to improve the percentage of recombinant clones present in the clone bank population which are actively expressing cloned P. haemolytica sequences.

In general, recombinant cells produced in accordance with the present invention are made by, first, isolating P. haemolytica DNA from any of the various serotype A1 strains, or from strains isolated from pasteurellosis-infected cattle. By way of illustration the inventors have employed strain PHL101. However, virtually any strain which is capable of eliciting pasteurellosis may be employed.

After isolation of the bacterial DNA, it then must be fragmented, preferably by a random fragmentation method. As discussed previously, random fragment generation provides a P. haemolytica DNA fragment population such that virtually every P. haemolytica gene is represented within the population. Moreover, even the most unique gene will be presented to an extent sufficient to provide a protein-expressing clone bank wherein the expression of virtually every transcriptionally active P. haemolytica gene is represented within the E. coli clone bank population.

The random DNA fragmentation method employed herein is partial restriction enzyme digestion. Partial restriction enzyme digestion is a preferred means of fragmentation because the random fragments so-generated will typically have restriction enzyme-produced "sticky ends" which may be readily annealed and ligated to correspondingly generated "sticky ends" of cloning vectors. However, other methods may be employed to generate random DNA fragments which are suitable. For example, the DNA may be mechanically or chemically sheared, through the use of a Waring blender, French pressure press sonication, passage through a syringe needle or chemical cleavage, to provide random fragments of a selected size. However, appropriate "linker" sequences must be ligated to sheared DNA in order to ligate the sequences with the cloning vector. Such alternate techniques are well known in the art and thus will not be presented in greater detail herein.

There is no actual requirement that *P. haemolytica* DNA be randomly fragmented in that there is no requirement that full protein coding sequences be cloned and expressed in the host, only that antigenically functional equivalents be expressed. In one embodiment, *P. haemolytica* DNA is fragmented through the use of total restriction digestion. Such fragments are not random in that, with total digestion, virtually every restriction recognition site within the DNA molecule will be recognized and cleaved by the selected enzyme. Thus, the DNA is reproducibly cleaved to reproducibly generate discrete fragments. Such fully restriction enzyme digested *P. haemolytica* DNA has been used to successfully construct clone banks which are capable of providing recombinant clones in accordance with the invention. However, it will be appreciate that where total restriction digestion is employed as a fragmentation method, it is preferably to employ an enzyme having a more selective sequence specificity (e.g.—six base pair specificity as opposed to four base pair specificity) in that such enzymes will have fewer recognition sites within any given DNA sequence, and hence, longer fragments will be generated. Typically, the longer the fragments so-generated, the greater the proportion of fragments that contain sequences coding for antigen determinants.

After the DNA has been fragmented, it is then inserted into the cloning vector, by ligation of the fragments to suitably cleaved vector DNA. By "suitably cleaved" is meant that the cloning vector DNA must be restriction enzyme cleaved at a suitable recombinant site within the vector. Determination of appropriate sites for any given vector is well within the skill of the art and may be determined, for example, from specification data supplied with the vector, when obtained from commercial sources, or from knowledge of the restriction enzyme map of the vector. Typically, a site is chosen which, when cleaved, serves to eliminate a particular genetic advantage provided by the vector to the host when the host is transformed. For example, cloning vectors may typically have drug resistance genes which, when left intact, confer a particular drug resistance to the host. However, when cleaved in a manner to receive inserted fragments to be cloned, the drug resistance gene is interrupted and no drug resistance is conferred to the host. In this manner, successfully transformed cells may be selected by selecting for those cells which don't display the particular drug resistance.

An alternative to the use of drug resistant markers is the use of cloning sites within other genes present within the vector, which genes, when intact, produce a detectable product, but, when cleaved to accept an inserted fragment, fail to produce the product. For example, many *E. coli* plasmids are constructed to contain sequences of the LacZ gene, which produces B-galactosidase when intact, but fails to produce this enzyme when a sequence has been inserted therein. Thus, successful transformants are selected on the basis of B-galactosidase production.

After construction of recombinant vectors, the vectors are used to transform an appropriate host. In a preferred embodiment, the host is an *E. coli* cell of a type which is compatible with the selected vector type. However, although the present invention is disclosed in terms of *E. coli* host/vector systems, other host/vector systems are known in the art and may be employed where desired. For example, numerous eukaryotic host/vector systems are known in the art (for example, see Okayama et al. (1983), *Mol. Cell. Biol.*, 3:280, for a description of a suitable eukaryotic expression vector derived from SV-40). Such systems are suitable for use in constructing recombinant cells in accordance with the present invention.

Transformation of host cells by the recombined vector is achieved using standard procedures known in the art. For example, where plasmid vectors are employed, transformation is typically achieved by permeabilizing competent cells with calcium and contacting the permeablized cells with the recombinant vector DNA. Where bacteriophage vectors are employed, one may additionally choose to package the recombinant phage with phage coat proteins, which affords direct transformation capability through cell infection with a resultant increase in transformation efficiency.

Once the cells are successfully transformed with the recombinant vector DNA, they are plated to provide individual recombinant clonal colonies or plaques, a selected proportion of which are actively producing *P. haemolytica* proteins. Moreover, a portion of these translationally active transformants will be actively producing *P. haemolytica* antigens. Thus, isolation of recombinant cells in accordance with the present invention requires the identification and selection of those transformed cells which produce *P. haemolytica* proteins, or their antigenic equivalents, that are recognized by pasteurellosis-induced antiserum. Typically, this identification is accomplished by testing each of the recombinant cells with the antiserum to identify clonal colonies or plaques which positively react and which positive reaction is indicative of *P. haemolytica* antigen production.

Once positive clones are selected, the antigens produced by the selected recombinant clones are isolated by, first, culturing the recombinant cell in a suitable media, and, if necessary, stimulating the vector promotor which carries the *P. haemolytica* gene to a state of active transcription. After plateau phase has been achieved, the cells are harvested, lysed by sonication, the debris centrifuged out, and the *P. haemolytica* antigen isolated by chromatography on a gel exclusion matrix or polyacrylamide gel.

The following example, Example II, demonstrates a specific embodiment of the foregoing general embodiments, and illustrate the successful development of *P. haemolytica* clone banks in *E. coli* hosts, using both plasmid and phage vectors, and further demonstrates the identification and isolation of transcriptionally active recombinant clones from such clone banks, which clones produce selected individual *P. haemolytica* antigens.

EXAMPLE II

Construction and Identification of Recombinant Cells Producing *P. haemolytica* Antigens 1. Bacterial Strains The *P. haemolytica* strains employed were as described for Example I. The *E. coli* strains used were KK2186, NM 538 and NM 539, as described by Frischauf et al. (183), *J. Mol. Biol.*, 170:827. *E. coli* strains were grown on LB media, with the addition of 100 ug/ml ampicillin, when necessary, or one mg agar medium supplemented with 125 ug/ml FX-Gel or 0.03 mM IPTG, as described by Maniatis, et al. (1982), *Molecular Cloning*, Cold Spring Harbor Laboratories, Cold Spring Harbor, N.Y.

2. Preparation of *P. haemolytica* Restriction Fragments for Construction of a Genomic Library.

Chromosomal DNA was prepared from *P. haemolytica* strain PHL101 by the lysozyme-Triton lysis method described by Davis, et al. (1980), Advanced Bacterial Genetics, Cold Spring Harbor Laboratory, N.Y. Briefly, a 100 ml late stationary phase culture of PHL101, grown in BHI, was harvested by centrifugation 10 minutes at 12,000× g. The pellet was resuspended in 2 ml 15% sucrose, 50 mM Tris, pH 8.5, 50 mM Na$_2$EDTA, containing 1 mg/ml fresh lysozyme. The cells were incubated 60 minutes at room temperature, then 2 ml 0.1% Triton X-100 (Sigma, St. Louis, Mo.), 50 mM Tris, pH 8.5, 50 mM Na$_2$EDTA was added. The lysate was incubated 30 minutes more at room temperature, then 40 ul 10 mg/ml RNAse A were added and the incubation was continued for 45 minutes at 37° C.

The resulting crude lysate was used to form a six ml ethidium bromide-CsCl density gradient (6 ml lysate, 6 g CsCl, 0.6 ml 10 mg/ml ethidium bromide) (Clewell and Helinski (1972), *J. Bacteriol.*, 110:1135). The gradient was centrifuged 18 hours, at 60,000 rpm in a 70.1 Ti rotor. The chromosomal DNA band was located using a long wave ultraviolet light source and was removed from the gradient with a needle and syringe. This DNA was then subjected to a second cycle of centrifugation through a fresh gradient and the chromosomal fraction reisolated. The ethidium bromide was removed by extraction with an equal volume of isopropanol and the resulting DNA solution was dialyzed 16 hours at 4° C. versus 100 volumes 1× TE Buffer (10 mM Tris, pH 8.0, 1 mM Na2EDTA).

For library construction, the PHL101 chromosomal DNA was digested partially with Sau 3A or completely with Bam HI, as follows. 250 ug PHL101 chromosomal DNA was digested with 12 units Sau 3A (BRL, Bethesda, Md.) in a total volume of 3.0 ml 6 mM Tris, pH 7.5, 50 mM NaCl, 6 mM MgCl$_2$ for one hour at 37° C. The reaction was terminated by the additional of 0.04 volume 0.5M Na$_2$EDTA. The restriction fragments were size-fractionated by centrifuging half of the digest through a 10 to 40% linear sucrose gradient (1M NaCl, 20 mM Tris, pH 8.0, 5 mM Na$_2$EDTA), as described by Maniatis, et al., supra (1982). The gradients were centrifuged 24 hours at 26,000 rpm, 20° C., using a SW27 swinging bucket rotor.

The bottom of the tube was punctured, 0.5 ml fractions were collected, and aliquots were analyzed by electrophoresis through a 0.5% agarose gel, 18 hours at 30 volts, using a TBE (89 mM Tris, 89 mM boric acid, 2 mM Na$_2$ EDTA) buffer system. Fractions containing fragments ranging from 5–10 kilobase (kb) and 10–20 kb in size were pooled separately, dialyzed versus TE and then precipitated by the addition of 0.1 volume 3M NaAc and 3 volumes cold 100% ethanol. After incubating 20 minutes on ice, the DNA fragments were collected by a 10 minute centrifugation in an Eppendorf centrifuge, washed once with cold 70% ethanol and then dried and resuspended in 100 ul 1× TE. Fragments were stored at −20° C.

When Bam HI fragments were required, 20 ug PHL101 chromosomal DNA were digested with 40 units Bam HI (BRL, Bethesda, Md.), in 100 ul 20 mM Tris, pH 8.0, 100 mM NaCl, 7 mM MgCl$_2$, for 2 hours at 37° C. The reaction was terminated by heating 10 minutes at 65° C. and the digest was stored at −20° C.

3. Construction of a *P. haemolytica* Plasmid Library in *E. coli*.

The *E. coli* cloning vector, pUC7 was selected for construction of a *P. haemolytica* Sau 3A fragment library. The vector carries the pBR322 origin of replication, ampicillin resistance gene and a portion of the Lac Z (B-galactosidase) gene with the M13mp7 multiple cloning site (Messing, et al. (1981), *Methods in Enzymology*, 101:10). Insertion of a Sau 3A into the Bam HI site on the vector interrupts the Lac Z gene and causes the loss of B-galactosidase activity.

Plasmid pUC7 DNA was prepared from *E. coli* strain KK2186, carrying the plasmid, as described for the preparation of Pasteurella chromosomal DNA, except that the bacteria were grown in LB broth containing 100 ug/ml ampicillin, and that the plasmid, not chromosomal DNA band, was removed from the CsCl gradient. 175 ug pUC7 DNA was digested with 20 units Bam HI in 700 ul 20 mM Tris, pH 8.0, 100 mM NaCl, 7 mM MgCl$_2$, at 37° C. for two hours. The reaction was heated 10 minutes at 65° C., then 2 units alkaline phosphatase (Boehringer-Mannheim, Indianapolis, Ind.) were added and incubation continued for 45 minutes at 37° C. The reaction was again heated for 10 minutes at 65° C.

Linear pUC7 molecules were purified by electrophoresing the digest mixture on a 5% polyacrylamide gel (19 acrylamide:1 bis, 1× TBE) 3 hours at 15 volts/cm. The gel was stained with a 2% methylene blue solution and the DNA band was located and excised from the gel. A glass rod was used to crush the gel slice into a fine paste and the paste was suspended in 2 ml Extraction Buffer (10mM Tris, pH 8.0, 50 mM NaCl, 10 mM Na$_2$EDTA). This slurry was incubated 16 to 24 hours at 37° C. and then spun through a 1 cm glass wool plug, 10 minutes, 2000×g, to separate the DNA solution from the acrylamide. The DNA solution was extracted once with TE-saturated phenol, extracted three times with anhydrous ethyl ether and then ethanol precipitated by addition of 0.1 volume 3M NaAc plus 3 volumes cold 100% ethanol and incubation for 20 minutes on ice. The DNA was collected by centrifugation 10 minutes in an Eppendorf centrifuge, the pellet was dried, and then resuspended in 500 ul TE to a final concentration of 20 ug/ml.

Bam HI-linearized pUC7 DNA was mixed with a portion of the PHL101 5–10 kb Sau 3A partial digest pool and ligated as follows. 1.25 ug pUC7 was combined with 2 ug of the pooled Sau 3A fragments and ethanol precipitated. The DNA pellet was resuspended in 100 ul Ligation Buffer (66 mM Tris, pH 7.6, 6.6 mM MgCl$_2$, 10 mM DTT, 0.4 m ATP) plus 2 units T4 DNA Ligase (Boehringer Mannheim, Indianapolis, Ind.) and then incubated 18 hours at 15° C. The ligation mixture was used to transform frozen competent KK2186 cells prepared as described by Messing, supra. Aliquots of the ligation mixture were combined with 100 ul thawed competent cells and held on ice for 30 minutes. The transformation mixture was heated for 5 minutes at 37° C. and then 0.5 ml LB containing 100 ug/ml ampicillin was added.

The transformed cells were incubated 2 hours at 37° C. to allow expression of the antibiotic resistance marker and then plated onto m9 agar plates containing ampicillin, X-Gal and IPTG. Plates were incubated 20 hours at 37° C. Theoretically, any plasmid carrying a DNA fragment inserted into the Bam HI site should produce a white colony on X-Gal indicator plates because this insertion interrupts the Lac Z coding sequence, however, fusions of insert sequences to Lac Z could restore expression of a functional B-galactosidase. For this reason, all colonies, both white and blue, were transferred to individual wells of microtiter plates containing 200 ul LB broth plus 20 ul DMSO. These stocks were stored at −80° C.

4. Antibody Screening of Plasmid Library Transformants.

*E. coli* colonies were probed in situ (Helfman, et al. (1983), *Proc. Natl. Acad. Sci., U.S.A.*, 80:31) with bovine sera to detect expression of cloned Pasteurella antigen genes. An eight by six pronged replicator was used to transfer putative transformants to a nitrocellulose disk overlaid on an LB agar plate containing ampicillin. Plates were inverted and incubated 18 hours at 37° C. The filters, carrying bacterial colonies, were removed and placed in a covered glass dish filled with chloroformsaturated paper toweling and held for 15 to 20 minutes to lyse the colonies. Each filter was air-dried, placed in a clean dish and incubated 18 hours with 10 ml 1× TBS, 2% milk, 1 ug DNAse, 40 ug lysozyme, at room temperature. The filters were washed twice with 10 ml TBS, then incubated 2 hours at 37° C. with 200 ul bovine serum in 200 ml 1× TBS, 2% milk. The filters were then washed and treated exactly as described for immunodetection of proteins, as described above. Colonies producing immunoreactive products were purified, grown in liquid culture, and used to prepare whole cell lysates for western blotting and protein identification, also as described above.

Figure 4A:
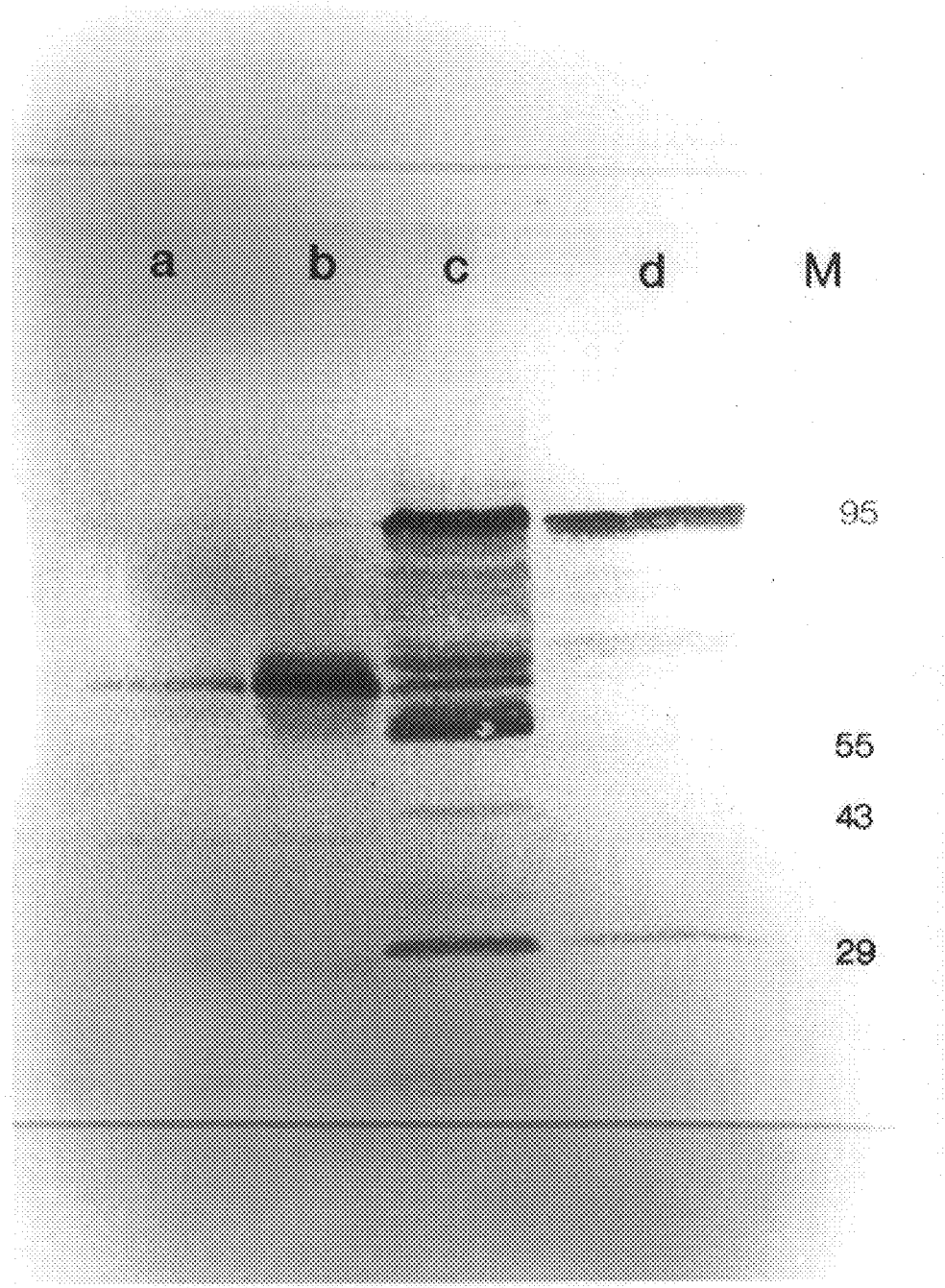
Figure 4B:
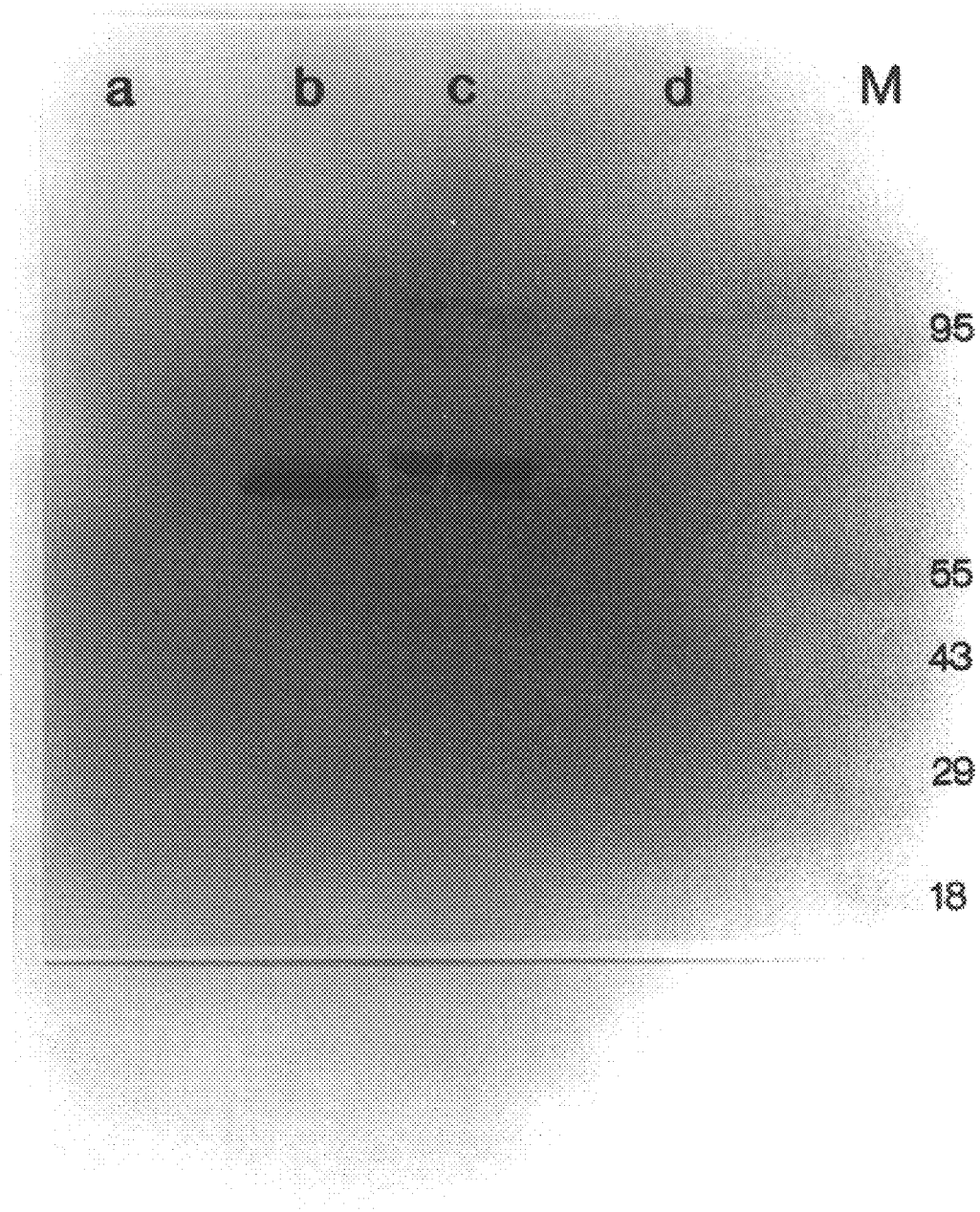

The predominant antigen found to be expressed by various of the plasmid transformation exhibited a molecular weight of about 66 kilodaltons upon immunoblot analysis. FIGS. 4A and 4B present an immunoblot of one such clone, designated pSH200. In particular, FIGS. 4A and 4B are is an immunoblot of $E.$ $coli$ and $P.$ $haemolytica$ whole cell lysates and a $P.$ $haemolytica$ supernatant preparation probed with: FIG. 4A, a $\frac{1}{1000}$ dilution of convalescent bovine serum, or FIG. 4B, antigen eluted from $E.$ $coli$ cells carrying pSH200 as described herein. Lanes on each gel are as follows—lane a, $E.$ $coli$ KK2186 (pUC7) whole cell lysate; lane b, $E.$ $coli$ KK2186 (PSH200) whole cell lysate; lane c, PHL101 whole cell lysate; lane d, PHL101 cell-free supernatant; lane m, molecular weight markers.

As can be seen from FIGS. 4A and 4B, a 66 kilodalton protein, reactive with antisera, was identified in recombinant cell pSH200 (lane b), but not in the non-recombinant $E.$ $coli$ host and vector (lane a). Antibodies with specificity for the 66K protein recognized a 66K and a slightly larger intracellular $P.$ $haemolytica$ antigen and also reacted to a lesser extent with the 105K protein found in the cell-free supernatant.

$E.$ $coli$ KK2186 bearing recombinant plasmid, pSH200, has been deposited with the ATCC on Nov. 25, 1987, and accorded ATCC accession number 67274.

5. Construction of a $P.$ $haemolytica$ Library Using Bacteriophage Lambda.

Bam HI fragments of the PHL101 chromosome were used to construct a library using the lambda cloning vector, EMBL4 (Frischauf et al., supra (1983). EMBL4 DNA was purchased from Promega Biotec, Madison, Wis. and 10 ug of this DNA was digested with 10 units Bam HI in a total volume of 25 ul 20 mM Tris, pH 8.0, 100 mM NaCl, 7 mM $MgCl_2$, for 2 hours at 37° C. The reaction was heated for 10 minutes at 65° C. and then 1 ul 5M NaCl, 2 ul 5 mM Na2EDTA, 20 ul water and 1.5 units Sal I (BRL, Bethesda, Md.) were added. The Sal I digest was incubated two hours at 37° C.; this second restriction digestion cleaves the non-essential "stuffer" region of EMBL4 and is used to reduce the probability of parental bacteriophage reconstruction. Five ug of Bam HI/Sal I digested EMBL4 DNA was combined with 5 ug Bam HI digested $P.$ $haemolytica$ chromosomal DNA in a total volume of 100 ul. This mixture was extracted once with a 1:1 mixture of phenol:chloroform, then once with pure chloroform, then three times with anhydrous ethyl ether. The volume of the aqueous phase was brought to 150 ul and 22 ul 3M NaAc and 90 ul isopropanol were added to selectively precipitate the larger DNA fragments. The precipitate was held on ice for 15 minutes, collected by centrifugation 15 minutes in an Eppendorf centrifuge and the pellet washed once with a 1:2.5 mixture of 0.35M NaAc:ethanol. The dried pellet was resuspended in 20 ul Ligation Buffer containing 2 units ligase, and the mixture was incubated 18 hours at 15° C.

Half of the ligation mixture was packaged, in vitro, into lambda particles using the Packagene Lambda DNA Packaging System purchased from Promega Biotec, Madison, Wis. (Maniatis, et al., supra): DNA was mixed with an entire, thawed extract, mixed gently, and then held at room temperature for 2 hours. 0.5 ml Phage Buffer (0.1M NaCl. 0.01M Tris, pH 7.9, 0.01M $MgSO_4$) was added, then 25 ul chloroform, and the reaction was vortexed to mix. The phage titer of the packaging reaction was determined by plating the phage on NM538 (permissive host) and NM539 (restrictive host where only recombinant phage missing the stuffer fragment can form plagues), as follows. Overnight cultures of plating bacteria were harvested by centrifugation at 8000×g for 10 minutes and the pellets resuspended in a 0.4× volume of 10 mM $MgSO_4$. An aliquot or dilution of the packaging extract was combined with 100 ul plating bacteria and held 20 minutes at room temperature. Phage and cells were mixed with 2.5 ml soft agar and plated directly onto LB or Lambda Agar plates and then incubated 18 hours at 37° C.

Plates having 100 or more plaques on the restrictive host, NM539, were scraped, to remove the overlay, into a Teflon centrifuge tube and the agar resuspended in 10 ml phage buffer. A 0.1 volume of chloroform was added and the mixture was vortexed to disperse the phage. The mixture was held 30 minutes at 4° C. and then centrifuged 10 minutes at 1900×g. The supernatant, containing amplified recombinant phage, was removed and stored at 4° C.

6. Antibody Screening of Bacteriophage Library.

Recombinant phage producing Pasteurella proteins that could be recognized by bovine sera were detected by a direct application of the techniques described above for immunodetection of proteins in plasmid library screening. Approximately $10^4$ recombinant phage from an amplified stock were plated with 1.0 ml NM539, as described above, onto a 150 mm Petri plate of Lambda agar, using 10 ml 0.7% agarose instead of soft agar for the overlay. The plate was incubated 1.5 hours at 37° C., to allow the lawn to develop, and then overlaid with a 137 mm 0.45 um nitrocellulose disk. Incubation was continued for 15 hours at 37° C., after which the nitrocellulose disk was removed and incubated for 60 minutes in 100 ml 1× TBS, 2% milk at 37° C. Duplicate filters were obtained by overlaying the plate with a fresh nitrocellulose filter and incubating 10 minutes more at 37° C. After the incubation with TBS and milk, the plaque lifts were treated exactly as described for the remaining immunodetection steps.

Plaques that gave positive responses in the primary antibody screen were plugged from the original agar plate with a sterile Pasteur pipette into 2 ml phage buffer containing 25 ul chloroform and vortexed. The resulting solution was serially diluted in phage buffer and spotted onto fresh overlays of NM539. The resulting plaques were retested by the plaque lift and antibody screening techniques and true positives were identified. When necessary, these isolates were further amplified by mixing 1–4 plaques with 50 ul NM538 in a 16×150 mm culture tube, holding 5 minutes at room temperature, and then adding 2 ml pre-warmed LB broth containing 10 mM $MgSO_4$. The tubes were rotated on a roller drum at 37° C. for 6 to 8 hours until lysis occurred. 0.1 ml chloroform was added to each and the titer of each 2 ml stock was determined, using NM538 as plating bacteria (Silhavy, et al., 1984).

Immunoreactive proteins encoded by recombinant bacteriophage were further characterized by SDS/polyacrylamide gel electrophoresis. Bacteriophage lysates with titers as low as $10^4$ plaque forming units/ml were used as in vivo whole cell lysates for immunological testing. Forty ul of lysate was mixed with 20 ul 3× SDS Loading Buffer and boiled 5 minutes before being loaded onto and run on a 7.5% gel, exactly as described for whole cell lysates. This gel was blotted and treated with antibody and HRP-streptavidin, as previously described, and allowed a direct measurement of the size of cloned proteins.

Figure 5:
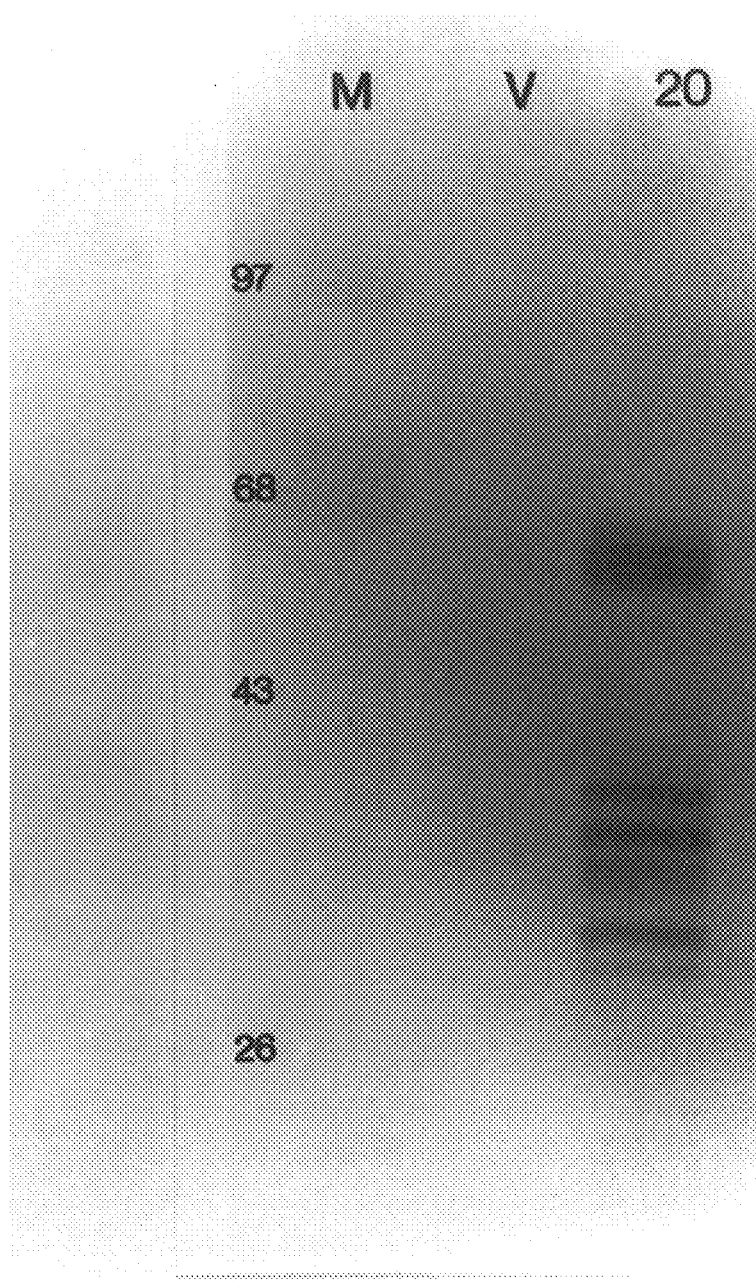

Using the foregoing techniques, the predominant antigenic protein found to be expressed by phage-infected recombinant cells, is a protein which exhibits a molecular weight of approximately 55 kilodaltons by immunoblot of a representative clone, designated clone Lambda SH-20. (shown in FIG. 5). The immunoblot was probed with convalescent serum. In addition to the 55K species, 5 or more smaller antigens were also seen on the immunoblot of Lambda SH20 phage lysate. These bands are not present in the vector control lane which implies that these antigens are encoded by the cloned DNA fragment. The smaller species are believed to be specific degradation products of the 55K protein. A representative sample of Lambda SH-20 phage have been deposited with the ATCC on Nov. 25, 1987, and accorded accession number 40285. Additionally, a representative sample of phage from two phage P. haemolytica clone banks have been deposited with the ATCC. One phage clone bank, Lambda EMBL4: PhBam, constructed using total Bam HI digestion of P. haemolytica DNA, was deposited on Nov. 25, 1987, and accorded accession number 40286. A second phage clone bank, Lambda EMBL4: PhSau, was constructed using partial Sau 3A digested P. haemolytica DNA, deposited with the ATCC, and accorded accession number 40287.

7. Purification of Cloned Pasteurella Proteins from Escherichia coli Cells.

E. coli cells carrying a gene encoding a Pasteurella protein are grown to mid-logarithmic phase in LB broth or other suitable media. If the gene is controlled by the lactose promoter, isopropyl thiogalactopyranoside (IPTG) is included during the logarithmic growth phase to induce transcription of the cloned gene. The cells are harvested, resuspended in 10 mM Tris, pH 7.5 and then mechanically lysed by sonication, freezing and thawing, or passage through a French pressure cell. Cell debris is removed by centrifugation, 10 minutes at 8000×g, and the protein-containing supernatant is concentrated by ammonium sulfate or polyethylene glycol precipitation. The Pasteurella protein can then be purified from the concentrate by a combination of chromatography methods.

EXAMPLE III

Construction and Identification of Recombinant Cells Producing P. Haemolytica Supernatant Antigens The present example is directed to the disclosure of an alternative and improved method for the isolation of P. haemolytica supernatant antigens shown above in Example I and, in particular, the 105 Kilodalton antigen designated therein as supernatant Antigen I. The method disclosed by the present example employs recombinant DNA techniques to clone P. haemolytica genes which encode supernatant antigens. Although the present example is disclosed in terms of antigen-expressing recombinant clones which are isolated from a Bgl II—P. haemolytica clone bank, there is no reason why the Sau 3A bank disclosed above would not work equally as well.

1. Preparation of P. haemolytica Restriction Fragments for Construction of a Genomic Library.

Chromosomal DNA was prepared from P. haemolytica strain PHL101 by the lysozyme-triton lysis method described by Davis, et al., supra. A 100 ml late stationary phase culture of PHL101, grown in BHI, was harvested by centrifugation 10 minutes at 12,000×g. The pellet was resuspended in 2 ml 15% sucrose, 50 mM Tris, pH 8.5, 50 mM $Na_2EDTA$, containing 1 mg/ml fresh lysozyme. The cells were incubated 60 minutes at room temperature, then 2 ml 0.1% Triton X-100 (Sigma, St. Louis, Md.), 50 mM Tris, pH 8.5, 50 mM $Na_2EDTA$ were added. The lysate was incubated 30 minutes more at room temperature, then 40 ul 10 mg/ml RNAse A were added and the incubation was continued for 45 minutes at 37° C.

The resulting crude lysate was used to form a six ml ethidium bromide-CsCl density gradient (6 ml lysate, 6 g CsCl, 0.6 ml 10 mg/ml ethidium bromide) (Clewell and Helinski, supra). The gradient was centrifuged 18 hours at 60,000 rpm in a 70.1 Ti rotor. The chromosomal DNA band was located using a long wave ultraviolet light source and was removed from the gradient with a needle and syringe. This DNA was then subjected to a second cycle of centrifugation through a fresh gradient and the chromosomal fraction reisolated. The ethidium bromide was removed by extraction with an equal volume of isopropanol and the resulting DNA solution was dialyzed 16 hours, 4° C. versus 100 volumes 1× TE Buffer (10 mM Tris, pH 8.0, 1 mM $Na_2EDTA$).

For library construction, the PHL101 chromosomal DNA was digested completely with Bgl II, as follows. 20 ug PHL101 chromosomal DNA were digested with 40 units Bgl II (BRL, Bethesda, Md.), in 100 ul 20 mM Tris, pH 7.6, 50 mM NaCl, 7 mM $MgCl_2$, for 2 hours at 37° C. The reaction was terminated by heating 10 minutes at 65° C. and the digest was stored at −20° C.

2. Construction of a P. Haemolytica Library Using Bacteriophage Lambda.

Bgl II fragments of the PHL101 chromosome were used to construct a library using the lambda cloning vector, EMBL4 (Frischauf, et al., supra). EMBL4 DNA was purchased from Promega Biotec, Madison, Wis. and 10 ug of this DNA was digested with 10 units Bam HI in a total volume of 25 ul 20 mM Tris, pH 8.0, 100 mM NaCl, 7 mM $MgCl_2$, for 2 hours at 37° C. The reaction was heated for 10 minutes at 65° C. and then 1 ul 5M NaCl, 2 ul 5 mM $Na_2EDTA$, 20 ul water and 1.5 units Sal I (BRL, Bethesda, Md.) were added. The Sal I digest was incubated two hours at 37° C.; this second restriction digestion cleaves the non-essential "stuffer" region of EMBL4 and was used to reduce the probability of parental bacteriophage reconstruction. Five ug of Bam HI/Sal I digested EMBLA DNA was combined with 5 ug Bgl II-digested P. haemolytica chromosomal DNa in a total volume of 100 ul.

This mixture was extracted once with a 1:1 mixture of phenol:chloroform, then once with pure chloroform, then three times with anhydrous ethyl ether. The volume of the aqueous phase was brought to 150 ul and 22 ul 3M NaAc and 90 ul isopropanol were added to selectively precipitate the larger DNA fragments. The precipitate was held on ice for 15 minutes, collected by centrifugation 15 minutes in an Eppendorf centrifuge and the pellet washed once with a 1:2.5 mixture of 0.35M NaAc:ethanol. The dried pellet was resuspended in 20 ul Ligation Buffer containing 2 units ligase, and the mixture was incubated 18 hours at 15° C.

Half of the ligation mixture was packaged, in vitro, into lambda particles using the Packagene Lambda DNA Packaging System purchased from Promega Biotech, Madison, Wis. (Maniatis, et al., supra): DNA was mixed with an entire thawed extract, mixed gently, and then held at room temperature for 2 hours. 0.5 ml Phage Buffer (0.1M NaCl, 0.01M Tris, pH 7.9, 0.01M $MgSO_4$) was added, then 25 ul chloroform, and the reaction was vortexed to mix. The phage titer of the packaging reaction was determined by plating the phage on NM538 (permissive host) and NM539 (restrictive host where only recombinant phage missing the stuffer fragment can form plaques), as follows.

Overnight cultures of plating bacteria were harvested by centrifugation at 8000×g for 10 minutes and the pellets resuspended in a 0.4× volume of 10 mm $MgSO_4$. An aliquot or dilution of the packaging extract was combined with 100 ul plating bacteria and held 20 minutes at room temperature. Phage and cells were mixed with 2.5 ml soft agar and plated directly onto LB or Lambda Agar plates and then incubated 18 hours at 37° C. Plates having 100 or more plaques on the restrictive host, NM539, were scraped, to remove the overlay, into a teflon centrifuge tube and the agar resuspended in 10 ml Lambda Diluent (10 mM Tris, pH 7.6, 10 mM $MgSO_4$, 1 mM $Na_2EDTA$. A 0.1 volume of chloroform was added and the mixture was vortexed to disperse the phage. The mixture was held 30 minutes at 4° C. and then centrifuged 10 minutes at 1900×g. The supernatant, containing amplified recombinant phage, was removed and stored at 4° C.

3. Antibody Screening of Bacteriophage Library.

Recombinant phage producing Pasteurella proteins that could be recognized by bovine sera were detected by a direct application of the techniques described above for immunodetection of proteins and plasmid library screening. Approximately $10^4$ recombinant phage from an amplified stock were plated with 1.0 ml NM539, as described above, onto a 150 mm Petri plate of Lambda agar, using 10 ml 0.7% agarose instead of soft agar for the overlay. The plate was incubated 1.5 hours at 37° C., to allow the lawn to develop, and then overlaid with a 137 mm 0.45 um nitrocellulose disk. Incubation was continued for 15 hours at 37° C., after which the nitrocellulose disk was removed and incubated for 60 minutes in 100 ml 1× TBS, 2% milk at 37° C. Duplicate filters were obtained by overlaying the plate with a fresh nitrocellulose filter and incubating 10 minutes more at 37° C. After the incubation with TBS and milk, the plaque lifts were treated exactly as described for the remaining immunodetection steps.

Plaques that gave positive responses in the primary antibody screen were plugged from the agar with a sterile Pasteur pipette into 2 ml Lambda Diluent containing 25 ul chloroform and vortexed. The resulting solution was serially diluted in Lambda Diluent and spotted onto fresh overlays of NM539. These plaques were retested by the plaque lift and antibody screening techniques and true positives were identified. When necessary, these isolates were further amplified by mixing 1–4 plaques with 50 ul NM538 in a 16×150 mm culture tube, holding 5 minutes at room temperature, and then adding 2 ml pre-warmed 1B broth containing 10 mM $MgSO_4$. The tubes were rotated on a roller drum at 37° C. for 6 to 8 hours until lysis occurred. 0.1 ml chloroform was added to each and the titer of each 2 ml stock was determined, using NM538 as plating bacteria.

Immunoreactive proteins encoded by recombinant bacteriophage were further characterized by SDS/polyacrylamide gel electrophoresis. Bacteriophage lysates with titers as low as $10^4$ plaque forming units/ml were used as in vivo whole cell lysates for immunological testing. Forty ul of lysate was mixed with 20 ul 3× SDS Loading Buffer and boiled 5 minutes before being loaded onto and run on a 7.5% gel, exactly as described for whole cell lysates. This gel was blotted and treated with antibody and HRP-streptavidin, as previously described, and allowed a direct measurement of the size of cloned proteins.

Figure 6:
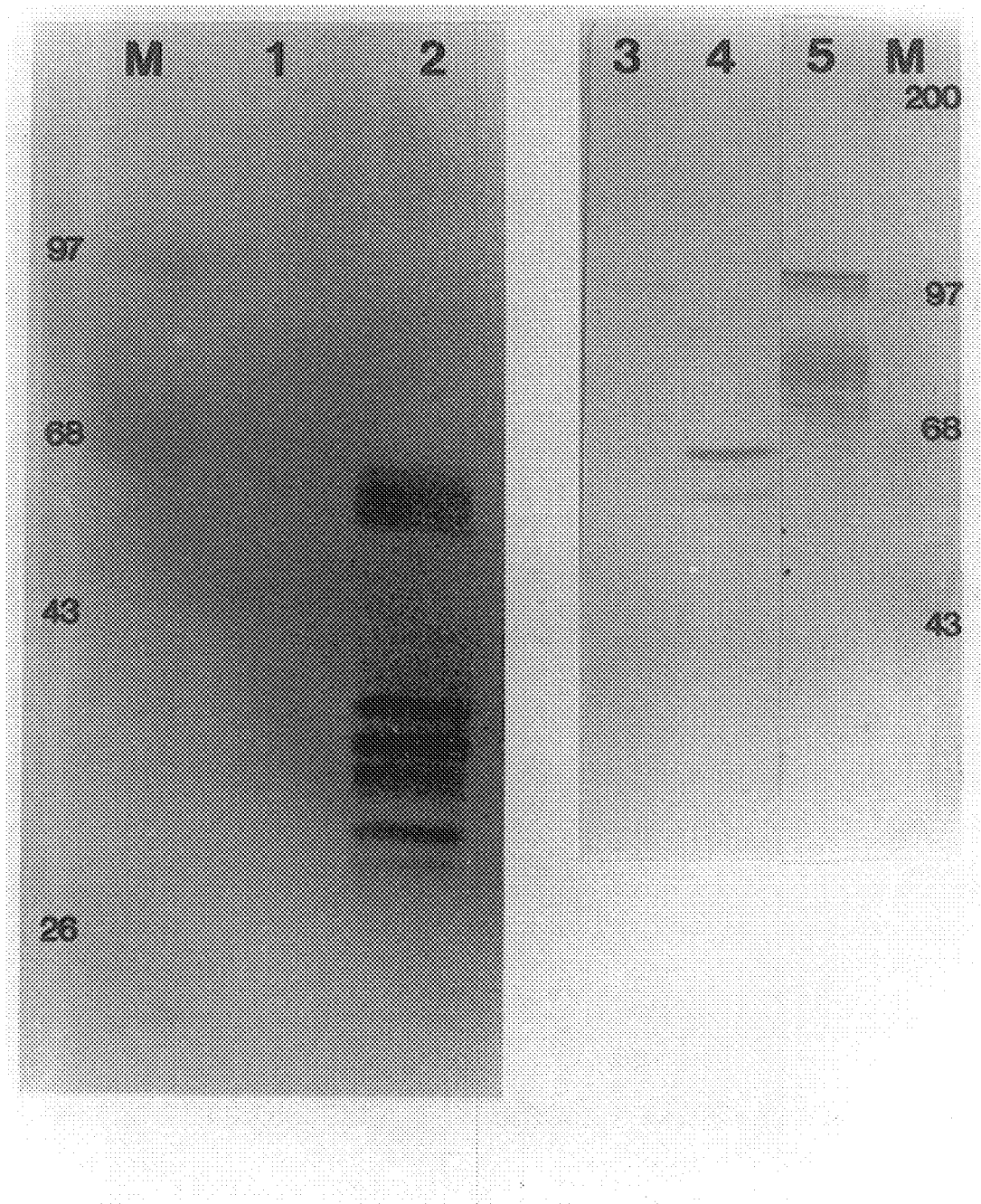

Antibody screening of the Bql II recombinant phage library provided 34 positive single-plague isolates. Following purification and amplification, crude phage lysates of the isolates were tested for antigen production by Western blotting using bovine immune serum. Eight of the 34 original isolates produced an antigen that was visible on an immunoblot. Seven of these produced the same 66 kD antigen that was previously identified as being encoded by plasmid pSH200 from the pUC7 plasmid library. Southern blot analysis verified that these seven isolates carried the same 3.0 kb Eco RI fragment carried by pSH200. The remaining recombinant phage, Lambda SH132, produced an antigen having an apparent molecular weight of 105 kD. (See FIG. 6) This antigen corresponds to Antigen Group I of the *P. haemolytica* supernatant antigen groups. Antibodies eluted from immunoblots of Lambda SH132 were able to recognize Antigen I, indicating that these proteins were antigenically identical.

4. Subcloning and Mapping the 105 kD Antigen Gene.

To facilitate mapping and expression of the 105 kD antigen gene, the *P. haemolytica* DNA insert from lambda SH132 was cloned into the plasmid vector, pBS (+) (Stratagene, San Diego, Calif.). Restriction analysis of Lambda SH132 indicated that the insert was cut once by Eco RI, yielding 1.2 and 17.6 kb fragments. Therefore, Eco RI was used to cut Lambda SH132 for subcloning, as follows.

One ug of Lambda SH132 was digested with 10 units Eco RI 2 hours at 37° C. in a 50 ul reaction containing 100 mm Tris, pH 7.5, 10 mM $MgCl_2$, 50 mM NaCl. Five ug pBS (+) were similarly digested. To prevent religation of the vector, the digested pBS (+) DNA was treated with calf intestinal phosphatase.(CIP). The digested Lambda SH132 DNA was combined with one ug Eco RI-linearized pBS (+). The DNAs were coprecipitated and then ligated, as previously described.

One-half of the ligation mixture was used to transform competent KK2186 cells with selection at 30° C. on LB plates containing ampicillin and X-Gal. Cells carrying plasmids with inserts were identified as white colonies on these indicator plates. Restriction digest analysis of plasmid DNAs prepared from these isolates indicated that three different plasmid constructs had been generated: pSH207 (pBS::Lambda SH132 17.6 kb Eco RI, orientation A), pSH209 (pBS::Lambda SH132 17.6 kb Eco RI, orientation B), and pSH210 (pBS:: Lambda SH132 1.2 kb Eco RI). Restriction maps for these three constructs are shown in FIG. 7A.

Whole cell lysates of strains carrying the plasmids were prepared and tested by Western blotting to show that the 17.6 kb Eco RI fragment produced the 105 kD antigen (FIG. 7B). Plasmid pSH210 did not produce an antigen while pSH209 produced more of the 105 kD antigen than did pSH207. This suggested that the expression of the 105 kD antigen gene could be influenced by vector sequences that flanked the insert, e.g. by the Lac promoter on pBS (See following section of Antigen Production).

The location of the gene was further mapped within the 17.6 kb Eco RI fragment by constructing in vitro deletions of pSH207 and then testing deletants for antigen production by Western blotting. Deletions were constructed by digesting 1–5 ug pSH207 with either Ava I, Hinc II, Pst I, or double digests of Bam HI plus Bgl II or Acc I plus Cla I under standard digestion conditions. The digested DNAs were phenol extracted, ethanol precipitated and then resuspended in Ligation Buffer and ligated with T4 DNA ligase, as previously described.

The ligated DNAs were transformed into competent KK2186 cells with selection for ampicillin resistance. Plasmid DNA was prepared from transformants corresponding to each deletion type and screened for the loss of the expected DNA fragments by restriction digest analysis. Maps of the resulting deletants are shown in FIG. 7A. The deletant plasmids are: pSH214 (Hinc II deletion), pSH215 (Pst I deletion), pSH216 (1.2 kb Ava I deletion), pSH217 (Acc I—Cla I deletion), pSH218 (Bam HI—Bgl II deletion) and pSH219 (1.2, 1.4 kb Ava I deletion). Whole cell extracts of the strains carrying the deletant plasmids were tested for the production of the 105 kD antigen by Western blot analysis, as before (FIG. 7B).

The nucleotide sequence of the ptx gene was determined using single stranded templates from subclones in M13 and pBS vectors, and the T7 DNA polymerase, Sequenase kit of United States Biochemicals (Cleveland, Ohio). The nucleotide sequence determined was subjected to computer sequence analysis using the Pustell DNA Sequence Analysis Program of International Biotechnologies, Inc. (New Haven, Conn.), from which was deduced the amino acid sequences encoded by the DNA that was analyzed.

Shown in FIGS. 9A–9L is a DNA sequence extending from a BamHI/BglII cloning junction including the sequence determined for the leukotoxin (105K antigen) gene and additional sequences represented within the original lambda SH132 clone, as well as in plasmid pSH209.

5. Antigen Production and Leukotoxin Activity.

Since it was observed that the level of expression of the 105 kD antigen was orientation dependent, it was anticipated that the Lac promoter on the Bluescribe vector was contributing to the transcription of the cloned Pasteurella gene. Strain KK2186 produces Lac repressor and maintains a low level of Lac promoted transcription; in the presence of IPTG, transcription is induced. Therefore, cells carrying either pSH207 or pSH209 were grown in the presence and in the absence of IPTG to determine if the expression of the 105 kD Antigen I could be induced. Cells were grown at 30° C. in LB broth containing ampicillin to a turbidity of 150 Klett units. The cultures were split and IPTG was added to one half of each culture to 0.5 mM. Growth at 30° C. was continued for 3 hours and then the cells were harvested by centrifugation. Whole cell extracts were prepared and subjected to Western blot analysis, as before. FIG. 8 shows that production of the antigen was increased at least 10-fold by IPTG from pSH209, while IPTG did not significantly increase expression from pSH207. This enhanced expression under control of an inducible promoter has allowed us to produce relatively large quantities of the 105 kD antigen for other studies.

Whole cell extracts of IPTG-induced $E. coli$ cells carrying pSH209 were used in an assay to demonstrate that the 105 kD antigen possessed macrophage killing (leukotoxic) activity, as follows. Ten mls fresh bovine blood were diluted to 25 mls in 1× Hanks Balanced Salt Solution (HBSS), then 25 mls Ficoll-Hypaque were layered under the blood solution. This was spun 40 minutes at approximately 1500×g, at room temperature, to form a gradient. The top layer of the gradient was discarded and the second layer of the gradient, containing lymphocytes, was removed and saved. Similarly, the third layer was discarded, while the fourth layer, containing neutrophils was removed and saved. Ammonium chloride was added to the neutrophil and lymphocyte fractions to 0.43% and the mixtures were incubated 5 min. at room temperature to lyse any contaminating red blood cells. Each fraction was diluted to 50 ml in RPMI 1640 medium and the cells pelleted by centrifugation 40 minutes at 1500× g. This washing step was repeated twice more. Final cell volumes were approximately 10 ml, with each fraction containing about $10^7$ cells/ml.

To measure toxic activity, $2\times10^6$ neutrophils were mixed with various dilutions of sonicated whole cell lysates (10 minutes, 20 watts) of IPTG-induced $E. coli$ strains carrying either pBS + or pSH209 Cells plus sonicates were incubated 30 minutes at 37° C. then stained with Trypan blue and viable cells counted using light microscopy. As shown in Table II below, whereas an undiluted sonicate of the pBS + carrying strain did not cause any loss of neutrophil viability, the sonicate of the pSH209 carrying strain (SH027) killed 65% of these cells. As expected, neither sonicate caused any killing of lymphocytes.

TABLE II

Cytotoxic Activity of Pasteurella Toxin
Produced in *P. haemolytica* and *E. coli.*

|  | % Neutrophil Death |
|---|---|
| *P. haemolytica* supernatant | 60.4 |
| *P. haemolytica* whole cell sonicate | 61.7 |
| *E. coli* (PSH209) whole cell sonicate (IPTG induced culture) | 64.7 |
| *E coli* (pBS) whole cell sonicate (IPTG induced culture) | 0.1 |
| Control (medium only) | 0.0 |

6. Large Scale Preparation of Membrane-Associated Leukotoxin and Vaccine Compositions.

Strain SH027 carrying pSH209 was grown and IPTG-induced, as described above, in 250 ml L broth. Cells were collected by centrifugation, 5 min. at 10,000 rpm, and resuspended to a density of $7\times10^9$ cells/ml in 0.75M sucrose, 10 mM Tris, pH 7.8 containing 100 ug/ml lysozyme. This solution was incubated 2 min. on ice then slowly diluted with two volumes 1.5 mM EDTA, pH 7.5 over a period of 10 minutes. The spheroplasts formed by this procedure were osmotically shocked by pouring the suspension into 4 volumes ice cold water and stirring for 10 minutes at 4° C. Unbroken cells were removed from other cellular components by centrifugation at 1200×g, 15 minutes at 4° C. Membranes were collected by centrifuging the supernatant fraction at 60,000 rpm for 2 hours at 4° C. in a 70 Ti fixed angle rotor.

The membrane pellet was resuspended in 40 ml 0.25M sucrose, 33 mM Tris, pH 7.8, 1 mM EDTA and repelleted 2 hours at 60,000 rpm. The washed pellet was resuspended in 2.0 ml 25% sucrose, 5mM EDTA, pH 7.5 and overlayed onto a gradient composed of steps with the following sucrose concentrations and volumes: 55%, 5.0 ml; 50%, 6.3 ml; 45%, 6.3 ml; 40%, 6.3 ml; 35%, 6.3 ml; 30%, 6.3 ml; 25%, 6.3 ml. Gradients were centrifuged 24 hours at 35,000 rpm in a SW 41 rotor at 4° C. and then fractioned into 0.8 ml; fractions. Each fraction was diluted with 1 mM EDTA, pH 7.5, to a sucrose concentration of less than 10% and then concentrated by pelleting 2 hours at 65,000 rpm, 4° C. in a 70.1 Ti rotor. The pellets were resuspended in minimal volumes of 33 M Tris, pH 7.8 and the entire sample of each was used for Western blot analysis. This analysis indicated that the 105 kD leukotoxin was associated with both the inner and outer membranes of *E. coli*.

Vaccine compositions may include extracts of strain SH027 taken at several stages of the above purification scheme. For example, a sonicated whole cell extract of IPTG-induced cells, a crude membrane pellet, or purified inner and/or outer membranes may be used in conjunction with a suitable pharmaceutical carrier. In addition, a vaccine may be composed of any of the above, alone or in combination, mixed with any or all of the crude or cloned *P. haemolytica* supernatant antigens; this includes the 55 kD and 66 kD antigens that have also been cloned in *E. coli*.

D. Vaccine Preparation

Immunogenic compositions, suitable for use as a Shipping Fever vaccine, may be prepared most readily directly from *P. haemolytica* cell-free culture supernatant, by, for example, ammonium sulfate precipitation of supernatant proteins, to concentrate the proteins, followed by extensive dialysis to remove undesired small molecular weight molecules and/or lyophilization of the thus purified material for more ready formulation into a desired vehicle. There is no general requirement that the supernatant be molecular weight fractionated to provide the individual antigens in their most purified state because it has been found that the unfractionated supernatant itself will provide the antigens in a sufficiently substantially purified form to elicit an immune response in animals receiving such an immunogenic composition.

Alternatively, one may desire to formulate immunogen compositions using the antigen complex derived by gel exclusion chromatography of the supernatant proteins, which complex represents a more substantially purified antigen preparation relative to the supernatant. Alternatively, antigens derived by antibody-Sepharose chromatography of supernatant antigens may be employed. In an even more preferred embodiment, one or more, but preferably all, of the individual, isolated antigens are employed to prepare an antigenic protein "cocktail". Such cocktails may be prepared by the admixture of approximately equimolar amounts of the purified proteins, or alternatively, through the admixture of equi-antigenic amounts of one or more of the antigens.

In still further embodiments, immunogen compositions may be formulated to include one or both of the antigens produced by the recombinant cells of the present invention, these antigens being included in optimal amounts, for example, approximately equimolar or equi-antigenic amounts.

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents. pH buffering agents, or adjuvants which enhance the effectiveness of the vaccine.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10–95% of active ingredient, preferably 25–70%.

The proteins may be formulated into the vaccine as neutral or salt forms. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine. 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, capacity of the cow's immune system to synthesize antibodies, and the degree of protection desired. Precise amounts of active ingredient required to be administered depend on the judgment of the practitioner and are peculiar to each individual cow. However, suitable dosage ranges are of the order of several hundred micrograms active ingredient per animal. Suitable regimes for initial administration and booster shots are also variable, but are typified by an initial administration followed by subsequent inoculations or other administrations.

The manner of application may be varied widely. Any of the conventional methods for administration of a dead vaccine are applicable. These include oral application on a solid physiologically acceptable base or in a physiologically acceptable dispersion, parenterally, by injection or the like. The dosage of the vaccine will depend on the route of administration and will vary according to the size of the host. Because the vaccine is believed to have few if any side effects, relatively large dosages may be used without injury to the cow. Normally, the amount of the vaccine will be form about 1 mu g to 20.0 mg per kilogram of host, more usually from about 5 mu g to 2.0 mg given subcutaneously or intramuscularly after mixing with an appropriate carrier or an adjuvant to enhance immunization with the vaccine.

Various methods of achieving adjuvant effect for the vaccine includes use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° to 101° C. for 30 second to 2 minute periods respectively. Aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed.

More novel methods of adjuvanticity would include attenuated bacterial toxins against which the host has been preimmunized, or, by including in the vaccine composition a biologically or antigenically sufficient amount of *P. haemolytica* bacterin. Bacterin preparation is well known in the art and basically involves formalinization of live *P. haemolytica* cells as follows. Briefly, *P. haemolytica* cultures are grown in Brain Heart Infusion broth to mid-logarithmic phase then harvested and resuspended in phosphate buffered saline (PBS) to an equivalent cell density. The cells are then incubated overnight at room temperature in the presence of 0.5% formalin, reharvested and resuspended in PBS. Aliquots of the formalinized bacteria are mixed with aluminum hydroxide, incomplete Preund's or other suitable adjuvants and then used to inoculate test animals.

For best results it is believed that a weight ratio of about 1:1 to 1:5, bacterin:supernatant (or isolated supernatant proteins), respectively, should be employed.

The compound vaccine should elicit enhanced immune response to *P. haemolytica* infection. The amount of the adjuvant will vary widely depending upon the nature of the adjuvant, generally varying from 0.1 to 100 times the weight of the immunogen, more usually from 1 to 10 times.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labelling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

E. Antibody Generation and Further Embodiments

Antibodies to one or more of the *P. haemolytica* antigens, or antigen-containing compositions, may be obtained, in general, through immunization of a selected immunocompetent mammal with the antigen or composition, as the case may be. Satisfactory immunization protocols are well known, and have been dealt with extensively herein. However, it should be pointed out that the antibodies elicited in response to inoculation with *P. haemolytica* antigens have additional utility in and of themselves. For example, either polyclonal or monoclonal antibodies, regardless of species. derivation, can be employed in ELISA, or similar immunodetection assays, for the diagnosis of active or convalescent Pasteurellosis.

Additionally, immunized bovine sera can be fractionated to provide highly Pasteurella-immunoreactive sera in the form of bovine gamma-globulins.

To provide a general purpose anti-Pasteurella antibody composition, immunocompetent mammals are inoculated with one of the individual antigens or antigen compositions disclosed herein, typically together with a suitable immunoadjuvant, in a manner sufficient to elicit a Pasteurella antigen-specific immune response. Generally, the amount of antigen material employed will be chosen as is required under the individual circumstances. After a satisfactory response has been obtained, as gauged by immunoblot, ELISA or other immunologic detection test, an aliquot of blood is removed from the animal and the serum obtained therefrom. The serum is then fractionated, for example, by ammonium sulfate precipitation and dialysis, to provide the serum Ig fraction or subfractions thereof.

For more specific application, for example, for use in inducing a passive immunity to the disease, a pasteurella-specific hyperimmune bovine serum fraction is provided by inoculating a cow in a manner, for example, as detailed herein in Example I or Section D. A satisfactory immune response, as gauged by one of the various immunologic tests, will typically be obtained within 3 to 6 weeks, and may be further enhanced by repeated booster inoculations on a weekly basis. The resultant hyperimmune serum is then obtained and fractionated to provide, typically, the gamma globulin fraction. After suitable purification, for example, further dialysis or fractionation, the immunoglobulins may be formulated into a suitable pharmaceutical vehicle for parental administration. Depending on the immunoglobulin concentration and titer, generally 5 to 10 cc will be administered to animals, for example, high risk cattle exposed to the disease or being subjected to conditions which are conductive to the disease (high density containment, shipping, etc.) For more specific purposes, for example, for the immunodetection of specific, *P. haemolytica* individual antigens, one may desire to generate a hybridoma population which secreted monoclonal antibodies having specificity in general for *P. haemolytica* antigens, and selecting therefrom clones having specificity in particular for the individual antigens which have been identified herein.

Hybridoma development is well known, as exemplified by the aforementioned U.S. Pat. No. 4,196,265, and involves, in general, first immunizing a rodent, for example, a mouse or rat, with a selected antigen or antigen composition obtained in accordance with the present invention, in a manner sufficient to provide a satisfactory immune response. Spleen cells from the immunized animal are then fused with myeloma cells of the corresponding species. Typically, one may desire to employ immunocompetent mice and murine NS-1 myeloma cells.

The fused spleen/myeloma cells are then subjected to culturing in a selective medium, for example, HAT media (hypoxanthine, aminopterin, thymidine), to select fused spleen/myeloma cells from the parental cells. This culturing, in essence, provides the population of hybridomas from which specific hybridomas are selected. Typically, selection is performed by culturing the cells by single-clone dilution into microtiter plates, followed by testing the individual clonal supernatants for reactivity with one of the individual antigens. Most conveniently, the clonal supernatants are first screened by ELISA to identify as a whole those colonies reactive with *P. haemolytica* antigens, and then individual reactive colonies are screened by immunoblot to determine the antigenic specificity of the particular monoclonal antibody produced by each individual colony. The selected colony may then be propagated indefinitely to provide the monoclonal antibody containing supernatant.

The monoclonal or polyclonal antibodies may thus be provided in a form convenient for application in one of the conventional immunologic assay, for the detection of corresponding *P. haemolytica* antigens in various fluids, for example, biologic fluids obtained from cattle.

Alternatively, antibodies may be employed for specific isolation of individual *P. haemolytica* antigens, for example, by attachment to Sepharose and chromatography of antigen-containing compositions thereover. Individual antigen-specific monoclonal antibodies may thus be employed to isolate individual antigens for antigenic "cocktail" formulation.

It is believed that, for diagnostic application, preferred pasteurellosis diagnostic methods would employ P. haemolytica antigens, whether isolated or employed in the form of purified P. haemolytica supernatants, to immunoidentify the presence of P. haemolytica antibodies in biologic samples, tissue or fluids, obtained from a suspected infected animal. For detection in aqueous samples, the antigen, or antigen composition, is preferably adsorbed, or otherwise attached, to an appropriate adsorption matrix, for example, the inside surface of a microtiter dish well, and an aqueous suspected antibody-containing composition contacted therewith in a manner sufficient to promote specific immunocomplex formation. The matrix is then washed to remove non-specifically bound material and the amount of material which is specifically immunocomplexed thereto determined, typically through the use of an appropriate labeled ligand.

For the determination of an active infection, one may desire to further probe specific for bovine IgM molecules. It is known that a relative increase in the proportion of specific IgM is often indicative of an active, as opposed to convalescent or otherwise non-active, disease.

Accordingly, diagnostic kits may be developed which include aliquots of one or more of the *P. haemolytica* antigens, or antigen-containing compositions, which are, preferably, provided in a form which is suitable for application to microtiter dish wells. Alternatively, or in addition, the kits will include antibody compositions having specificity for one or more of the antigens. Both antibody and antigen preparations should preferably be provided in a suitably titrated form, with antigen concentrations and/or antibody titers given for easy reference in quantitative applications.

The kits will also typically include an immunodetection reagent or label for the detection of specific immunoreaction between the provided antigen and/or antibody, as the case may be, and the diagnostic sample. Suitable detection reagents are well known in the art as exemplified by radioactive, enzymatic or otherwise chromogenic ligands, which are typically employed in association with the antigen and/or antibody, or in association with a second antibody having specificity for the antigen or first antibody. Thus, the reaction is detected or quantified by means of detecting or quantifying the label. Immunodetection reagents and processes suitable for application in connection with the novel compositions of the present invention are generally well known in the art.

What is claimed is:

1. A process for preparing a *P. haemolytica* antigen comprising the steps of:

(a) culturing *P. haemolytica* bacteria to produce a cell-free supernatant without lysing the bacteria, the supernatant having individual *P. haemolytica* secreted polypeptides;

(b) subjecting polypeptides of the culture supernatant to molecular weight fractionation to fractionate the polypeptides according to their molecular weight;

(c) identifying an antigen having binding affinity for immune sera from pasteurellosis infected cows; and (d) purifying the identified antigen wherein the identified antigen has a molecular weight of approximately 105 kD, as determined by SDS polyacrylamide gel electrophoresis.

2. A process for preparing a *P. haemolytica* antigen comprising the steps of:

(a) obtaining an antibody preparation which includes antibodies against the P. haemolytica antigen;

(b) preparing an immunoaffinity chromatography substrate from the antibody preparation;

(c) culturing *P. haemolytica* bacteria to produce a cell-free culture supernatant without lysing the bacteria, the supernatant having individual *P. haemolytica* secreted polypeptides; and (d) immunopurifying the antigen from the cell-free culture supernatant by immunoaffinity chromatography of the supernatant on the immunoaffinity chromatography substrate wherein the antigen has a molecular weight of approximately 105 kD, as determined by SDS polyacrylamide gel electrophoresis.

3. The process of claim 2, wherein the antibody preparation comprises an antibody prepared in vitro against an antigen composition having the following properties:

(a) binding affinity for immune sera obtained from a pasteurellosis infected cow;

(b) an approximate reference molecular weight of 105 K Daltons, the molecular weight being ascertainable by SDS polyacrylamide gel electrophoresis and immunoblot analysis; and (c) immunological cross-reactivity with a 105 K Dalton *P. haemolytica* antigen having an amino terminal sequence of M-G-T-R-L-T-T-L-S-N- (SEQ ID NO:1) and a carboxy terminal sequence of -L-S-S-L-Q-F-A-R-A-A (SEQ ID NO: 2).

4. A process for preparing a *P. haemolytica* cytotoxin antigen preparation comprising the steps of:

(a) culturing *P. haemolytica* bacteria to produce a supernatant, the supernatant comprising individual *P. haemolytica* secreted proteins; and (b) subjecting said supernatant to fractionation to enrich for proteins having a molecular weight greater than 15 Kd, while substantially retaining the cytotoxin antigen, wherein the cytotoxin antigen is defined as having the following properties:

binding affinity for immune sera obtained from a pasteurellosis infected cow; and an approximate reference molecular weight of 105 Kd, the molecular weight being ascertainable by SDS polyacrylamide gel electrophoresis and immunoblot analysis.

5. The process of claim 4, further comprising concentration of the supernatant.

6. The process of claim 4, further comprising subjecting the antigen preparation to ion exchange chromatography or gel filtration chromatography.

7. The process of claim 4, further comprising purifying the antigen preparation so as to decrease the amount of protein antigens having a molecular weight less than about 29 Kd.

8. The antigen of claim 7, wherein the antigen preparation is purified so as to decrease the amount of protein antigens having a molecular weight less than about 73 Kd.

9. A process for preparing a purified antigen having the following properties:

binding affinity for immune sera obtained from a pasteurellosis infected cow;

an approximate reference molecular weight of 105 K Daltons, the molecular weight being ascertainable by SDS polyacrylamide gel electrophoresis and immunoblot analysis; and immunological cross-reactivity with a 105 K Dalton *P. haemolytica* antigen found in cell-free supernatant following growth of *P. haemolytica* cells in culture;

wherein the process comprises preparing the antigen by:

a) culturing *P. haemolytica* bacteria to produce a cell-free supernatant, the supernatant comprising individual *P. haemolytica* secreted proteins; and i) subjecting said supernatant to concentration and dialysis using a dialysis membrane having a molecular weight cutoff of at least 15 Kd;

ii) subjecting the supernatant to ammonium sulfate precipitation, iii) subjecting the supernatant to gel exclusion chromatography; or iv) subjecting the supernatant to ion exchange chromatography; and b) recovering said antigen.

10. The process of claim 4, further comprising concentrating the supernatant or preparation by lyophilization.

11. The process of claim 4, wherein fractionation is achieved by dialysis.

12. The process of claim 4, wherein fractionation is achieved by filtration.

13. The process of claim 4, further comprising rendering the preparation pharmaceutically acceptable.

* * * * *

UNITED STATES PATENT AND TRADEMARK OFFICE
CERTIFICATE OF CORRECTION

PATENT       : 5,932,705

DATED        : August 3, 1999

INVENTOR(S) : Peter Berget, Michael Engler, Sarah Highlander, and George Weinstock It is certified that error appears in the above-identified patent and that said Letters Patent is hereby corrected as shown below:

The title page should be deleted to be replaced with the attached title page.

The drawing sheet, consisting of Fig. 9L, should be added as shown on the attached page.

The drawing sheets 1-21 has been renumbered to sheets 1-22, as shown on the attached pages.

Signed and Sealed this

Twenty-fifth Day of April, 2000

Attest:

Q. TODD DICKINSON

*Attesting Officer*          *Director of Patents and Trademarks*

United States Patent [19]
Berget et al.

[11] Patent Number: 5,932,705
[45] Date of Patent: Aug. 3, 1999

[54] METHODS AND COMPOSITIONS FOR THE TREATMENT AND DIAGNOSIS OF SHIPPING FEVER

[75] Inventors: Peter Berget, Pittsburgh, Pa.; Michael Engler, Houston, Tex.; Sarah Highlander, Houston, Tex.; George Weinstock, Houston, Tex.

[73] Assignee: Board of Regents, University of Texas System

[21] Appl. No.: 08/286,690

[22] Filed: Aug. 5, 1994

Related U.S. Application Data

[62] Division of application No. 07/899,100, Jun. 15, 1992, Pat. No. 5,336,491, which is a continuation of application No. 07/540,261, Jun. 18, 1990, abandoned, which is a division of application No. 07/085,430, Aug. 13, 1987, Pat. No. 4,957,739, which is a continuation of application No. 06/935,806, Nov. 28, 1986, abandoned.

[51] Int. Cl.$^6$ .................... A23J 1/00; A61K 39/00; A61K 39/102

[52] U.S. Cl. .................. 530/413; 424/190.1; 424/255.1; 435/69.1; 435/69.3; 435/71.1; 435/71.2; 530/344; 530/350; 530/387.9; 530/388.4; 530/389.5

[58] Field of Search .................... 424/255.1, 190.1; 530/350, 344, 387.9, 388.4, 389.5, 413; 435/69.1, 69.3, 71.1, 71.2

[56] References Cited

U.S. PATENT DOCUMENTS

| | | | |
|---|---|---|---|
| 4,328,210 | 5/1982 | Kucera | 424/92 |
| 4,335,106 | 6/1982 | Kucera | 424/92 |
| 4,388,299 | 6/1983 | Kucera | 424/92 |
| 4,506,017 | 3/1985 | Kucera | 424/93 |
| 4,559,306 | 12/1985 | Kucera | 424/92 |
| 4,626,430 | 12/1986 | Kucera | 424/92 |
| 5,055,400 | 10/1991 | Lo et al. | 435/69.1 |
| 5,165,924 | 11/1992 | Shewen et al. | 424/88 |

FOREIGN PATENT DOCUMENTS

| | | | |
|---|---|---|---|
| 2023420 | 1/1980 | United Kingdom | 424/92 |

OTHER PUBLICATIONS

Biberstein, "HPA in Veterinary Medicine," pp. 62–66, date of publication unsure.
Frank, "Respiratory Disease in Cattle," from Proceedings of the 83rd Annual Meeting USAHA, 1979.
Markham et al. (1980), Am. J. Vet. Res., 41:18–22.
Karn et al. (1980), Proc. Natl. Acad. Sci., U.S.A., 77:5512.
Kaehler et al. (1980), Infect. Immun., 30:615.
Wilkie, "Pasteurella Immunization—Helpful or Harmful?," Notes from presentation at AABP Conference, 1980.
Himmel et al. (1982), Am. J. Vet. Res., 43:764–767.
Baluyut et al. (1981), Am. J. Vet. Res., 42:1920–1926.
Mulla and Thomson (1981), Can. Vet. J., 22:1.
Shewen et al. (1982), Infect. Immun., 35:91.
Markham et al. (1982), Am. J. Vet. Res., 43:285.
Yates et al. (1983), Can. J. Comp. Med., 47:250.
Frischauf et al. (1983), J. Mol. Biol., 170:827.
Otulakowski et al. (1983), Infect. Immun., 42:64.
Shewen et al. (1983), Am. J. Vet. Res., 44:715.
Shewen et al. (1983), Can. J. Comp. Med., 47:497.
Kucera et al. (1983), Am. J. Vet. Res., 44:1848.
Cho et al. (1984), Can J. Comp. Med., 48:151.
Filion et al. (1984), Can J. Comp. Med., 48:268.
Confer et al. (1985), Vet. Immunol. Immunopath., 10:265.
Lessley et al. (1985), Vet. Immunol. Immunopath., 10:279.
Frank, "Bacteria as Etiologic Agents in Bovine Respiratory Disease," pp. 348–362.
Lo et al. (1985), Infect. Immun., 50:667–671.
Gonzalez-Rayos et al. (1986), Infect. Immun., 53:505.
Lo et al. (1986), Biochem. Cell. Biol., 64:73.
Promega Biotec. Spec. Sheets.
Chang et al. (1986), Am. J. Vet. Res., 47:47:716.
Dialog Search Report.
Squire et al. (1984), Infect. Immun., 45(3):667–673.
McKinney et al. (1985), Vet. Microbiology, 10:465 (Abstract only).
Donachie et al. (1983), Vet. Microbiology, 8:199 (Abstract only).
Wilkie et al. (1980), Am. J. Vet. Res., 41:1773–1778.
Gentry et al. (1982), Am. J. Vet. Res., 43:2070–2073.
Gilmour et al. (1982), Vet. Record, 110:450.
Gentry et al. (1985), Vet. Immunol. Immunopath., 9:239–250.
Shewen et al. (1985), Am. J. Vet. Res., 46:1212–1214.
Durham et al. (1986), Am. J. Vet. Res., 47:1946–1951.
Mosier et al. (1986), Am. J. et. Res., 47:2233–2241.
Confer et al. (1988), JAVMA, 193:1308–1316.
Highlander et al. (1989), DNA, 8:15–28.
Mosier et al. (1989), Infect. Immun., 57:711–716.
Donachie et al. (1984), "Comparison of Cell Surface Antigen Extracts From Two Serotypes of Pasteurella haemolytica," J. Gen. Microbiology, 130:1209–1216.
Shewen and Wilkie (1983), "Immunity to Pasteurella haemolytica Serotype 1," Abstract for N. American Symposium on Bovine Respiratory Disease, Amarillo, Texas, pp. 480–481.

Primary Examiner—James C. Housel
Assistant Examiner—Jennifer Shaver
Attorney, Agent, or Firm—Arnold, White and Durkee

[57] ABSTRACT

Novel compositions are disclosed for use in the treatment or diagnosis of bovine pasteurellosis, commonly referred to as Shipping Fever. Cell-free *Pasteurella haemolytica* supernatants are employed to provide individual antigen compositions, identified through reaction with sera from naturally-infected or convalescent cattle. In particular, at least seven individual *P. haemolytica* antigen groups were recognized in cell-free culture supernatants. Purified *P. haemolytica* supernatant, formulated in a suitable pharmaceutical vaccine composition is shown to elicit a specific immune response, in both cows and rabbits, directed against the individual immunoreactive *P. haemolytica* polypeptides identified. Also disclosed are novel recombinant cells, plasmids and bacteriophage which include transcriptionally active *P. haemolytica* antigen genes. Recombinant clones are similarly selected to be reactive with naturally-infected antisera. Examples, and further disclosure, are also provided which demonstrate the utility of a presently disclosed antibody and antigen compositions in immuno-detection of both antigens and antibodies in various biological samples.

13 Claims, 22 Drawing Sheets

```
BglII                              *                                    Nucleotide #
                                                                                  *
GATCTATACGCTTTTATCCAAAGCAGAAAG AATTAGGCAAAATTGCCTACTTTAAAGGAG 90                                                         *
GTAAATTAGATAAAAAAACAGCAAAAAAAC GTTTTGATACATATCAAGAAGAGCTGGCAA

*                                                         180
CACGACTTAAAAATGAATTTAATTTTATTA AAAAATAGAAGGAGACATCCCTTATGGGAA
                                                   PtxA protein:  M  G

*                                                *
CTAGACTTACAACCCTATCAAATGGGCTAA AAAACACTTTAACGGCAACCAAAAGTGGCT
 T  R  L  T  T  L  S  N  G  L   K  N  T  L  T  A  T  K  S  G

270                                                        *
TACATAAAGCCGGTCAATCATTAACCCAAG CCGGCAGTTCTTTAAAAACTGGGGCAAAAA
 L  H  K  A  G  Q  S  L  T  Q   A  G  S  S  L  K  T  G  A  K
              30

*                                           360
AAATTATCCTCTATATTCCCCAAAATTACC AATATGATACTGAACAAGGTAATGGTTTAC
 K  I  I  L  Y  I  P  Q  N  Y   Q  Y  D  T  E  Q  G  N  G  L
                                                             60

*                                                        *
AGGATTTAGTCAAAGCGGCCGAAGAGTTGG GGATTGAGGTACAAAGAGAAGAACGCAATA
 Q  D  L  V  K  A  A  E  E  L   G  I  E  V  Q  R  E  E  R  N

450                                                        *
ATATTGCAACAGCTCAAACCAGTTTAGGCA CGATTCAAACCGCTATTGGCTTAACTGAGC
 N  I  A  T  A  Q  T  S  L  G   T  I  Q  T  A  I  G  L  T  E
              90

*                                                540
GTGGCATTGTGTTATCCGCTCCACAAATTG ATAAATTGCTACAGAAAACTAAAGCAGGCC
 R  G  I  V  L  S  A  P  Q  I   D  K  L  L  Q  K  T  K  A  G
                                                            120
```

FIG. 9A

```
                    *                                    *
AAGCATTAGGTTCTGCCGAAAGCATTGTAC  AAAATGCAAATAAAGCCAAAACTGTATTAT
 Q  A  L  G  S  A  E  S  I  V    Q  N  A  N  K  A  K  T  V  L

630                                   *
CTGGCATTCAATCTATTTTAGGCTCAGTAT  TGGCTGGAATGGATTTAGATGAGGCCTTAC
 S  G  I  Q  S  I  L  G  S  V    L  A  G  M  D  L  D  E  A  L
                   150

*                        720
AGAATAACAGCAACCAACATGCTCTTGCTA  AAGCTGGCTTGGAGCTAACAAATTCATTAA
 Q  N  N  S  N  Q  H  A  L  A    K  A  G  L  E  L  T  N  S  L
                                                 180

*                                    *
TTGAAAATATTGCTAATTCAGTAAAAACAC  TTGACGAATTTGGTGAGCAAATTAGTCAAT
 I  E  N  I  A  N  S  V  K  T    L  D  E  F  G  E  Q  I  S  Q

810                                    *
TTGGTTCAAAACTACAAAATATCAAAGGCT  TAGGGACTTTAGGAGACAAACTCAAAAATA
 F  G  S  K  L  Q  N  I  K  G    L  G  T  L  G  D  K  L  K  N
                   210

*                             900
TCGGTGGACTTGATAAAGCTGGCCTTGGTT  TAGATGTTATCTCAGGGCTATTATCGGGCG
 I  G  G  L  D  K  A  G  L  G    L  D  V  I  S  G  L  L  S  G
                                                 240

*                                    *
CAACAGCTGCACTTGTACTTGCAGATAAAA  ATGCTTCAACAGCTAAAAAAGTGGGTGCGG
 A  T  A  A  L  V  L  A  D  K    N  A  S  T  A  K  K  V  G  A

990                                    *
GTTTTGAATTGGCAAACCAAGTTGTTGGTA  ATATTACCAAAGCCGTTTCTTCTTACATTT
 G  F  E  L  A  N  Q  V  V  G    N  I  T  K  A  V  S  S  Y  I
                   270
```

FIG. 9B

```
                                              *                      1080
TAGCCCAACGTGTTGCAGCAGGTTTATCTT CAACTGGGCCTGTGGCTGCTTTAATTGCTT
L  A  Q  R  V  A  A  G  L  S    S  T  G  P  V  A  A  L  I  A
                                                 300

*                                              *
CTACTGTTTCTCTTGCGATTAGCCCATTAG CATTTGCCGGTATTGCCGATAAATTTAATC
S  T  V  S  L  A  I  S  P  L    A  F  A  G  I  A  D  K  F  N

1170                                        *
ATGCAAAAAGTTTAGAGAGTTATGCCGAAC GCTTTAAAAAAATTAGGCTATGACGGAGATA
H  A  K  S  L  E  S  Y  A  E    R  F  K  K  L  G  Y  D  G  D
              330

*                               1260
ATTTATTAGCAGAATATCAGCGGGGAACAG GGACTATTGATGCATCGGTTACTGCAATTA
N  L  L  A  E  Y  Q  R  G  T    G  T  I  D  A  S  V  T  A  I
                                                    360

*                                        *
ATACCGCATTGGCCGCTATTGCTGGTGGTG TGTCTGCTGCTGCAGCCGGCTCGGTTATTG
N  T  A  L  A  A  I  A  G  G    V  S  A  A  A  A  G  S  V  I

1350                                              *
CTTCACCGATTGCCTTATTAGTATCTGGGA TTACCGGTGTAATTTCTACGATTCTGCAAT
A  S  P  I  A  L  L  V  S  G    I  T  G  V  I  S  T  I  L  Q
              390

*                                  1440
ATTCTAAACAAGCAATGTTTGAGCACGTTG CAAATAAAATTCATAACAAAATTGTAGAAT
Y  S  K  Q  A  M  F  E  H  V    A  N  K  I  H  N  K  I  V  E
                                                 420

*                                     *
GGGAAAAAAAATAATCACGGTAAGAACTACT TTGAAAATGGTTACGATGCCCGTTATCTTG
W  E  K  N  N  H  G  K  N  Y     F  E  N  G  Y  D  A  R  Y  L
```

FIG. 9C

```
                1530
CGAATTTACAAGATAATATGAAATTCTTAC TGAACTTAAACAAAGAGTTACAGGCAGAAC
 A  N  L  Q  D  N  M  K  F  L   L  N  L  N  K  E  L  Q  A  E
               450

*                       1620
GTGTCATCGCTATTACTCAGCAGCAATGGG ATAACAACATTGGTGATTTAGCTGGTATTA
 R  V  I  A  I  T  Q  Q  W      D  N  N  I  G  D  L  A  G  I
                                              480

*                                        *
GCCGTTTAGGTGAAAAAGTCCTTAGTGGTA AAGCCTATGTGGATGCGTTTGAAGAAGGCA
 S  R  L  G  E  K  V  L  S  G   K  A  Y  V  D  A  F  E  E  G

1710                                              *
AACACATTAAAGCCGATAAATTAGTACAGT TGGATTCGGCAAACGGTATTATTGATGTGA
 K  H  I  K  A  D  K  L  V  Q   L  D  S  A  N  G  I  I  D  V
            510

*                              1800
GTAATTCGGGTAAAGCGAAAACTCAGCATA TCTTATTCAGAACGCCATTATTGACGCCGG
 S  N  S  G  K  A  K  T  Q  H   I  L  F  R  T  P  L  L  T  P
                                                     540

*                                      *
GAACAGAGCATCGTGAACGCGTACAAACAG GTAAATATGAATATATTACCAAGCTCAATA
 G  T  E  H  R  E  R  V  Q  T   G  K  Y  E  Y  I  T  K  L  N

1890                                            *
TTAACCGTGTAGATAGCTGGAAAATTACAG ATGGTGCAGCAAGTTCTACCTTTGATTTAA
 I  N  R  V  D  S  W  K  I  T   D  G  A  A  S  S  T  F  D  L
            570
```

FIG. 9D

```
                                    *                                    1980
CTAACGTTGTTCAGCGTATTGGTATTGAAT TAGACAATGCTGGAAATGTAACTAAAACCA
 T  N  V  V  Q  R  I  G  I  E   L  D  N  A  G  N  V  T  K  T
                                                    600

*                                    *
AAGAAACAAAAATTGCCCGGAAACTTGGTG AAGGTGATGACAACGTATTTGTTGGTTCTG
 K  E  T  K  I  I  A  K  L  G   E  G  D  D  N  V  F  V  G  S

2070                                        *
GTACGACGGAAATTGATGGCGGTGAAGGTT ACGACCGAGTTCACTATAGCCGTGGAAACT
 G  T  T  E  I  D  G  G  E  G   Y  D  R  V  H  Y  S  R  G  N
                  630

*                                    2160
ATGGTGCTTTAACTATTGATGCAACCAAAG AGACCGAGCAAGGTAGTTATACCGTAAATC
 Y  G  A  L  T  I  D  A  T  K   E  T  E  Q  G  S  Y  T  V  N
                                                    660

*                                    *
GTTTCGTAGAAACCGGTAAAGCACTACACG AAGTGACTTCAACCCATACCGCATTAGTGG
 R  F  V  E  T  G  K  A  L  H   E  V  T  S  T  H  T  A  L  V

2250                                        *
GCAACCGTGAAGAAAAAATAGAATATCGTC ATAGCAATAACCAGCACCATGCCGGTTATT
 G  N  R  E  E  K  I  E  Y  R   H  S  N  N  Q  H  H  A  G  Y
                  690

*                                    2340
ACACCAAAGATACCTTGAAAGCTGTTGAAG AAATTATCGGTACATCACATAACGATATCT
 Y  T  K  D  T  L  K  A  V  E   E  I  I  G  T  S  H  N  D  I
                                                    720

*                                    *
TTAAAGGTAGTAAGTTCAATGATGCCTTTA ACGGTGGTGATGGTGTCGATACTATTTACG
 F  K  G  S  K  F  N  D  A  F   N  G  G  D  G  V  D  T  I  Y
```

FIG. 9E

```
                              2430                                *
GTAACGACGGCAATGACCGCTTATTTGGTG GTAAAGGCGATGATATTCTCGATGGTGGAA
 G  N  D  G  N  D  R  L  F  G   G  K  G  D  D  I  L  D  G  G
                 750

*                          2520
ATGGTGATGATTTTATCGATGGCGGTAAAG GCAACGACCTATTACACGGTGGCAAGGGCG
 N  G  D  D  F  I  D  G  G  K   G  N  D  L  L  H  G  G  K  G
                                                  780

*                                  *
ATGATATTTTCGTTCACCGTAAAGGCGATG GTAATGATATTATTACCGATTCTGACGGCA
 D  D  I  F  V  H  R  K  G  D   G  N  D  I  I  T  D  S  D  G

2610                                               *
ATGATAAATTATCATTCTCTGATTCGAACT TAAAAGATTTAACATTTGAAAAAGTTAAAC
 N  D  K  L  S  F  S  D  S  N   L  K  D  L  T  F  E  K  V  K
                 810

*                            2700
ATAATCTTGTCATCACGAATAGCAAAAAAG AGAAAGTGACCATTCAAAACTGGTTCCGAG
 H  N  L  V  I  T  N  S  K  K   E  K  V  T  I  Q  N  W  F  R
                                                  840

*                                 *
AGGCTGATTTTGCTAAAGAAGTGCCTAATT ATAAAGCAACTAAAGATGAGAAAATCGAAG
 E  A  D  F  A  K  E  V  P  N   Y  K  A  T  K  D  E  K  I  E

2790                                           *
AAATCATCGGTCAAAATGGCGAGCGGATCA CCTCAAAGCAAGTTGATGATCTTATCGCAA
 E  I  I  G  Q  N  G  E  R  I   T  S  K  Q  V  D  D  L  I  A
                 870

*                       2880
AAGGTAACGGCAAAATTACCCAAGATGAGC TATCAAAAGTTGTTGATAACTATGAATTGC
 K  G  N  G  K  I  T  Q  D  E   L  S  K  V  V  D  N  Y  E  L
                                                  900
```

FIG. 9F

```
                              *                                          *
TCAAACATAGCAAAAATGTGACAAACAGCT TAGATAAGTTAATCTCATCTGTAAGTGCAT
 L  K  H  S  K  N  V  T  N  S  L  D  K  L  I  S  S  V  S  A

2970                                                   *
TTACCTCGTCTAATGATTCGAGAAATGTAT TAGTGGCTCCAACTTCAATGTTGGATCAAA
 F  T  S  S  N  D  S  R  N  V  L  V  A  P  T  S  M  L  D  Q
            930

*                                       3060
GTTTATCTTCTCTTCAATTTGCTAGAGCAG CTTAATTTTAATTGATTGGCAACTCTATAT
 S  L  S  S  L  Q  F  A  R  A  A  *
                                953

*                                          *
TGTTTCACACATTATAGAGTTGCCGTTTTA TTTTATAAAAGGAGACAATATGGAAGCTAA

3150
CCATCAAAGGAATGATCTTGGTTTAGTTGC CCTCACTATGTTGGCACAATACCATAATAT

*                                       3240
TTCGCTTAATCCGGAAGAAATAAAACATAA ATTTGATCTTGACGGAAAAGGGCTTTCTTT

*                                          *
AACTGCTTGGCTTTTAGCTGCAAAATCGTT AGCGTTGAAAGCGAAACACATTAAAAAAGA

3330                                                   *
GATTTCCCGCTTACACTTGGTGAATTTACC GGCATTAGTTTGGCAAGATAACGGTAAACA

*                                       3420
TTTTTTATTGGTAAAAGTGGATACCGATAA TAACCGCTATTTAACTTACAATTTGGAACA

*                                          *
AGATGCTCCACAAATTCTGTCAACAGACGA ATTTGAAGCCTGCTATCAAGGGCAGTTAAT

3510                                                   *
TTTGGTCACGTCCAGAGCTTCCGTAGTAGG TCAATTAGCAAAGTTCGATTTCACCTGGTT
```

FIG. 9G

```
                              3600
TATTCCGGCGGTGATCAAATACCGAAAAAT CTTTCTAGAAACCTTGATTGTTTCGATCTT

TTTGCAAATTTTTGCCCTAATTACACCGCT ATTCTTCCAAGTTGTTATGGATAAAGTACT

3690
GGTGCATCGAGGTTTTTCAACCTTGAATAT CATTACGGTTGCCTTAGCTATTGTGATCAT

3780
CTTTGAAATTGTACTAAGTGGTTTGAGAAC CTATGTTTTTTCTCATAGCACTASCCGTAT

TGATGTTGAATTAGGCGCTAAATTATTTCG ACATTTATTATCACTACCCATTTCTTATTT

3870
TGAAAACAGACGAGTTGGAGATACAGTCGC TAGGGTTAGAGAATTAGATCAAATTCGTAA

3960
TTTCCTTACCGGACAAGCATTAACCTCGGT GTTAGATCTCTTATTCTCTTTTATCTTTTT

TGCCGTAATGTGGTATTACAGCCCAAAATT AACCTTGGTAATTCTTGGTTCATTGCCCTG

4050
CTATATTTTATGGTCAATTTTTATTAGTCC GATTTTAAGACGGCGTTTAGATGAGAAATT

4140
TGCCCGAAGTGCTGATAACCAAGCATTCTT AGTTGAGTCGGTAACAGCCATCAATATGAT

TAAAGCGATGGCGGTTGCTCCACAAATGAC GGATACATGGGATAAACAGCTGGCAAGCTA

4230
TGTTTCATCAAGTTTCCGTGTCACCGTATT AGCAACCATTGGGCAACAAGGTGTACAACT

4320
TATTCAAAAAACCGTTATGGTGATTAACCT TTGGTTAGGGGCACACTTAGTTATTTCAGG
```

FIG. 9H

```
                              *                                         *
         CGATCTGAGTATTGGGCAATTAATTGCCTT TAATATGCTATCAGGGCAAGTGATTGCACC

4410                                        *
         GGTGATTCGGCTGGCTCAGCTCTGGCAAGA TTTCCAACAAGTTGGGATTTCCGTCACTCG

*                                      4500
         CTTAGGTGATGTTTTAAACTCTCCAACCGA ACAATATCAAGGCAAATTATCACTACCAGA

*                                         *
         AATAAAAGGCGATATCTCATTTAAAAATAT CCGCTTTAGATATAAACCAGATGCACCAAC

4590                                        *
         TATTTTAAATAATGTGAATTTAGAAATTAG GCAAGGAGAAGTGATTGGGATTGTTGGACG

*                                      4680
         TTCCGGTTCAGGCAAAAGTACTCTGACTAA ATTACTGCAACGTTTTTATATTCCTGAAAA

*                                         *
         TGGGCAGGTTTTGATTGATGGACATGATCT AGCCTTAGCTGATCCAAACTGGCTACGCCG

4770                                        *
         TCAAATAGGTGTAGTGCTGCAAGATAATGT GTTATTAAACCGCAGTATCCGAGAAAATAT

*                                      4860
         TGCGCTATCAGATCCAGGAATGCCAATGGA GCGAGTAATTTATGCAGCAAAATTAGCAGG

*                                         *
         GGCTCACGATTTTATTTCAGAATTGCGTGA AGGTTATAACACCATTGTGGGTGAACAAGG

4950                                        *
         AGCGGGGCTTTCAGGCGGGCAACGCCAACG GATTGCGATTGCTCGAGCTTTGGTAAACAA

*                                      5040
         CCCGAAAATCCTGATTTTTGATGAGGCAAC CAGTGCCCTCGATTACGAATCTGAGCATAT

*                                         *
         TATTATGCAAAATATGCAAAAAATATGCCA AGGCAGAACCGTGATTTTGATTGCACATCG
```

FIG. 9I

```
                          5130                                              *
       TTTATCGACCGTCAAAAATGCGGATCGAAT TATTGTGATGGAAAAGGGGGAAATTGTTGA

*                                             5220
       GCAAGGCAAGCACCACGAATTACTGCAAAA CAGTAACGGACTTTATTCCTACTTACACCA

*                                               *
       ATTACAACTTAATTAAGAAGGAAAACAATG AAAATATGGCTTAGTGGTATTTATGAATTT

5310                                              *
       TTCCTACGCTATAAAAACATTTGGGCAGAA GTATGGAAAATTCGTAAAGAATTAGACCAC

*                                             5400
       CCAAACAGAAAAAAAGACGAAAGTGAATTT TTACCGGCACATTTAGAACTGATTGAAACC

*                                               *
       CCGGTTTCTAAAAAACCACGTCTAATTGCT TATTTGATTATGCTATTTTTAGTTGTGGCA

5490                                              *
       ATTGTGCTTGCCAGTGTAAGCAAAGTTGAA ATTGTGGCGACTGCTCCCGGTAAATTAACT

*                                             5580
       TTTAGTGGCAGAAGTAAAGAAATTAAACCG ATTGAAAACGCCATTGTACAAGAAATTTTC

*                                               *
       GTTAAAGATGGGCAGTTTGTGGAAAAAGGG CAATTATTAGTCAGCTTAACTGCATTGGGT

5670                                              *
       TCTGATGCAGATATCAAAAAGACCATGGCT TCACTTTCTTTAGCTAAACTGGAGAACTAT

*                                             5760
       CGCTACCAAACTTTGCTTACTGCCATTGAA AAAGAGTCCTTGCCGGTGATTGATTTATCT

*                                               *
       AGAACCGAATTTAAAGATTCATCGGAAGAA GATCGACTACGTATTAAACACTTAATTGAG

5850                                              *
       GAGCAATACACCACTTGGCAAAAACAAAAA ACACAGAAAACTTTAGCGTATAAGCGTAAA
```

FIG. 9J

```
                                            *                            5940
GAGGCTGAAAAACAAACAATATTTGCCTAT  GTCCGTAAATATCAAGGTGCAACACGTATT

*                                     *
GAACAAGAAAAATTAAAAGACTTTAAGGCA  CTTTATAAACAGAAGTCTTTATCTAAGCAC

6030                                       *
GAACTTCTTGCGCAAGAAAATAAATTAATT  GAGGCTCAGAATGCAGTAGCTGTTTATCGC

*                                6120
TCAAAATTAAATGAATTAGAAAATGATCTA  CTCAATGTAAAAGAAGAACTTGAATTGATC

*                                  *
ACGCAATTCTTTAAAAGCGATGTGTTGGAA  AAATTAAAGCAACATATTGAAAATGAACGC

6210                                       *
CAACTTCGGCTCGAGTTAGAAAAAAATAAT  CAACGCAGACAGGCCTCGATGATCAGAGCA

*                                 6300
CCGGTTTCCGGTACGGTTCAGCAACTGAAA  ATTCACACTATAGGTGGTGTTGTTACGACT

*                                 *
GCTGAAACCTTGATGATCATTGTGCCGGAA  GACGATGTGTTAGAGGCCACCGCTCTGGTT

6390                                       *
CCAAACAAAGATATCGGCTTTGTTGCAGCA  GGGCAGGAGGTGATTATTAAAGTGGAAACT

*                                 6480
TTCCCTTATACACGCTATGGTTATCTAACT  GGTCGAATTAAACATATTAGCCCGGATGCG

*                                 *
ATTGAACAACCTAATGTAGGCTTAGTTTTT  AATGCAACTATAGCTATAGATAGGAAGAAT

6570                                       *
CTAACATCGCCTGATGGGCGAAAAATTGAT  TTGAGTTCAGGTATGACAATAACTGCTGAA

*                                 6660
ATCAAAACCGGTGAACGGAGTGTAATGAGT  TATTTACTCAGCCCATTAGAAGAATCTGTC
```

FIG. 9K

```
                         *                                    *
        ACAGAAAGTTTAAGGGAACGCTAATCGAAC CAAAACAAAGCCATAAAAGCCATTTTTGAGC

6750                                   *
        TTTTATGGCTTTATTTTTTAGTCCACAAGC GGTCAAAAAAGCCCAATTTTTTACACTTTT

*                                  6840
        ATAACAAATTGTTCTAACTAAAAATTACTA ATTCTTTTCTTTTATAGCGATCTCTATTTC

*                                    *
        ATTTCATTAACATTGACTAGAAGGGATTAT GAGCCTAAGCATTACGAATCTTTCTCTTGG

6930                                   *
        CTACCGCAAAAATCAGCAAAGGCTTATTTG AAAAGCACGGTGTCGAGGTGGAAAAACCGG

*                                  7020
        TGATGTTTCGCAGCTGGGCTCAGTTGGTGG AAGCTTTTTAAGTGGCAATGTGAACGTGGT

*                                    *
        GCATCTGCTTTCGCCTATGAGTTTGTGGGC GAAATATGGAGCAAATGCTCCGGTGAAAGC

7110                                   *
        GGTAATGTGGAATCACTTGGCAGGTTCGGC TTTAACGGTTCGCCCTGAAATCAACAGTAT

*                   7184
        TGCCGAACTCTCCGGCAAAACGGTAGAACT TCCGTTTTGGTATT
```

FIG. 9L